US008124334B2

(12) United States Patent
Donegan et al.

(10) Patent No.: US 8,124,334 B2
(45) Date of Patent: Feb. 28, 2012

(54) SELECTIVE DETECTION OF ONCOGENIC HPV

(75) Inventors: James J. Donegan, Long Beach, NY (US); Elazar Rabbani, New York, NY (US)

(73) Assignee: Enzo Biochem, Inc., New York, NY (US)

( * ) Notice: Subject to any disclaimer, the term of this patent is extended or adjusted under 35 U.S.C. 154(b) by 1735 days.

(21) Appl. No.: 11/175,884

(22) Filed: Jul. 6, 2005

(65) Prior Publication Data

US 2009/0191538 A1 Jul. 30, 2009

Related U.S. Application Data

(60) Provisional application No. 60/585,688, filed on Jul. 6, 2004.

(51) Int. Cl.
*C12Q 1/68* (2006.01)
(52) U.S. Cl. ....................................................... 435/6.1
(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. | |
| 4,711,955 A | 12/1987 | Ward et al. | |
| 4,755,458 A | 7/1988 | Rabbani et al. | |
| 5,130,238 A | 7/1992 | Malek et al. | |
| 5,241,060 A | 8/1993 | Engelhardt et al. | |
| 5,270,184 A | 12/1993 | Walker et al. | |
| 5,696,251 A | 12/1997 | Arnold, Jr. et al. | |
| 5,888,724 A | 3/1999 | Silverstein et al. | |
| 5,994,056 A | 11/1999 | Higuchi et al. | |
| 6,743,605 B1 | 6/2004 | Rabbani et al. | |
| 6,986,985 B1 | 1/2006 | Engelhardt et al. | |
| 2003/0225247 A1 | 12/2003 | Stavrianopoulos et al. | |
| 2005/0137388 A1 | 6/2005 | Rabbani et al. | |

OTHER PUBLICATIONS

ALTS Group, Human Papillomavirus Testing for Triage of Women With Cytologic Evidence of Low-Grade Squamous . . . , J. National Cancer Inst., 2000, 397-402, 92.
Anceschi et al., Multiple Primer Pairs Polymerase Chain Reaction for the Detection of Human Papillomavirus Types, J. Virol Methods, 1990, 59-66, 28.
Berger et al., Universal Bases for Hybridization, Replication and Chain Termination, Nucl Acids Res, 2000, 2911-2914, 28(15).
Bergstrom et al., Synthesis, Structure, and Deoxyribonucleic Acid Sequencing With a Universal Nucleoside . . . , J. Am. Chem. Soc. ,1995, 1201-1209, 117.
Bergstrom et al., Comparison of the Base Pairing Properties of a Series of Nitroazole Nucleobase Analogs in the . . . ,Nucl. Acids Res,1997,1935-1942, 25(10).
Bosch et al.,Prevalance of Human Papillomavirus in Cervical Cancer: a Worldwide Perspective, J Nat Cancer Inst,1995, 796-802, 87(11).
Brown et al., Synthesis and Duplex Stability of Oligonucleotides Containing Adenine-Guanine Analogues, Carbohydrate Res,1991,129-139, 216.
Digene, Digene HPV DNA Test Hybrid Capture II, catalog No. 5101-1096, 1997, 1-50.
Evander et al., A General Primer Pair for Amplification and Detection of Genital Human Papillomavirus Types, J Vir. Methods,1991, 239-250, 31.
Gregoire et al., Amplification of Human Papillomavirus DNA Sequences by Using Conserved Primers, J. Clin Microbiol., 1989, 2660-2665, 27(12).
Hughes et al., Managing Atypical Squamous Cells of undetermined Significance (ACUS): Human Papillomavirus Testing . . . ,Am J Obstet Gynecol, 2002, 396-403,186.
Hill et al., Polymerase Recognition of Synthetic Oligodeoxyribonucleotides Incorporating Degenerate Pyrimidine and Purine Bases, Proc. Natl. Acad. Sci USA, 1998,4258-4263, 95.
Huang et al., Human Papillomavirus Types 52 and 58 are Prevalent in Cervical Cancers from Chinese Women, Int J Cancer, 1997, 408-411, 70.
Jacobs et al., Distribution of 37 Mucosotropic HPV Types in Women With Cytologically Normal Cervical Smears . . . , Int J. Cancer, 2000, 221-227, 87.
Kahn et al., Molecular Cloning and Characterization of the DNA of a New Human Papillomavirus (HPV 30) from a Laryngeal Carcinoma, Int J Cancer,1986, 61-65, 37.
Kamiya et al.,In Vitro Replication Study of Modified Bases in ras Sequences, Chem Pharm Bull.,1992, 2792-2795, 40(10).
Kleter et al.,Development and Clinical Evaluation of a Highly Sensitive PCR-Reverse Hybridization Line Probe Assay . . . , J. Clin Microbiol,1999, 2508-2517, 37(8).
Kozume et al., Synthesis and Thermodynamic Stabilities of Damaged DNA Involving 8-Hydroxyguanine . . . ,Nucleosides & Nucleotides,1994,1517-1534,13(6&7).
Kong et al., Synthesis and Duplex Stability of Oligonucleotides Containing Cytosine-Thymine Analogues, Nucl. Acids Res.,1989, 10,373-10,383,17(24).
Konya et al., Additional Human Papillomavirus Types Detected by the Hybrid Capture Tube Test Among Samples from Women With . . . , J Clin Microbiol, 2000, 408-411, 38(1).
Kwok et al., Design and Use of Mismatched and Degenerate Primers, PCR Primer a Laboratory Manual, ed. by Dieffenbach and Dveksler, CSHL Press, 143-155, Plainview, NY.
Loakes et al., 5-Nitroindole as an Universal Base Analogue, Nucl. Acids Res.,1994 4039-4043, 22.
Loakes et al., Survey and Summary The Applications of Universal DNA Base Analogues, Nucl Acids Res, 2001, 2437-2447, 29(12).
Lorincz et al., Human Papillomavirus Infection of the Cervix: Relative Risk Associations of 15 Common Anogenital Types, Obstet and Gynecol,1992, 328-337, 79.
Lungu et al., Typing of Human Papillomaviruses by Polymerase Chain Reaction Amplification with L1 Consensus Primers and RFLP Analysis, Mol. Cell. Probes,1992,145-152, 6.
Manos et al., Use of Polymerase Chain Reaction Amplification for the Detection of Genital Human Papillomaviruses, Cancer Cells, 1989, 209-214, 7.

(Continued)

*Primary Examiner* — Christopher M. Babic
(74) *Attorney, Agent, or Firm* — Natalie Bogdanos, Esq.

(57) ABSTRACT

Compositions and methods for discriminately detecting the presence of a set of related genes from target organisms while avoiding detection of closely similar genes in non-target organisms. The present invention achieves this objective by a variety of novel nucleic acid constructs and methods. The nucleic acid constructs of the present invention are able to carry out this objective by virtue of the selected sequences of the compositions and by methods of use of such compositions.

165 Claims, 3 Drawing Sheets

OTHER PUBLICATIONS

Meyer et al., Association of Rare Human Papillomavirus Types with Genital Premalignant and Malignant Lesions, J Inf Dis,1998, 252-255,178.

Meyer et al., Distribution of HPV 53, HPV 73 and CP8304 in Genital Epithelial Lesions With Different Grades of Dysplasia, Int J Gynecol Cancer, 2001,198-204,11.

Rattray et al., Type-Specific Prevalence of Human Papillomavirus DNA Among Jamaican Colposcopy Patients, J. Inf Dis, 1996, 718-721, 173.

Tawheed et al., Characterization of Human Papillomavirus Type 66 From an Invasive Carcinoma of the Uterine Cervix, J. Clin Micro,1991, 2656-2660, 29(11).

Van Den Brule et al., General Primer-Mediated Polymerase Chain Reaction Permits the Detection of Sequences and Still Unsequenced Human . . . ,Int J. Cancer,1990, 644-649, 45.

Walboomers et al., Human Papillomavirus is a Necessary Cause of Invasive Cervical Cancer Worldwide, J Path,1999,12-19,189.

Zaccolo et al., An Approach to Random Mutagenesis of DNA Using Mixtures of Triphosphate Derivatives of Nucleoside Analogues, J. Mol. Biol,1996,589-603, 255.

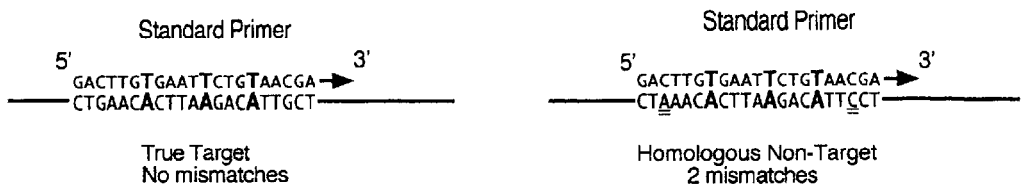

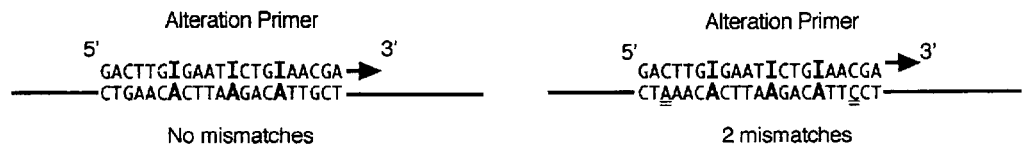

(1) Sequence alteration by substitution of Inosines for T's in Alteration Primer

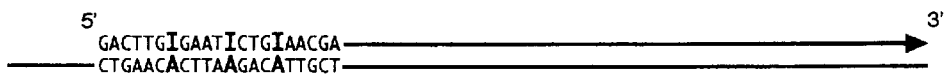

(2) Extension of Alteration Primer using true target as template

(3) Binding of second primer to extended Alteration Primer

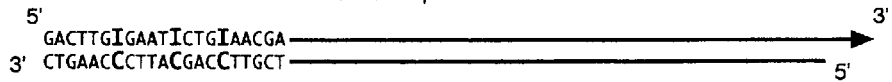

(4) Synthesis of complementary copy by extension of second primer + use of Alteration Primer as template

Complementary copy from step (4) above shows more discrimination compared to original non-target nucleic acid when using Discriminator Probes or Primers

```
GACTTGGGAATGCTGGAACGA                    GACTTGGGAATGCTGGAACGA
CTGAACCCTTACGACCTTGCT                    CTAAACACTTAAGACATTCCT

No mismatches                         Homologous Non-Target
                                              5 mismatches
```

Figure 1

(1) Binding to Target and Non-Target sequences by Alteration Primers

(A) Target sequence
No mismatches (B) Non-Target sequence
2 mismatches

(2) Extension of Alteration Primers

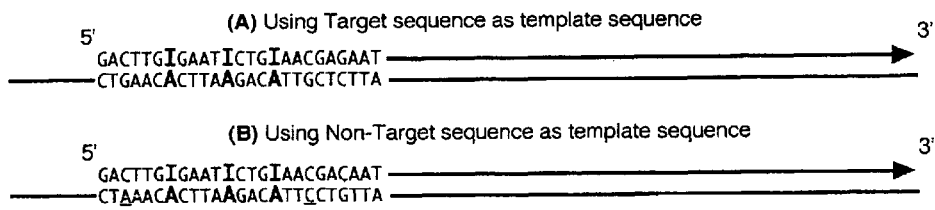

(3) Binding of reverse primers to extended Alteration Primers

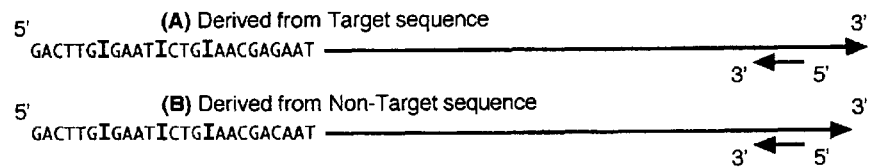

(4) Synthesis of complementary copy by extension of reverse primers

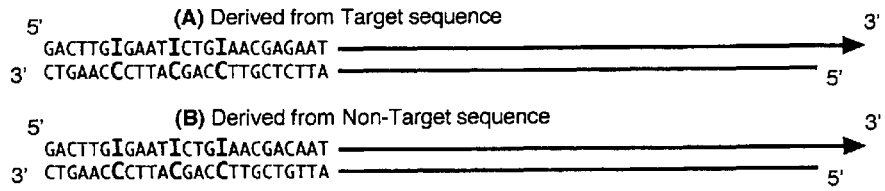

(5) Binding and extension of Discriminator Primers

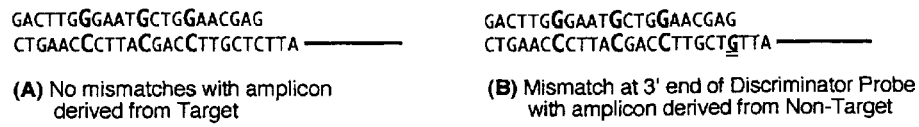

(A) No mismatches with amplicon derived from Target (B) Mismatch at 3' end of Discriminator Probe with amplicon derived from Non-Target

Figure 2

A         (1) Primer with stabilizer element binds to target with three mismatches
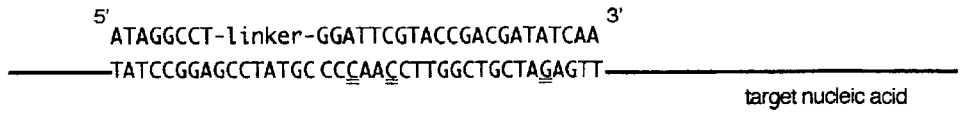
(2) Primer with stabilizer element is extended
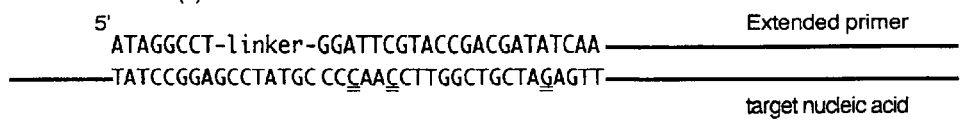
(3) Extended primer binds a second primer
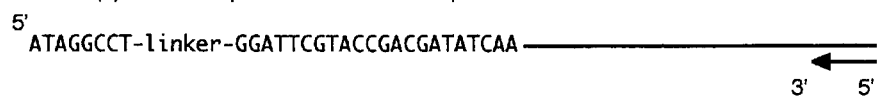
(4) Extended primer is used as a template by second primer
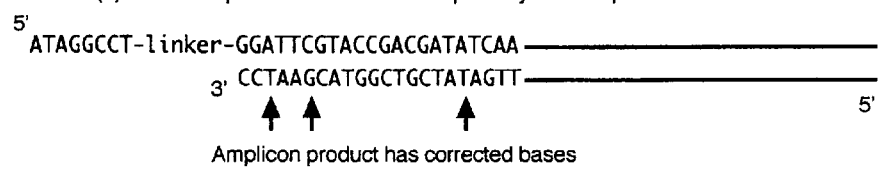
Amplicon product has corrected bases
Other Examples of primers with stabilizer elements
B
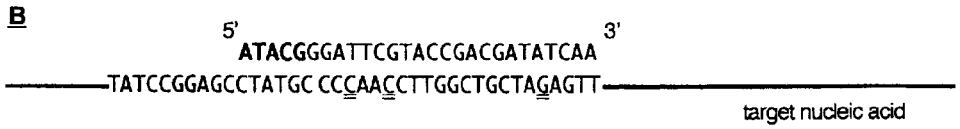
C
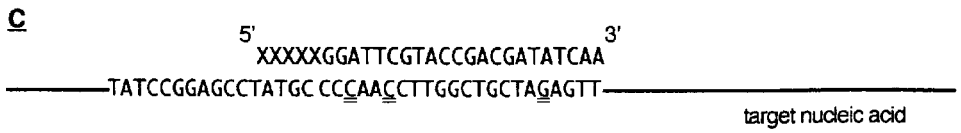
FIGURE 3

SELECTIVE DETECTION OF ONCOGENIC HPV

This application claims priority from Provisional Patent Application No. 60/585,688 filed on Jul. 6, 2004, entitled "Selective Detection of Oncogenic HPV." The content of the aforementioned patent application is hereby incorporated by reference, in its entirety.

BACKGROUND OF THE INVENTION

HPV Epidemiology

The correlation between the potential for development of cervical carcinoma and the presence of Human Papilloma Virus (HPV) infection has become well established. For example, in a worldwide survey of cervical carcinomas, 93% of the specimens showed evidence of the presence of HPV sequences (Bosch et al., 1995 J Nat Cancer Inst 87; 796-802). Since PCR primers used for that study were derived from the L1 region, some of these specimens were retested with primers from other regions and a rate of 99.7% was reached (Walboomers et al. 1999 J Path 189; 12-19) demonstrating that in all likelihood the presence of HPV is a necessary condition for development of cervical carcinoma.

However, although physically and phylogenetically related, HPV does not represent a homogeneous population of viruses; there are a large number of different HPV types that differ from each other with regard to nucleic acid homology and properties such as tissue tropism and oncogenic potential. For instance, certain HPV types can be grouped together on the ability to infect genital-mucosa tissues and another group of HPV types can be formed that is linked together by the ability to carry out cutaneous infections. For the genital-mucosal trophic HPV, a survey of which particular HPV types are present in specimens with various levels of tumor progression allows risk assessment for cervical carcinoma to be carried out for any given HPV type. Thus, a demarcation has been drawn between genital-mucosa HPV types that are unlikely to lead to an oncogenic state (the Low Risk group) and HPV types that exhibit a significant risk of tumor progression (the Medium and High Risk groups). This is more than of academic interest since the presence of the Medium or High Risk group can have prognostic value that can direct the treatment of the patient. Various papers have been written concerning the value of HPV testing with regard to the nature of the patient, the nature of a specimen and the particular type of HPV that is identified as being present.

For instance, the HPV Hybrid Capture II test, a commercially available FDA approved assay (Digene, Inc. Rockville, Md.) provides two cocktails of RNA probes: a Low Risk group for detection of HPV 6, 11, 42, 43 and 44 and a High Risk group for detection of HPV 16, 18, 31, 33, 35, 39, 45, 51, 52, 56, 58, 59 and 68. Signal generation is carried out by labeled antibodies that have specificity for RNA/DNA hybrids. The presence or absence of the low risk group did not seem to generate information that could be used to alter the treatment of patients whereas positive results from the High Risk group did have diagnostic and prognostic value. As such, this test was later modified and approved by the FDA such that only the cocktail for the High Risk group could be used. This method suffers from the need to use a large number of separate probes simultaneously (13 in the High Risk cocktail alone). Early on it was recognized that the majority of HPV positive cancers seemed to have either HPV 16 or HPV 18, while each of the other HPV types seemed to be present in a much smaller number of cases. Individually, each of these other types is a "minor" causative agent, but as a group they can collectively represent a major risk factor in the likelihood of development of cervical carcinoma. As such, the addition of other HPV types besides 16 and 18 can add incremental levels of sensitivity of detection of oncogenic HPV.

However, the use of a probe cocktail that contains so many individual species has the result that the concentration of each individual probe has to be maintained at a sufficient level that it can drive the reaction for hybridization with its appropriate target. The presence of such an increase in complexity of sequence information in the probe mix and the presence of such a heightened amount of probe in the hybridization mixture can lead to cross-reaction with other HFV types and non-specific binding. This may explain why the High Risk cocktail exhibited signals with HPV 6, 11, 40, 42, 53, 55, 70 and MM8, HPV types that are not considered to be associated with cancer development (ALTS Group 2000 J. National Cancer Inst. 92; 397-402; Hughes et al. 2002 Am J Obstet Gynecol 186; 396-403). Thus, the increased breadth that was implemented in this assay may also have conveyed a negative quality of a broader spectrum of sensitivity to non-oncogenic HPV as well.

Amplified Assays

Sensitivity and selectivity can also be enhanced by the use of nucleic acid amplification technology. Exponential amplification as first exemplified in PCR by Mullis et al., (U.S. Pat. No. 4,683,195 hereby incorporated by reference) is achieved by the use of at least one pair of primers: a forward primer and a reverse primer. These primers can be defined in various ways. For instance, in terms of a double stranded target molecule, a forward primer comprises sequences complementary to one strand and a reverse primer comprises sequences complementary to the other strand. In terms of a single strand, a forward primer comprises sequences complementary to one region of a target nucleic acid strand and the reverse primer comprises sequences identical to a different region of the target nucleic acid strand. Due to this arrangement, a forward primer binds to a complementary target molecule followed by extension using the target as a template, thereby providing a copy of a portion of the target molecule (the forward reaction). The reverse primer uses this copy as a template for another binding and extension reaction (the reverse reaction) thereby providing another copy that can be used by a forward primer and so on. Thus, a series of forward and reverse copying reactions provides amplification of the portion of nucleic acid sequences between the binding sites for the forward and reverse primers.

Type Specific Amplification

Exploiting this methodology, selective amplification of various HPV types has been carried out by the design of PCR primer pairs that are specific for each type of HPV. Conditions can be established such that amplification takes place only when a particular HPV target is present in a specimen. The resultant product can then be evaluated by the presence of an amplification event itself as judged by gel analysis or by incorporation. Further specificity can be insured by using type specific probes and detecting the presence of individual HPV sequences in the amplified products.

This method has practicality if only a limited number of types are being evaluated; for instance, if only the presence of HPV 16 and HPV 18 are being ascertained. However, as described above, inclusion of more HPV types may be needed to provide more sensitivity of HPV detection. Thus to generate the equivalency of the assay above, 13 separate primer pairs would be needed. Therefore, this method has the limitation that if individual amplifications are carried out, a large number of different type specific reactions are required to cover each oncogenic type that is desired to be included in an assay. This decreases the amount of sample available for each reaction and increases the amount of reagents and supplies for the cost of the test. As such, multiplex amplification is usually done with a more limited number of different potential targets since the addition of numerous individual primers of each HPV type increases the total amount of primers in the reaction mixture thereby encouraging non-specific priming events. An example of this is a multiplex amplification of 6, 11, 16 and 18 (Anceschi et al., 1990 J. Virol Methods 28; 59-66). As described above for probe specific assays, this method is also self-defining in that the primers are designed to be capable of only amplifying a particular HPV type and other HPV types that may be present are not amplification targets.

Consensus Primers for Amplified Assays

Systems for the generic amplification of multiple species of HPV have also been carried out by a number of groups. As described above, it has been used to establish the correlation between HPV infection and the development of cervical cancer. Although the definition of different types of HPV is based on differences in sequences in homology, the sequence variation is not homogeneous over the length of the viral genome and two particular genes, E1 and L1, tend to be more conserved than other segments. Although no particular sequence is completely preserved within the genomes of all the various HPV types, relatively conserved sequences can be found. A consensus sequence can be used for forward and reverse primers and amplification carried out under conditions where a certain level of mismatches is tolerated (van den Brule et al., 1990 Int J. Cancer 45; 644-649). Another example was recently presented by Kleter et al., 1999 (J Clin Micro 37; 2508-2517) which used sequences derived from HPV 16 as primers. This system was able to amplify HPV samples from types that had as many as 4 mismatches by using relatively non-stringent conditions of 52° C. as an annealing temperature. Alternatively, to maximize the spectrum of HPV types that can be used as substrates, the primers can be designed such that at variable positions, an indiscriminate base such as Inosine (Gregoire et al., 1989 J. Clin Micro. 27; 2660-2665) or a mixture of bases can be used (Manos et al., 1989 Cancer Cells 7; 209-214). Even with this design, there may still be a certain number of mismatches due to the diversity of sequences in different HPV types but conditions can be adopted such that amplification still takes place. Consideration of which particular types are the targets can also affect the primer design and amplification conditions. For instance, the GP 5,6 consensus primers used by van der Brule et al, 1990 (op. cit.) were designed to have no more than two mismatches with genital mucosa types 6, 11, 16, 18 and 31 but were allowed to have numerous mismatches with cutaneous varieties of HPV (van den Brule et al., 1990 Int J. Cancer 45; 644-649). A similar strategy was employed by Evander and Wadell (1991 J Vir. Methods 31; 239-250) where genital mucosa types 6, 11, 16, 18, 31 and 33 had a maximum of three mismatches and amplified efficiently with a 60° C. annealing temperature. As the annealing temperature was lowered to 55° C., HPV types 13 and 30 which are associated with oral and genital/oral tropisms respectively were efficiently amplified and faint bands were seen for cutaneous HPV types 2, 3 and 7. Thus the selectivity of the amplification reaction could be adjusted for the particular breadth that was desired.

As expected, the design of such general primers has allowed the amplification of the HPV types whose sequences were used to design these primers. However, the generality of these primers was also shown by the ability to amplify related HPV types which had been previously isolated and characterized but had not been sequenced at the time the primers were developed. For instance, in the paper by Evander and Wadell (supra), their primers were able to efficiently amplify HPV 13 and HPV 30 even though the sequences for these types only became available years afterwards. Amplification with consensus HPV primers has the advantage that its relative insensitivity to the nature of the particular HPV type in a specimen allows epidemiological surveys to be carried out without delineating which particular HPVs are defined as targets. However, due to the general nature of these amplification systems, the presence of an amplified product only generates the information that there was HPV in the specimen being tested. For epidemiological surveys or other purposes, the knowledge of the particular type of HPV has to be ascertained by additional analytical methods. For example, the amplification products can be used for RFLP analysis to identify characteristic patterns of restriction enzyme digestion (Lungo et al., 1992 Mol. Cell. Probes 6; 145-152). The amplified material can also be hybridized with type specific probes in a manner similar to that used for unamplified HPV genomic nucleic acids. For example, Jacobs et al., (2000 Int J. Cancer 87; 221-227) provides a list of 37 different probe sequences that can be used to identify any one of 37 different HPV types that could be amplified by the GP5+ GP6+ pair of consensus primers. Or if there is still material remaining, consensus positive specimens can be used in a secondary round of amplification with type specific primers.

The general nature of these amplification systems may be useful for determining which particular HPV types are associated with the malignancy state. This may then be used for the design of assays for selected HPV types such as the system described previously for Digene. For example, the use of consensus sequence primer amplification revealed that although HPV 45 is relatively rare in the United States (Lorincz et al., 1992 Obstet and Gynecol 79; 328-337), it had a high prevalence rate in samples from patients with severe dysplasia in Jamaica (Rattrey et al., 1996 J. Inf Dis 173; 713-721). Furthermore, although these generic systems are derived from comparisons between different sequences of known HPV types, the open nature of its amplification doesn't relegate it to only these types and consequently, novel HPV types are also candidates for amplification and detection. These novel types can then be isolated and characterized further. In contrast, a probe specific type of assay such as the one by Digene can detect multiple HPV types but it is not open-ended since the results are shaped by the decision of which particular HPV types are included in the probe cocktail.

As described previously, detecting the presence of HPV in general is not adequate since the nature of the particular HPV type may have a bearing upon the course of treatment. In one approach to this, Silverstein et al., (U.S. Pat. No. 5,888,724) have disclosed a method for the specific amplification and detection of oncogenic HPV. Primers were designed such that they had high homology with oncogenic types of HPV and low homology with types that were considered to have a low risk of oncogenic potential (HPV 6, 11, 30, 32, 34, 42 and 53). However, this assay has the limitation that their disclosure specifically points out that the sequences of two other HPV types, HPV 51 and HPV 52, were sufficiently different that they would not be amplified or detected in their system. Thus, although both of these types are usually considered to be bona fide members of the high risk group, the assay disclosed by Silverstein et al., has been designed to ignore the presence of two types of HPV that are considered to have high oncogenic potential. Also, the prevalence of different HPV types in cancers may have geographical differences. For instance, HPV 52 together with HPV 58 was seen to actually have a higher representation in cervical carcinomas than HPV 16 and HPV 18 in a survey of Chinese women (Huang et al., Int J Cancer 70; 408-411), thus a clinically important variety of HPV (HPV 52) was ignored by the Silverstein assay.

Additionally, the primers used for this method were only 16-mers. As such, the conditions used for amplification included an annealing step of 42° C. (near the Tm of the primers) followed by an extension step of 72° C. (where the thermostable polymerase can function efficiently). Thus, during the transition from the annealing to the extension temperatures, this process depends upon primers being extended before they can separate from their templates. However, due to the inefficiency of the polymerase at lower temperatures, it is likely that there are many instances of primers annealed to their appropriate target who are denatured before an extension event can go forward thereby reducing the efficiency of amplification. Thus, the method of Silverstein has the limitation that it lacks sufficient breadth to generate signals from a clinically significant HPV type and relies on short thermolabile primers to carry out their process.

The breadth of inclusivity or non-inclusivity of an assay can influence its utility or potential use. Thus, as described above, the Silverstein method of assaying for oncogenic types of HPV suffers from an inability to recognize certain oncogenic types of HPV that are clinically important. As described previously, in addition to HPV 16 and 18, HPV 45, 52 and 58 are oncogenic HPVs that would be important in being recognized by a clinical assay. On the other hand, there can be signal generation from HPV types that were not intended as targets. For instance, as described previously, the Digene assay inadvertently generated signals from some HPV types that were not included in the High Risk probe mixture (ALTS group 2000, op. cit. and Konya et al., J Clin Micro 38; 408-411). This is especially problematic with a cross reaction with HPV 6 since it is a highly prevalent HPV type that may be present in high numbers in a clinical specimen but is unlikely to lead to an oncogenic event. In some cases, due to their rarity and the presence of an oncogenic potential, the presence of signal generation would not materially affect the worth of the assay. An example of this would be HPV 30 which is among the unintentional targets of the Digene assay. Due to its rarity, it's not usually included among the group of oncogenic types but at the same time, it should be noted that it was originally isolated from a carcinoma (Kahn et al., 1986 Int J Cancer 37; 61-65).

The problem with these rare types is that the limited available data makes it difficult to properly assign risk assessments for these types. For example, the literature contains numerous articles where HPV 66 is included as a member of the High Risk group and other papers have it listed with the Low Risk group. HPV 66 should probably be included with the High Risk groups since the original isolation was from an invasive carcinoma (Tawhed et al., 1991 J. Clin Micro 29; 2656-2660). An attempt to study the oncogenic potential of some of these other types was carried out by Meyer et al., (1998 J Inf Dis 178; 252-255) where, among the members shown above, they concluded that MM4 and HPV 66 should probably be considered High Risk types and HPV 53 should be included among the Low Risk group despite its phylogenetic kinship with other oncogenic types. A followup study by this group (Meyer et al., 2001 Int J Gynecol Cancer 11; 198) also concluded that HPV 53 was unlikely to be oncogenic. This may be problematic in the Digene test since HPV 53 has been shown to be one of the types that is inadvertently picked up by the Digene assay (ALTS group 2000, op. cit. and Konya et al., op.cit.).

SUMMARY OF THE INVENTION

The present invention describes various methods and compositions for discriminately detecting the presence of a set of related genes from target organisms while avoiding the detection of closely similar genes in non-target organisms. This objective is achieved by a variety of novel nucleic acid constructs and methods. The nucleic acid constructs accomplish this by virtue of the selected sequences of the compositions and by methods of use of such compositions. Methods include the selective hybridization, selective extension and selective amplification of novel nucleic acid constructs.

BRIEF DESCRIPTION OF THE DRAWINGS

FIG. 1 is an illustration of the use of an Alteration Primer to reduce spurious amplification of a non-target sequence by increasing the number of mismatches with a Discrimination Primer.

FIG. 2 is an illustration of the use of an Alteration Primer to reduce spurious amplification of a non-target sequence by means of a 3' mismatch with a Discriminator Primer.

FIG. 3 is illustrations of primers with stabilizer elements comprising nucleic acids that are involved in primer binding but are not used as templates for nucleic acid synthesis. In Panel A, the stabilizer element is unable to be used as a template due to the presence of a non-nucleotide linker joining two sequences. In Panel B, the stabilizer element is unable to be used as a template due to the sequence comprising peptide-nucleic acid analogs in the stabilizer element. In Panel C, the stabilizer element is unable to be used as a template due to the use of universal bases in the stabilizer element.

DETAILED DESCRIPTION OF THE INVENTION

The present invention provides methods and compositions that can discriminately detect the presence of a set of related genes from target organisms while avoiding detection of closely similar genes in non-target organisms. The present invention achieves this objective by a variety of novel nucleic acid constructs and methods. The nucleic acid constructs of the present invention are able to carry out this objective by virtue of the selected sequences of the compositions and by methods of use of such compositions.

The present invention discloses sets of nucleic acid constructs where at least one nucleic acid construct can recognize at least two desirable targets while avoiding the detection of similar but undesirable sequences. Any of the following approaches can be used alone or in combination to achieve this discrimination:

1) selective hybridization of novel nucleic acid constructs where the nucleic acid constructs can comprise:
 a) unique sequences from one of the desirable targets;
 b) chimeric sequences that are a composite of the sequences of the targets;
 c) a set of nucleic acid constructs with permutations at selected sites in unique or chimeric sequences or
 d) unique, chimeric or permutational sequences that comprise one or more degenerate or universal nucleotide analogues.

These various means of choosing sequences enable the design of nucleic acid constructs that have sufficient breadth to hybridize with more than one target nucleic acid while still limiting the ability to form hybrids with similar sequences that are not targets.

2) selective extension of novel nucleic acid constructs.

The ability of a 3' end of a construct to use a nucleic acid from a particular target as a template for an extension event can be used to provide discrimination with the construct acting as a probe/primer. This may be used alone or in combination with selective hybridization. Strand extension can be carried out under various conditions such as:

a) a single nucleotide is provided and it is incorporated in the presence of the proper target template and does not undergo incorporation in the presence of related non-target sequences;

b) limited extension where at least one of the 4 nucleotides is omitted;

c) limited extension where at least one of the nucleotides is a chain terminator (for instance a dideoxynucleotide or an acyclic nucleotide);

d) full extension where all four nucleotides are provided and the ability to be efficiently extended is a necessity for a series of amplification reactions to take place; and e) full extension where all four nucleotides are provided and at least one modified nucleotide or nucleotide analogue is provided such that nucleic acid extension products are created that have different Tm's from the original target nucleic acid further separating them from related non-target sequences.

A single round of extension can be carried out using the novel constructs of the present invention or if desired multiple rounds of extension can be carried out to increase the amount of signal generation.

3) selective amplification with novel nucleic acid constructs.

As described previously, exponential amplification can be carried out by the use of at least two primers: a forward primer and a reverse primer. Extension of a forward primer with a target nucleic acid strand generates a complementary copy (a first copy). This product can then be used in turn as a template for extension of a reverse primer, thereby generating a second copy that comprises sequences identical to a portion of the initial target strand. This second copy can then be used for binding and extension of another forward primer and so on. When used as primers for exponential amplification, the selectivity of binding and primer extension of the constructs of the present invention can also imbue amplification with selectivity while at the same time enjoying multivalent capability.

4) In addition, novel compositions and methods of use are provided that can improve discrimination between target and non-target detection by blocking the ability of non-target sequences to bind to probes or primers.

In general, the nucleic acid constructs of the present invention may find use as probes, primers or probe/primers. In the present invention, primers are extendable under the proper circumstances whereas probes are either incapable of extension or are used in a context where they remain unextended. In the present invention, extension can take place by the addition of one or more nucleotides in a sequential manner as exemplified by a polymerase catalyzed reaction or extension can take place by the addition of an oligonucleotide or polynucleotide as exemplified by a ligase catalyzed reaction. With regard to probes, discrimination is dependent upon the ability to hybridize or remain hybridized to the appropriate target sequence without substantially hybridizing to similar non-target sequences. In the case of primers, discrimination can be dependent upon the ability to hybridize to a primer binding site, the ability to be extended after binding or by a combination of both properties. Primers may be used for a single series of extension events or as part of a multiple series (i.e. amplification). The nucleic acid constructs of the present invention can comprise normal nucleotides, modified nucleotides or nucleotide analogues, either alone or in various combinations. The modified nucleotides or nucleotide analogues may imbue the nucleic acid construct with desirable properties.

Examples of such properties can include but not be limited to signal generation, capture ability, alterations of sequence specificity and alterations of Tm's. The nucleic acid construct may be comprised of a normal sugar phosphate backbone or the nucleic acid construct can be partially or completely comprised of analogues that may serve the same function as a sugar phosphate backbone. For instance, peptide nucleic acids (PNAs) have normal A, C, T and G bases but they are linked together through a totally artificial peptide backbone without either sugar or phosphate groups. Due to the design of the peptide backbone, the bases can still participate in sequence specific base pairing with the appropriate sequences in a normal nucleic acid target, forming a hybrid between the PNA and the nucleic acid. Oligonucleotides made with PNA analogues enjoy an advantage in that they are more stable than normal oligonucleotides with the same sequences. On the other hand, only a limited length may be used due to solubility considerations and they can not be used as templates in copying reactions. Other examples of modified backbones in nucleic acid constructs that may find use with the present invention can include phosphonates and phosphorothionates. Another example is the synthesis of oligonucleotides with abasic sites that utilize a so-called "spacer group" to preserve the appropriate structure when the oligonucleotide is hybridized to a complementary acid (U.S. Pat. No. 5,696,251 incorporated herein by reference). Increased stability may also be provided by alterations of the bases. For instance, Glen Research (Sterling, Va.) offer phosphoramidites for 2-amino-A, 5-methyl-C, C-5 propynyl-C and C-5 propynyl-U nucleotide analogues, all of which demonstrate enhanced binding characteristics compared to their normal counterparts. In another example, Engelhardt et al. (U.S. patent application Ser. No. 09/302,816 hereby incorporated by reference) have described how the addition of an Ethidium Bromide moiety can increase the binding of an oligonucleotide to its complementary sequence. In contrast to the PNA analogues, these base analogues do not have problems with either solubility or their ability to be used as templates.

In the present invention, useful properties are derived from the use of nucleotide analogues. These can be included as part of primers or probes that bind to appropriate nucleic acid targets or they can be incorporated as nucleotide triphosphates during nucleic acid synthesis. One class of analogues that may find use with present invention are the nucleotide analogues that provide increased stability of binding. As described above, a second class of analogues that may find use with the present invention are analogues that exhibit reduced stringency in base pairing requirements, i.e. universal and degenerate bases. Examples of the former can include but not be limited to 5-nitro-indole (Loakes, D. and Brown, D. M. 1994 Nucl. Acids Res. 22; 4039-4043) and 3-nitro-pyrrole (Bergstrom et al., 1995 J. Am. Chem. Soc. 117; 1201-1209). Examples of the latter can include the "P" and "K" nucleotide analogues (Kong et al., 1989 Nucl. Acids Res. 17; 10, 373-10,383). Use of such nucleotide analogues have been referred to previously in U.S. Patent Application No. 20030225247 hereby incorporated by reference.

In some contexts, the nucleic acid constructs are unlabeled whereas for other purposes detectable labels may be included. The detectable labels may be used for signal generation, provide for capture of nucleic acid complexes through ligand interactions or convey any other useful property. In addition to the sequences that are homologous to the target, other sequences may be included in the nucleic acid construct that convey useful properties. For instance, these may be sequences used for capture, detection, or amplification. Examples of the last case are the inclusion of an RNA promoter sequence for NASBA (Malek et al. in U.S. Pat. No. 5,130,238) or a restriction enzyme recognition site as used in SDA amplifications (Walker et al. in U.S. Pat. No. 5,270,184) both of which are incorporated by reference.

In one aspect of the present invention, nucleic acid constructs are disclosed that generate signals from a number of different oncogenic HPVs and substantially do not lead to signal generation from varieties of HPV that do not entail significant risk of progression to a malignant state. In contrast to prior art that either used: a) type specific sequences that recognize discrete individual HPV types; or b) generic sequences that broadly recognize multiple HPV types without regard for their oncogenic potential, the present invention discloses sequences that simultaneously recognize more than one oncogenic HPV type while retaining discrimination against selected non-oncogenic HPV types.

Thus, although previous art was able to provide both selectivity towards the detection of only oncogenic types of HPV and at the same time a breadth in the number of the different oncogenic types by the use of a large set of type specific primers and probes, the use of the methods and compositions of the present invention is able to convey the same abilities while requiring a lower number of probes and/or primers. Also, in contrast to prior art, the present invention discloses novel sequences that are sufficiently conserved that they are appropriate for designing nucleic acid constructs capable of multivalent amplification and/or detection of HPV 16, 18, 31, 33, 35, 39, 45, 51, 52, 56, 58, 59 and 68 (all of the HPV types that are included in an FDA approved kit for the detection of High Risk HPV) yet sufficiently discrete that they can distinguish between the members of the foregoing group and the most common non-oncogenic types, HPV 6 and 11. These constructs may also be designed to be capable of discriminating against less common non-oncogenic types such as HPV 42, 43 and 44 (the other HPV types that were included in the FDA approved kit for the detection of Low Risk HPV).

For nucleic acids, the ability of a nucleic acid to bind to another nucleic acid is dependent upon the complementarity between the two nucleic acids, i.e. the number of matches and mismatches in their base sequences. The present invention discloses sequences that have higher affinity for a group of selected oncogenic HPV types (targets) than a selected group of Low Risk HPV types (non-targets) thereby allowing differential detection of the selected targets. Since the degree of matching of a probe or primer sequence within either the target or non-target groups can vary between different members, differentiation of the groups takes place when the member of the selected target group with the lowest number of matches with the homologous probe or primer sequence has a higher number of matches than the member of the non-target group with the highest number of matches with the homologous probe or primer sequence. For instance, in distinguishing between a target group that comprises HPV types A, B and C and a non-target group that comprises HPV types D, E, and F, a selected sequence Q can distinguish between the included and non-included groups when the lowest number of matches of the selected sequence Q with the homologous sequence in A, B or C is equal to an integer "n" and the highest number of matches of the sequence Q with the homologous sequence in D, E or F is an integer "x" where "x" is equal to or less than an integer "n−1". The larger the difference between "n" (the lowest number of matches with A, B or C) and "x" (the highest number of matches with D, E or F), the better the sequence is able to discriminate between the two groups. By manipulating the length of the probes or primers and the conditions of annealing (usually salt and temperature) the stability of perfectly matched and varying degrees of imperfectly matched double-stranded hybrids can be dictated.

The sites of the mismatches can also have different effects depending upon whether a particular sequence is being used as a primer or a probe. For instance, mismatches at the ends of a probe have only a slight effect on thermostability and mismatches in the middle have more consequences. On the other hand, since the ability to be extended is the essence of functionality for primers, mismatches at the 3' end acquire more critical importance than interior mismatches for primer sequences.

The present invention discloses a number of sequences homologous to groups of HPV types that when used in various combinations can constitute assays that recognize a variety of oncogenic HPV types, while discriminating against non-oncogenic HPV types. The design of the primers and probes can be derived from the following categories:

a) a probe (or primer) sequence that is perfectly homologous to an oncogenic HPV sequence and is capable of efficiently hybridizing (and/or extending) with more than one oncogenic HPV type target;

b) a chimeric probe (or primer) sequence that has imperfect homology with all of the members of a group of HPV types but is sufficiently homologous that it is capable of efficiently hybridizing (and/or extending) with more than one oncogenic HPV type;

c) a set of probe (or primer) sequences that comprise permutational base assignments at selected sites such that efficient hybridizing (and/or extending) may be carried out with more than one oncogenic HPV type; and d) a probe (or primer) sequence that comprises nucleotide analogues such as "degenerate bases" that are capable of base pairing with more than one particular base, and/or "universal bases" that substantially lack base specificity.

Examples of degenerate bases can include but not be limited to natural degenerate bases such as Inosine and artificial degenerate bases such as 8-oxo-guanidine, "P" base analogue (Lin and Brown 1989 Nucl Acids Res 17; 10,373-10,383) and "K" base analogue (Brown and Lin 1991 Carbohydrate Res 216; 129-139). Inosine can base pair with all 4 bases with varying degrees of stability dI:dC>dI:dA>dI:dG>dI:dT (Kawase et al., 1994 Nucleosides Nucleotides 13; 1517-1534). The other analogues have more limited abilities. 8-oxo-guanidine undergoes base pairing with either A or C (Zaccolo et al., 1996 J. Mol. Biol. 255; 589-603); the "P" base analogue can undergo complementary base pairing with either A or G and the "K" base can base pair with either C or T (Bergstrom et al., 1997 Nucl. Acids Res. 25; 1935-1942). Examples of "universal bases" can include abasic nucleotides that lack any particular base identity. Other "universal bases" have also been synthesized that lack a specificity for base pairing, but a moiety attached to the sugar groups can contribute base stacking that augments the stability. For a review of chimeric, permutational and degenerate designs of primers, see Kwok et al., "Design and Use of Mismatched and Degenerate Primers" pp 143-155 in "PCR Primer, a Laboratory Manual" ed. by Dieffenbach and Dveksler, CSHL Press, Plainview, N.Y. 1995; Berger et al., 2000 Nucl Acids Res 28; 2911-2914; Hill et al. 1998 Proc. Nat. Acad. Sci. USA 95; 4258-4263 and Loakes 2001 Nucl Acids Res 29; 2437-2447, all of which are incorporated by reference.

Examples are given of novel constructs that are sufficiently broad that they are homologous to multiple target types yet are sufficiently narrow that they can discriminate against other undesirable HPV types. Due to phylogenetical considerations, these sequences can loosely be collected together as part of an HPV 16 group, an HPV 18 group and an HPV 51/56 group. The members of each of these groups can in turn be further categorized as subgroups. For instance, the HPV 16 group can be divided into one group comprising HPV 16, 33, 52 and 58 and a second group comprising HPV 31 and HPV 35. Similarly, the HPV 18 group can be divided into one subgroup comprising HPV 18, 45 and 59 and a second subgroup comprising HPV 39 and 68. Some of the disclosed sequences of an HPV group vary from each other such that a sequence is chosen from each subgroup in order that all members of the group are covered with minimal mismatching. In other cases, the sequences are sufficiently conserved such that a sequence is shared by both subgroups. Lastly, a disclosed sequence can be shared by more than one group. For instance a sequence can be selected that is sufficiently conserved that it is present in the HPV 18 group and the HPV 51/56 group while at the same time remaining substantially different from the homologous sequences in non-oncogenic HPV types.

The use of primers or nucleic acid constructs that are specific for the oncogenic variety of HPV should also improve the efficiency of detection. For instance, when two different types of HPV are present in a sample, disparate representation of each type may result in preferential amplification by consensus primers of only one type and the absence of evidence of the presence of the other type. This was shown in a study comparing amplification by two different consensus primers, where a clinical sample showed the presence of only HPV 16 after amplification with the MYO9/MY11 primers and only the presence of HPV 31 after amplification by SPF1/SPF2 primers (Kleter et al., 1999 J. Clin Micro 37; 2508-2517). This apparent discordancy was investigated further by the use of type specific primers that revealed the simultaneous presence of both HPV 16 and HPV 31 in the specimen. Thus each of the consensus primer sets missed one of the types in the mixed infection sample probably due to a competitive suppression mechanism. However, when the type-specific amplification was used instead, there was a lack of competition and this allowed the individual type specific amplifications to efficiently generate amplicons from each type. Although in the case cited above, it was a case of one oncogenic HPV type masking the presence of another oncogenic HPV type, competitive suppression by a non-oncogenic variety of HPV would be much more problematic. Thus, one of the benefits of the present invention would be that the presence of non-oncogenic HPVs in a mixed infection clinical specimen should not be substantially competitive with an oncogenic variety that may also be present.

Thus, to provide appropriate signal generation from the multiple oncogenic HPV types that are likely to be encountered in clinical specimens, an assay should at least be able to identify the presence of High Risk types HPV 16, 18, 45, 52 and 58. To enjoy a more complete coverage of oncogenic HPVs, it may also be desirable that the assay include other High Risk types such as those included in the FDA approved High Risk assay including HPV 31, 33, 35, 39, 51, 56, 59 and 68. At the same time, it is a desire of the present invention that the assay not generate any substantial signal from common non-oncogenic HPV types such as HPV 6 and 11. As described previously, the sequences used in the assay may also be designed to lack homology with other non-oncogenic HPV types such as those included in the FDA approved HPV Low Risk assay as well.

Reactivity with some other HPV types that are phylogenetically related to the oncogenic HPVs described above may or may not be desirable, depending upon their frequency of occurrence and their oncogenic potential. For example, coverage of HPV 66 and/or HPV 70 may improve the utility of an oncogenic HPV assay. As described above, some of this data has been accumulated, but in other cases their relative uncommonness has hindered estimation of risk factors. Since this is a still unsettled area, research is continuing on accumulating data for assignments of risk assessments. If desired, the particular sequences used as primers or probes can then be altered to either cover or avoid such types. Also, if another HPV type is desired to be added to the detectability of the assay, but it is phylogenetically too dissimilar, a separate probe or primer may be designed for the purposes of including this type. On the other hand, although it may be beneficial to detect an oncogenic HPV that is rarely encountered in a clinical specimen, the inability to detect their presence may have only limited impact on the utility of the assay due to their uncommon nature.

The sequences of the present invention offer suitable regions that can be used for the design of probes and primers that can carry out amplification and/or detection of multiple oncogenic types. There is flexibility in the choice of the specific sequences chosen from these segments depending upon the conditions that are intended to be used. For instance, for detection using multiple probes or a multiplex amplification, the sequences may be designed such that one set of conditions will be suitable for all of the various primers or probes that are used in combination.

Also, it should be pointed out that when using a pair of primers for amplification purposes, both primers may be chosen from the sequences of the present invention for the ability to selectively be extended with oncogenic HPV types as template targets. On the other hand, selective amplification can also be carried out if one primer is a selective primer and the other primer has a wider range of targets. Thus, specific amplification of oncogenic HPVs can still be maintained where a first primer is selectively extended only when an oncogenic HPV is a template and a second primer is capable of using both oncogenic and non-oncogenic HPVs as templates. As such, it is also considered to be part of the present invention that oncogenic HPV can be selectively amplified exponentially by a pair of primers where a first primer is an oncogenic HPV specific sequence and a second primer is chosen from HPV consensus primers that have been described in the literature. Conversely, type specific amplification can also be carried out by a pair of primers where one primer is selective for an individual HPV type and the second primer has a broader range of targets. For instance, these second primers can utilize oncogenic HPVs, mucoso-genital HPVs or HPVs in general, as templates. The use of a pair of primers where there are differences in specificity may be used in other ways as well. For instance, if a first primer is able to be extended using A, B, C and D as target templates but cannot use the nucleic acids sequences from organisms E or F and a second primer is able to be extended using C, D, E and F but cannot use the nucleic acids sequences from organisms A or B, an amplification system that depends upon extension of each primer will only be able to efficiently amplify the nucleic acid sequences from organisms that are shared by each of the primers, i.e. organisms C and D. In essence, the least common denominator defines the pool of templates that will be preferentially or efficiently amplified. Thus, for the example of HPV detection, if a first primer is able to extend a number of desirable oncogenic HPV types but also uses HPV 6 as a template and a second primer is able to extend the same desirable oncogenic HPV types but also can use HPV 42 as a template, conditions can easily be designed where only the desirable oncogenic HPV types are amplified without either HPV 6 or HPV 42 undergoing any appreciable amplification.

Amplification where the specificity is a result of the combined ability of the primers rather than the individual primers can be used in many other systems besides HPV. For instance, rRNA is known to have areas that are shared by a group of species and other segments that may be specific for a single species. Species specific amplification of rRNA can be carried out with one primer that is specific to one particular species and a second primer is complementary to a more diverse group. The genomes of *Neisseria gonorrhoea* and *Neisseria meningitidis* have very high levels of homology with only a few isolated chromosomal segments that are discrete to only one of the species and are flanked by segments that are shared by each species. Specific amplification can be carried out by a primer that is specific to one species and the other primer can be derived from flanking sequences that are shared in common.

Detection of the presence of oncogenic HPV using the methods and compositions of the present invention may be carried out by any of the means that have been previously described in the literature. For example in the simplest format, the sequences of the present invention can be used to design probes that will be specific for a group of oncogenic HPVs. These probes can be used with amplified or unamplified material depending upon the level of sensitivity that is desired. For instance, the probes can be used with dot blots, Southern blots, sandwich assays or in situ with unamplified specimens. Labels, methods for labeling and the use of such probes are described in U.S. Pat. No. 4,711,955, U.S. Pat. No. 5,241,060, U.S. Patent Application Serial No. 20030225247 and U.S. Patent Application Serial No. 2005037388 all of which are incorporated by reference. Also, a summary of useful methods are included in "Nonisotopic Probing, Blotting, and Sequencing" edited by Larry J. Kricka 1995 Academic Press, San Diego, Calif., also incorporated by reference herein.

The methods and compositions of the present invention can be used in conjunction with amplification assays by using primers that have been previously described, and by detecting with probes derived from the sequences of the present invention. On the other hand, the specific amplification of oncogenic HPV can be carried out by using the sequences of the present invention to design nucleic acid constructs that can act as primers. Detection of the amplification product can be carried out by means previously described in the literature, or by using the oncogenic HPV probes of the present invention. For example, detection of amplification by primers specific for oncogenic HPV could be carried out by gel electrophoresis analysis and noting the synthesis of a suitably sized amplicon. Real time assays based on synthesis alone can also be carried out by using intercalating dyes as described in by Higuchi in U.S. Pat. No. 5,994,056 and Rabbani et al. in U.S. Patent Application Serial No. 20050137388 filed on Mar. 12, 2002 (both of which are incorporated by reference). If desired, the specific type that has been amplified by means of the present invention can be established by a variety of methods known to those skilled in the art. For instance, the diversity of sequences between primer binding sites can be used to obtain type-specific RFLP patterns as described previously for generic HPV amplification. Also, if preferred, probe based assays can be used. These can be: a) generic, by using conserved sequences within the HPV amplicons; b) specific for oncogenic HPV, by using the sequences of the present invention; or c) they can be type-specific by using divergent sequences. Thus, in the first case, sequences that have been previously described in the literature as genus primers may be used as probes for the detection of amplified oncogenic HPV after amplification by means of the present invention. Alternatively, the sequences of the present invention that are conserved among oncogenic HPV types may also be used as the basis of designs for probes that would be specific for oncogenic types thereby potentially increasing the specificity of an assay for oncogenic HPV.

Probe based systems can be used in post-synthesis formats or in real time assay formats. Examples of post synthesis probe methods can include but not be limited to Southern blot, dot blot or sandwich assays. Examples of real time probe methods can include but not be limited to Taqman type assays and energy transfer. It is also contemplated that methods of endpoint analysis and realtime analysis that have been described by Rabbani et al., in U.S. patent application Ser. No. 10/096,076, hereby incorporated by reference, may also be used with the present invention.

The sequences of the present invention can also be used as primer/probes to detect the presence of appropriate oncogenic HPV sequences either with or without an amplification step. As described previously, the ability of a nucleic acid construct to use a target nucleic acid as a template for an extension reaction is highly dependent upon the matching of the 3' end of the nucleic acid construct with the template sequences. Therefore, distinguishing between closely related target and non-target nucleic acid sequences can be carried out by using a nucleic acid construct where the 3' end binds to a segment that is significantly different between the target (oncogenic HPV) and non-target (non-oncogenic HPV). By the use of conditions where the extension event is of limited extent, the ability to be extended or not can generate information on the presence or absence of the appropriate target. Control of the extent of extension can be carried out by a number of different means. For instance by not using the full complement of all four nucleotides, extension should be halted whenever the missing base or bases are supposed to be incorporated. Alternatively, the reaction can be carried out in a mixture where all four bases are present, but they act as terminators once they have become incorporated. Thus irrespective of the sequence, only a single base becomes incorporated. Examples of modified nucleotides and nucleotide analogues that can act as terminators can include but not be limited to dideoxynucleotides and acyclo analogues. Alternatively, one or more terminators can be used in conjunction with one or more normal bases.

Whether the appropriate base has been incorporated during the aforementioned limited extension may be determined in a number of ways. For instance, a single base could be labeled and the extent of incorporation may be measured. As an example, if dGTP is the labeled base, only templates that allow incorporation of a G before encountering the missing base or bases would be labeled. Thus, a primer may be designed where only the appropriate target will fulfill this ability. In another example, two different labeled ddNTPs can be used. For instance, incorporation of one nucleotide can indicate the presence of non-oncogenic HPV whereas the incorporation of the other base indicates the presence of oncogenic HPV. Evaluation of these incorporation events could be carried out using energy transfer where the primer contains a donor molecule and each of the different labeled ddNTPs comprises a different acceptor molecule. Thus, by measuring the samples at different wavelengths, the presence of oncogenic and non-oncogenic HPV could be ascertained.

Additionally, it should be pointed out that although these primers, probes and target sequences are suitable for use with the well characterized PCR system, many of the varied amplification systems that have been described in the literature such as SDA, NASBA, Engelhardt et al. in U.S. patent application Ser. No. 09/302,816, Rabbani et al. in U.S. patent application Ser. No. 09/104,067 all of which are hereby incorporated by reference, may also find use with the present invention. Similarly, many of the systems that have been used to augment these systems may also be used in the various aspects of the present invention. For example, in Rabbani et al. in U.S. patent application Ser. No. 09/104,067, (hereby incorporated by reference) the use of bases modified with Carboxy groups was disclosed where the introduction of such moieties into nucleic acids could result in nucleic acids with depressed melting points, allowing strand separations to take place under less severe condition. Other compounds that could also be used for this purpose are dITP and 7-deaza-GTP.

Cold Suppression

The specificity of amplification and/or detection may be increased by the addition of other reagents. For instance, the various probes or primers that may be used with the present invention have certain levels of homology with non-oncogenic HPV types. Previously, Rabbani and Engelhardt have disclosed the use of cold suppression to reduce signals generated by closely related non-target organisms in U.S. Pat. No. 4,755,458 (hereby incorporated by reference). It is a subject of the present invention that detection of HPV can be carried out by labeled and unlabeled probes where the unlabeled probes are derived from HPV sequences of types that are non-oncogenic. The labeled and unlabeled probes may be used as a mixture or they can be used sequentially or separately. Thus, all of the HPV types that are targets of the assay generate signal by hybridization of their complementary probes whereas non-target sequences that may be present in a sample demonstrate reduced hybridization with the labeled probes due to the binding of the complementary cold suppressor probes. This effect would lead to an increase in the S/N (signal to noise) ratio for target detection in a specimen.

The methods of U.S. Pat. No. 4,755,458 may be applied to the present invention by inverting the criteria for oncogenic probe selection, by using the same discrete region that was used for designing the probes for oncogenic HPV and selecting sequences for cold suppressor probes that would have high homology with HPV 6, 11, 42 or 44 or some other non-oncogenic HPV and low homology with the target sequences for the oncogenic probe.

An individual species of cold suppressor probe may be used that can act on one or more non-oncogenic types of HPV or a mixture of such cold suppressor probes may be used. The suppressor probes may be homologous to the entire region of the labeled probes or they may be homologous to only a portion of the region. In addition, the suppressor probes can have enhanced competitive ability by additionally comprising sequences flanking the region homologous to the probe or probes. The suppressor probes are nucleic acid constructs and may comprise any of the properties that were described previously. By the use of the suppressor probes of the present invention, signals from non-oncogenic varieties of HPV in amplified or unamplified samples could be reduced or even eliminated.

Also, instead of using probes that act as competitors post-synthetically, nucleic acid constructs can also be provided that will hinder or suppress amplification of non-target nucleic acids. For instance, in a situation where a primer is capable of an undesirable level of use of a non-target nucleic acid as a primer site, a "priming suppressor" can be designed that has higher affinity to the primer binding site in the non-target sequence compared to the target sequence. One method for preventing amplification by the priming suppressor is to have the 3' end blocked so it is unextendable and therefore unable to function as a primer per se. Thus, the present invention discloses that in the presence of appropriate HPV targets, the extendable primer has a higher affinity than the priming suppressor and amplification takes place. On the other hand, in the presence of a related non-target nucleic acid, the priming suppressor has a higher affinity than the extendable primer and the number of extension events remains limited or inhibited. Instead of blocking the 3' end, a priming suppressor can also be designed such that binding and extension events take place but all or a portion of the priming suppressor is unable to be used as a template for nucleic acid synthesis. Thus, even after a primer suppressor is extended and the synthesized sequences are used as a template, only a partial copy is created which lacks all or a portion of the original primer binding site, thereby eliminating new priming events.

One example of a priming suppressor that would have these properties is a construct that is synthesized using Peptide Nucleic Acids. Even though they have a high affinity for complementary nucleic acids, PNAs lack the ability to be recognized as a template by DNA or RNA polymerases. The priming suppressor can be composed entirely of such PNA moieties or it may be chimeric in nature and comprise normal nucleotides as well. Another example of a priming suppressor would be a construct that comprises two sequences that are linked together by moieties that are unable to be traversed by a polymerase. Examples of such moieties can include non sugar linkage units and inverted sugar phosphate bonds as described by Rabbani et al. in U.S. patent application Ser. No. 08/749,266 (incorporated by reference). The priming suppressors are designed such that binding of the two segments is stable, but regeneration of only one segment does not provide a sequence that is sufficient for further priming events. Competivity can also be increased by synthesizing the suppressors (probes or primers) with nucleotide analogues with modifications in their bases that increase stability. As described previously, examples of these are commercially available nucleotide analogues such as 2-amino A, 5-methyl-C, C-5 propynyl-C and C-5 propynyl-U and bases modified with Ethidum Bromide moieties.

Cold suppression of amplification can thereby take place by designing the priming suppressor in the same way previously described for cold suppression probes, i.e. a higher affinity for the non-target HPV (one or more of the non-oncogenic HPVs) and lower complementarity with the homologous primer binding site in the oncogenic HPV.

Primer suppressors can also act in the context of amplifications that depend upon ligation to provide extension events. For instance, a set of oligonucleotides can be ligated together in the presence of the appropriate template in what is called the Ligase Chain Reaction (LCR). The present invention discloses that inappropriate amplification from non-target organisms with similar sequences to the target organisms can be repressed by the use of a set of primers that are non-ligatable and have high homology with the non-target sequences. During the course of LCR type reactions, two oligonucleotides are aligned together on a complementary template nucleic acid. Ligation then takes place through the 3' OH on one oligonucleotide that is adjacent to the 5' $PO_4$ of the second oligonucleotide. One way of designing Primer suppressors would be to have these moieties reversed: a 5' OH on one suppressor nucleic acid and a 3' $PO_4$ on the other suppressor nucleic acid.

The design of the sequences for these primer suppressors can be carried out as described previously for suppressor probes. For instance, it was described above that a sequence with a selected sequence Q can distinguish between the included and non-included groups when the lowest number of matches of A, B or C with selected sequence Q is equal to an integer "n" and the highest number of matches of D, E or F with the selected sequence Q is an integer "x" which is equal to or less than "n−1". A cold suppressor probe or a priming suppressor can be designed on the same basis where the homologous sequences in the non-included group (with D, E and F) are used for selection of a sequence Q' where the lowest number of matches of D, E or F with sequence Q' is equal to an integer "y" and the highest number of matches of A, B or C with the selected sequence Q' is an integer "z" which is equal to or less than "y−1".

This method can also be carried out by using all or most of the HPV genomes as labeled and cold suppressor probes or if desired, it can be carried out by selecting particular sequences. An example of the former method would be the use of the FDA approved High Risk HPV assay by Digene with the further step of addition of unlabeled probes derived from genomic or subgenomic fragments of low risk HPV that have demonstrated cross-reactivity. As described previously, HPV 6, 11 and 42 (which were included in their Low Risk HPV assay) have generated signals with the High Risk probes (ALTS Group 2000 J. National Cancer Inst. 92; 397-402; Hughes et al. 2002 Am J Obstet Gynecol 186; 396-403). Also the same sources cited cross-reactivity with HPV 53 which is likely to be a member of the Low Risk group. Any and all of the foregoing are candidates to be used as sources of cold suppressor probes. In assays where the probes are RNA and detection is carried out by a monoclonal antibody that recognizes the RNA probe bound to a DNA target cold suppressor probes made from DNA instead of RNA will essentially be "unlabeled" probes.

The suppressor probes can encompass the entire genomic region that is homologous to the region covered by the labeled probes. For instance, if the entire genomes of oncogenic HPVs are used as probes, the entire genomes of non-oncogenc HPVs can be used as cold suppressor probes. If subgenomic fragments of oncogenic HPVs are used as probes, the homologous segments of non-oncogenic HPVs can be used as cold suppressor probes. Alternatively, only a portion of the homologous regions may be used if desired. For instance, it is well known that when comparing the sequences of related HPVs, the levels of homology are not homogeneous across the genome and different regions have characteristic variability where some regions comprise sequences that are relatively conserved (and thus held in common) and other regions are unique to the particular HPV type. Thus, cold-suppressor probes may be designed for only the portions of the labeled probes that generate the most significant levels of cross-reactivity. Also as described previously, competition by these suppressor sequences may be augmented by substitution of nucleotide analogues that increase thermal stability. In addition to the phosphoramidites described previously, nucleotides are also available that can be incorporated enzymatically. These nucleotides may comprise 2-Aminoadenosine, 5-Methylcytidine, 2-Amino-2'-deoxyadenosine, 5-Proponyl-2'-deoxycytidine, 5-Proponyl-2'-deoxyuridine and 5-Methyl-2'-deoxycytidiene are all available as Triphosphates from TriLink Biotechnologics, Inc. (San Diego, Calif.).

In addition to acting passively by binding, cold suppression can be carried out by active means as well. For instance, if mRNA is the target being identified, DNA oligonucleotides that are complementary to non-target sequences can be added and subsequently treated with RNase H1. For instance, if expression analysis is being carried out to monitor the presence of E6 mRNAs of oncogenic HPV, the application of E6 DNA from non-oncogenic varieties (such as HPV 6, HPV 11, HPV 42, HPV 43 or HPV 44) can result in preferential reduction of their corresponding mRNAs in a sample, leaving the oncogenic mRNAs available for analysis.

Primer Site Alteration with Degenerate Bases

It is a further subject of the present invention that novel methods and compositions are disclosed where primers with degenerate bases (Alteration Primers), are used to generate nucleic acid copies of analytes that have primer binding sites which represent different sequences from the initial analytes. The artificially introduced sequences in the analyte copies provide binding sites for one or more complementary nucleic acid constructs that can detect the presence of the altered sequence (Discriminator Probes), provide for generating additional copies of the analytes (Discriminator Primers) or provide a combination of both functions. Prior art has described the use of degenerate bases such as Inosine in primer design, but this has been strictly for the purpose of compensating for the presence of ambiguities or variability in potential target sequences since Inosine can base-pair with all four nucleotides with varying levels of stability.

However, prior art has failed to recognize another property of such nucleotide analogues. Although the hallmark of a degenerate base is its ability to base pair with more than one base, the choice of which nucleotide to insert or incorporate opposite a degenerate base may show preferential biases during nucleic acid synthesis depending upon the particular degenerate base being used. For instance, the base analogue "P" has little bias and an A or a G are almost equally likely to be incorporated (Hill et al., 1995 Proc. Nat. Acad. Sci. USA 95; 4258-4263). This is also true for the base analogue 8-oxo guanidine where either an A or a C is incorporated. On the other hand, Inosine can base pair with different bases for binding of a probe or a primer, but when it is used as a template, it functions essentially as a G and the nucleotide incorporated opposite it will predominantly be a C (Kamiya et al., 1992 Chem Pharm Bull. 40; 2792-2795). Additionally, the base analogue "K" can base pair with either A or T, but when it is used in a template it predominantly directs incorporation of T (Hill et al., 1995 supra). Thus, some degenerate bases can be relatively non-selective in terms of its binding properties, but more selective in terms of template abilities. In the present invention, degenerate bases that show a strong preference for incorporation of a particular nucleotide will be referred to a "selective degenerate bases" and the particular nucleotide that is preferentially incorporated opposite a selective degenerate base will be referred to as a "preferred base". This selective property of degenerate bases may be applied in various ways.

In contrast to prior art that uses a primer with degenerate bases for both initial rounds of amplification and for all subsequent rounds of amplification, the present invention discloses a novel system where at least two primers are used for the same region: a) an Alteration Primer that comprises selective degenerate bases; and b) a Discrimination Primer that is complementary to the new sequences derived from using Alteration Primers as templates. Thus, when an extended Alteration Primer is copied as a template, insertion of preferred bases opposite the positions of selective degenerate bases in the primer segment will provide a primer binding site for a Discrimination Primer where bases complementary to the preferred bases are located in the positions that had been used for selective degenerate bases in the Alteration Primer. An Alteration Primer and Discriminator Primer system may be used as forward primers, reverse primers or if desired, both forward and reverse primers may comprise Alteration Primers and Discriminator Primer systems.

If an amplification or copying reaction is carried out where only the forward primers comprise an Alteration Primer and Discriminator Primer system, one or more normal primers have to be included in the reaction as reverse primers, where the term "normal primers" is intended to only imply that they do not comprise part of an Alteration Primer and a Discriminator Primer system. Contrariwise, normal primers need to be provided as forward primers when only the reverse primers comprise an Alteration Primer and Discrimination Primer system. Normal primers may comprise a single discrete sequence or if increased breadth of target recognition is required, they may be part of a set of primers that have variable bases in selected positions or they may also comprise degenerate bases. Alteration Primers, Discrimination Primers and normal primers may comprise modified nucleotides, unmodified nucleotides and nucleotide analogues. They may be unlabeled or they may be labeled with any useful moieties known to the art.

The use of the same region by a different primer for subsequent rounds in place of the degenerate primer can convey multiple benefits. First, primers comprising degenerate bases are not as efficient as primers with normal bases. Thus, in a situation where degenerate bases are used to compensate for ambiguities or variabilities, previous art has been handicapped by the continued reliance on these inefficient substituted primers to synthesize appropriate levels of copies or amplification products. This can lead to low levels of synthesis or even complete failure to amplify desirable sequences, especially with primers that have multiple substitution sites.

The present invention overcomes this problem by limiting the need for degenerate primers to bind to sequences of the original analytes and the need to initiate amplification since a consequence of the process of using selective degenerate bases in the initial rounds may be a transformation of ambiguous target sequences into artificially specific sequences. Since the product of synthesis from primers with selective degenerate bases can be a single discrete sequence, there is no need for tolerance of sequence variations of primer binding sites and further rounds of amplification can be carried out efficiently by Discrimination Primers designed to specifically match the synthetic sequences that are generated from copying the degenerate bases. Whereas previously, efficiency had to be sacrificed for the sake of breadth of target recognition, breadth and efficiency can now be simultaneously retained by use of the methods and compositions of the present invention. Also, non-stringent conditions are often used in conjunction with degenerate primers as a further compensation for variability. Since the second primers (Discrimination Primers) can be perfect complements to the new primer binding sequences of the amplicon, more stringent and more efficient amplification conditions may also be applied in later rounds. As an illustrative example of this method, an Alteration Primer can have the degenerate base "K" in three different sites to compensate for an ambiguity of having either an A or T in that position for various target sequences. Since the "K" analogue has a strong bias towards incorporation of a T opposite the "K" when it is used as a template, a Discrimination Primer can be used in later rounds that has an A in each of the positions used by "K" in the Alteration Primer.

In another example, one problem that always arises with amplification systems is that a limited correspondence of non-target nucleic acids with sufficiently similar primer binding sequences may allow mispriming events that lead to spurious amplification of these non-target sequences. Due to the nature of amplification mechanisms, this is a continuous problem during the course of the amplification reaction. Every cycle is an opportunity for a new primer binding event to initiate non-target amplification. Thus, the present invention discloses that target sequences that are relatively conserved and constant may also find use as sites for substitution of degenerate bases in primers. The use of Alteration Primers that are used for the first few rounds can be followed by altered conditions such that the primary targets can no longer be used as primer binding sites and only the amplification products can be used as templates. This can bring about an increased separation between target sequences and non-target sequences do not amplify.

An example of this process is shown in FIG. 1 with an arbitrary target sequence, and a related non-target sequence that differs from the target sequence in only two nucleotide positions. The top of FIG. 1 shows how a discrete primer without degenerate bases would have only two mismatches with the related non-target sequence. In step (1) an Alteration Primer with three degenerate bases is used as a forward primer in place of the discrete primer. In a situation where there are only two mismatches of the Alteration Primer with an undesirable sequence, only a low level of spurious amplification that takes place in the first few rounds has to be contended with. After a first copy is made by extending the Alteration Primer, a reverse primer is bound to the first copy and extended as shown in steps (3) and (4). In step (4) of FIG. 1, the Inosine moieties in the Alteration Primer portion of the first copy are copied as if they are Gs. Thus, where the original analyte had As in three sites, the product of step (4) has Cs instead. This sequence is now a perfect match for a Discriminator Primer that has Gs in the positions of the Alteration Primer that had Inosine moieties. By altering the base pairing of a primer to a primer binding sequence to G:C base pairing rather than A:T base pairing, the thermal stability should be raised by about 2° C. per alteration, theoretically allowing the annealing temperature to be raised as much as 6° C. higher when Discriminator Primers are used that match the new sequences. Thus, when conditions are altered such that the Discrimination Primers are the primary source of priming and extension events, the non-target sequences in FIG. 1, which have 5 mismatches between their sequences and the Discrimination Primers, are essentially eliminated as potential sources of spurious amplification events. Accordingly, the first few rounds of amplification can be carried out at a temperature that allows efficient priming by an Alteration Primer and the production of copies that have altered nucleic acid sequences in the primer binding segment. This can then be followed by raising the temperature such that the reaction relies on the use of the Discrimination Primer instead of the Alteration Primer.

A further level of discrimination can be achieved where the Discrimination Primer binds to all or part of the same region as the Alteration Primer but the Discrimination Primer comprises additional sequence information that enables preferential binding or extension to target sequences compared to related non-target sequences. As described above, mispriming events are a continuing potential source of spurious amplification products in prior art. The use of the present invention can reduce the impact of such synthesis by reducing the likelihood of such mispriming events to the first few rounds when the original analytes remain a main source of amplification templates. However, when the Discrimination primer uses the same sequences as the Alteration Primer with the exception of the degenerate base positions, low levels of spurious non-target amplicons that may have been synthesized in the first few rounds are used as efficiently as amplicons derived from target nucleic acid sequences for further rounds of amplification by the Discrimination Primers.

If desired, even this low level of spurious amplification can be reduced by the design of Discrimination Primers that can distinguish between target derived amplicons and non-target derived amplicons. For instance, although the ends of both target amplicons and non-target amplicons will be similar since they were derived from copying the primer sequences as templates, the sequences that are located between the primer binding sites will be different for target amplicons and non-target amplicons and this may be used as a basis for further discrimination. Thus, in this aspect of the present invention, a Discrimination Primer may comprise all or a portion of the same segment used by the Alteration Primer and additionally comprise sequences that will be complementary to a segment outside of the area used for binding of the Discrimination Primer. This additional segment can comprise a single base, or multiple bases. By these means, a Discrimination Primer may be designed that is preferentially bound and extended with target derived products as compared to non-target derived products that may be present in the reaction mixture after extensions of Alteration Primers. In a preferred mode, these sequences are included in the 3' end of the Discrimination Primers since this region is well known to be the most critical region of a primer for determining specificity. Additionally, a discrimination primer may comprise degenerate bases or permutational assignments in the additional segment if further breadth of coverage is desired.

An illustration of this aspect of the present invention is given in FIG. 2. The same Alteration Primer that was used in FIG. 1 is also used in this example, but in FIG. 2 the target and non-target sequences are also illustrated in terms of bases adjacent to the Alteration Primer binding sites where each sequence is differentiated by a single base difference in the area next to the Alteration Primer binding area. As illustrated in step 2, as well as the valid target (A) that is used as a template, the non-target (B) is shown as being used as a template for an extension reaction with the ultimate synthesis of a target amplicon (A) and a non-target amplicon (B) in step 4. However, in contrast to FIG. 1 where the exemplarary Discriminator Primer ended in AACGA at the 3' end, the Discriminator Primer in FIG. 2 has a Discriminator Primer that ends in AACGAG. As such as shown in step 5 of FIG. 2, the presence of this additional nucleotide should provide a G:G base pairing mismatch at the end which should substantially prevent extension of the Discriminator Probe when using a non-target derived product as a template.

In addition, although an Alteration Primer and a Discrimination Primer were used as forward primers and a single primer was used as a reverse primer in FIG. 1, it is understood that the arrangement in this example could be reversed with a single primer as a forward primer and an Alteration Primer and a Discrimination Primer system used as reverse primers. It is also understood that it is a subject of the present invention that a set of primers comprising an Alteration Primer and a Discrimination Primer can be used as forward primers in conjunction with a second set of primers comprising an Alteration Primer and a Discrimination Primer used as reverse primers.

Also, a Discrimination Probe that generates a signal in the presence of the synthetic altered sequences that are created by copying an Alteration Primer may be used either during the course of synthesis or after synthesis is complete. In its simplest form, the hybridization of a labeled Discrimination Probe to an altered sequence may be used for signal generation. More sophisticated systems may also be used where a labeled Discrimination Probe can be part of an energy transfer signal system. For example, an energy transfer donor may be used to label a probe and an energy transfer acceptor may be: a) a separate probe; or b) an intercalator. Additionally, Discrimination Probe/Primers can be used where incorporation can be used to monitor the presence of appropriate sequences. For a more full discussion of energy transfer and nucleic acid constructs that may serve as both probes and primers see Rabbani et al. in U.S. application Ser. No. 10/096,076, incorporated herein by reference.

As described previously for Discrimination Primers, Discrimination Probes may be designed such that they encompass the same sequences as the Alteration Primers with the exception of the degenerate base positions. For instance, in the example shown in FIG. 1, if the sequence shown for a Discrimination Primer was used as a probe, a strong differential effect of hybridization would be seen for binding of a Discrimination Probe to the synthetic sequence derived from the target sequence (no mismatches) as opposed to the homologous non-target sequence (5 mismatches). Alternatively, a primer/probe could utilize the differential sequences outside of the binding segment used by the Alteration Primer. For instance, if a Discrimination Probe/Primer used the same segment as the Alteration Primer, the particular base incorporated by extension of the Primer/Probe could be used to provide signal discrimination between target and non-target. In the example shown in FIG. 2, if the 3' end of the Probe/Primer was AACGA-3', extension using an altered target copy as a template would direct incorporation of a G; in contrast, extension using an inadvertently copied non-target sequence as a template would require incorporation of a C. As such, various means could be used that exploit this difference. For example, an extension reaction could be carried out where only labeled G would be provided as a substrate. Only the target derived copies should allow incorporation of label. Alternatively, unlabeled G and a labeled A could be provided. As seen from the sequence shown in FIG. 2, the target derived copy should be able to incorporate the labeled A after incorporation of an unlabeled G, but the inability of the non-target copy to direct incorporation of a G should also preclude incorporation of the labeled A. An alternative to limiting the nucleotide species would be to provide all 4 nucleotides in the form of terminators with only the G being labeled. Also as described above, a Discrimination Probe or Primer/Probe could include additional sequences at the 3' end that were not included in the sequence of the Alteration Primer. Differential hybridization or differential extension could then be used for signal generation as described above.

Primers with Segments Incapable of Acting as Templates

In another aspect of the present invention, methods and compositions are disclosed for primers that comprise nucleic acid or nucleic acid analogue segments that are incapable of being used as templates but provide stability through binding to target nucleic acid strands. Examples of means that can provide such binding can include but not be limited to moieties that contribute to base-pairing, base stacking or any combination thereof. For instance, when primer sequences have only incomplete matches with target nucleic acids, later rounds of amplification can take place with much higher efficiency than the initial first few rounds. This takes place due to an intrinsic part of the use of primers as templates for some of the amplification steps. For instance, if a primer has a few mismatches with the target but succeeds in being extended, the use of this extended forward primer as a template by a reverse primer will produce a second strand that has primer binding sites that are perfectly complementary to the forward primers. Thus, the sequences in a primer provide for a "self-correcting" function when regenerating a sequence that can be used for primer binding in subsequent amplification steps. As such, one method of amplifying nucleic acids with potential mismatches is to use a lower stringency of annealing in the first few rounds where the primer binding site is provided by the target nucleic acids and there is low thermal stability between the primers and target sequences. This is then followed by a shift to higher stringency when the copies or amplicons become the primary source of templates and there is a consequential higher binding affinity between the primers and the amplicon sequences. However, this use of low stringency in the methods of prior art has the limitation that it allows undesirable non-target sequences to become potential amplification targets as well.

To overcome this limitation, the present invention provides stabilizing elements that may compensate for mismatches between the primer and a target nucleic acid, thereby allowing the use of higher stringency conditions during initial rounds of copying or amplification. In the present invention, when extended primers are copied, the stabilizing elements aren't copied as templates and therefore, complementary strands synthesized from these extended primers do not regenerate the sequences used for binding the stabilizing elements. In subsequent rounds, stability is provided by the "corrected" sequences in the copies. Examples of compounds that may be used in this aspect of the present invention have been described previously for designing suppressor primers.

An example of this process is given for an arbitrary sequence in FIG. 3. Example A shows a composite nucleic acid construct with two segments tethered together. The compounds that are used to join the two segments together can comprise a chain of abasic nucleotides, totally artificial linkages or a combination of both. The segment at the 5' end of this example is a stabilizing segment comprising an octanucleotide sequence and the 3' end is a primer segment that has three mismatches with a target sequence. As shown in step (1) of FIG. 3, both the primer segment and the stabilizing element segment should be able to bind to their complementary sequences in the target nucleic acid strand. The additional presence of the octanucleotide stabilizing segment should allow a higher stability of binding of the composite primer with the mismatched target sequences (three mismatches) than if the primer segment was used alone as a primer. In step (2) the composite primer is extended and in step (3) the extended composite primer participates in binding of a reverse primer in order to generate a complementary copy. In step (4) extension of the reverse primer ultimately leads to using a portion of the original composite primer sequence as a template. As seen in FIG. 3, copying of the priming segment of the composite primer generates a different sequence than that seen in step (1) i.e. the bases with arrows underneath them in step (4) have replaced the underlined bases seen in step (1). In the composite primer in this example, the lack of nucleotide templates between the two segments halts further extension after the primer segment of the composite primer has been used as a template and the stabilizer segment is not copied. During the course of further rounds of synthesis, amplicons will accumulate that lack sequences complementary to the stabilizing segment but have a, perfect match with the primer segment. By these means, the present invention will allow transformation of the original target sequences into copies that perfectly match the primer segment without undergoing low stringency initial rounds. Further rounds of binding and extension using the "corrected" sequences as primer binding sites can be carried out with the composite primer used in the initial rounds of copying, or if desired, a second primer can be used that is complementary to the altered sequences but lacks the stabilizing elements. For example, a mixture of forward primers could be used that comprise a low concentration of first forward primers with stabilizing elements and a higher concentration of second forward primers without the stabilizing elements. Thus, in the first few rounds only the primers that have the benefit of the extra stabilizing elements are used for priming and extension whereas in later rounds, the presence of the "corrected" sequences would allow primers that lack the stabilizer elements to be functional. The primers with stabilizing elements could be the major driving force during initial rounds even though they comprise a minority of the population since they have the higher binding stability. After appropriate sequences have been synthesized, the primers with stabilizing elements lose their competitive advantage and the majority of syntheses could be carried out by the standard primers since they are present in greater quantities.

The second forward primers can comprise the same sequence as the primer segment of the composite primers used as first forward primers or they may comprise additional sequences. As described previously, the use of additional sequences can allow a greater degree of specificity since binding can take place with both target and non-target derived amplicons, but further extension events are selectively carried out when an amplicon comprises sequences that match the additional sequences in the second forward primers. Additionally, a form of "nested" nucleic acid synthesis can take place where the second forward primers comprise stabilizing elements that are complementary to the "corrected" sequences and as such, their functionality in the second forward primers only comes into play when "corrected" primer binding sites are synthesized.

Although the example depicted in FIG. 3 uses a composite primer as a forward primer, it is understood that the composite primer could have been used as a reverse primer or that initial rounds of amplification could have been carried out in a system where both forward and reverse primers comprised stabilizer elements.

FIG. 3 shows other examples of compositions that could be used as stabilizing elements in the present invention. In Example (B), peptide nucleic acids (PNAs) are located at the 5' end of a nucleic acid construct. (The PNAs are indicated by bold lettering.) Since they are intrinsically unable to be used as templates, extension in step (4) would again halt after the primer segment was copied and bases complementary to the PNA portion would not be synthesized. Since a gap is not needed to limit extension, the PNAs can be synthesized such that they are immediately adjacent to the primer segment. In addition, fewer nucleotides are needed to provide effective stabilization since in general, PNAs show higher thermal stability than their normal counterparts. In Example (C), a segment comprising universal bases (designated as "X") is located at the 5' end of a nucleic acid construct. One of the properties of these compounds that makes them universal bases is an ability to contribute stability through base stacking, thus contributing to the overall stability of base-pairing of a nucleic acid that includes these moieties. Examples of bases that would be useful for this purpose are 3-nitropyrrole and 5-nitroindole. The properties of these and other such universal bases are reviewed in Loakes (2001, Nucl Acids Res 29; 2437-2447), incorporated herein by reference. Although these analogues have been successfully used as probes, their inability to be used efficiently as templates has previously limited their use in primer design. However, in the context of the present invention, this is an advantageous quality rather than a limitation. This exemplary method offers a further benefit in that sequences in the target nucleic acids adjacent to the primer segment can be of unknown or ambiguous nature while still being functional in participating in binding of the primer construct.

It should be noted that various aspects of the present invention may be used alone or in conjunction with each other. For instance, the use of stabilizer elements can be used in the design of Alteration Primer/Discrimination Primer pairs to promote the efficiency of the initial extensions by Alteration Primers. Likewise, although relatively conserved regions of HPV sequences have been disclosed that can be used for selective amplification of multiple oncogenic HPV types, there remains enough variablility within these regions that the use of Alteration Primer/Discrimination Primer pairs and/or stabilizer elements may improve the sensitivity or efficiency of amplification.

EXAMPLES

In the following examples, nucleotide locations for various regions are based upon Genbank sequences as follows:

| Gene 16 cluster: | HPV 16 sequence; accession #K02718 |
| Gene 18 cluster: | HPV 18 sequence; accession #X05015 |
| Gene 51 cluster: | HPV 51 sequence; accession #M62877 |

The information on sequence comparisons between HPV 6, 11, 16, 18, 31, 33, 35, 39, 42, 43, 44, 45, 51, 52, 53, 56, 59, 66, 68 and 70 were taken from a web page of the "Human Papillomavirus 1997 Compendium" at the website having the address hpv-web.lanl.gov. The compendium is also available in paper by writing to HPV Database Mailstop K710

Los Alamos National Laboratory

Los Alamos, N. Mex. 87545.

Sequence comparisons between these and other HPV types may also be carried out using a number of commercially available software programs as well as a large number of sequences that have been published in the literature or deposited in Genbank.

In addition to sequence comparisons between a reference HPV strain (HPV 16, HPV 18 or HPV 51) and other related "target" HPV types as well as selected non-target HPV types, sequences derived from these comparisons that could be used as potential consensus sequences are also illustrated in order to facilitate the design of primers or probes that could be used for these regions.

In the various examples that follow, the HPV types included as "targets" are selected from HPV 16, 18, 31, 33, 35, 39, 45, 51, 52, 56, 58, 59 and 68. In the various examples that follow, the HPV types included as "non-targets" are selected from HPV 6, 11, 42, 43 and 44. Additional related HPV types whose oncogenic propensity has not been clearly established at the present time (HPV 53, 66 and 70) have also been included in sequence comparisons with related HPV types. When describing exemplary primer and probe sequences, maximal non-target match is expressed with regard to the highest match level with HPV 6, 11, 42, 43 or 44.

Theoretical Tm of probes and primers is an estimate based upon the formula of:

$$Tm = 2° C./(AT \text{ pair}) + 4° C./(GC \text{ pair}).$$

When using degenerate bases in probe or primer designs, the theoretical Tm has been calculated with the formula above using only the normal bases (i.e. contributions from the degenerate bases were ignored). As such, it should be understood that the Tm's of such probes and primers are likely to be higher than listed (and consequently more stable).

Example 1

Selection of Conserved Differential Sequences from the E6 Gene

A) HPV 16 Cluster

Region E6-16-1(a) [Starting at Nucleotide 314] (SEQ ID NOS 1-11, respectively in order of appearance)

| 16 | TCTAA | AATTA | GTGAG | TATAG | ACATT | AT | mismatches |
|---|---|---|---|---|---|---|---|
| 35 | --A-- | ---A- | ----A | ----- | -TGG- | -- | 6 |
| 31 | --A-- | -G-A- | ----A | -T--- | -TGG- | -- | 8 |
| 52 | ----- | G--A- | ----A | ----- | G---- | -- | 4 |
| 33 | ----- | ----- | ----A | ----- | ----- | -- | 1 |
| 58 | ----- | ---AG | ----- | ----- | ----- | -- | 2 |
| 6 | GGA-- | ---A- | ACC-A | ----- | ---C- | T- | 10 |
| 11 | GGG-- | ----- | ACC-A | ----- | ---C- | T- | 9 |
| 42 | ----- | ----T | ---CA | CTGC- | ---C- | -C | 9 |
| 43 | GGA-- | ----A | --C-A | ----- | G--C- | T- | 9 |
| 44 | GG--- | GG-C- | A-C-A | -T--- | G---- | T- | 11 |

Potential Consensus E6-16-1(b) (SEQ ID NOS 12-21, respectively in order of appearance)

| | TCTAA | AATTA | GTGAA | TATAG | ACATT | AT | |
|---|---|---|---|---|---|---|---|
| 16 | ----- | ---T- | ----G | ----- | ----- | -- | 2 |
| 52 | ----- | G---- | ----- | ----- | G---- | -- | 2 |
| 33 | ----- | ---T- | ----- | ----- | ----- | -- | 1 |
| 58 | ----- | ----G- | ----G | ----- | ----- | -- | 2 |
| 6 | GGA-- | ----- | ACC-- | ----- | ---C- | T- | 8 |
| 11 | GGG-- | ---T- | ACC-- | ----- | ---C- | T- | 9 |
| 42 | ----- | ---TT | ---C- | CTGC- | ---C- | -C | 9 |
| 43 | GGA-- | ----- | --C-- | ----- | G--C- | T- | 7 |
| 44 | GG--- | GG-C- | A-C-- | -T--- | G---- | T- | 8 |

For consensus sequence E6-16-1(b), the lowest match with HPV 16, HPV 33, HPV 52 and HPV 58 is 25 out of the 27 bases; the highest match for HPV 6, HPV 11, HPV 42, HPV 43 and HPV 44 is 20 out of 27.

Potential Consensus E6-16-1(c) (SEQ ID NOS 22-29, respectively in order of appearance)

| | TCAAA | AGTAA | GTGAA | TATAG | ATGGT | AT | mismatches |
|---|---|---|---|---|---|---|---|
| 35 | ----- | -A--- | ----- | ----- | ----- | -- | 1 |
| 31 | ----- | ----- | ----- | -T--- | ----- | -- | 1 |
| 6 | GG--- | -A--- | ACC-- | ----- | -CAC- | T- | 10 |

|    | TCAAA | AGTAA | GTGAA | TATAG | ATGGT | AT | mismatches |
|----|-------|-------|-------|-------|-------|-----|-----------|
| 11 | GGG-- | -A-T- | ACC-- | ----- | -CAC- | T- | 12 |
| 42 | --T-- | -A-TT | ---C- | CTGC- | -CAC- | -C | 13 |
| 43 | GG--- | -A-A- | --C-- | ----- | GCAC- | T- | 10 |
| 44 | GGT-- | G--C- | A-C-- | -T--- | GCA-- | T- | 12 |

For consensus sequence E6-16-1(c), the lowest match with HPV 31 and HPV 35 is 26 out of the 27 bases; the highest match for HPV 6, HPV 11, HPV 42, HPV 43 and HPV 44 is 17 out of 27 (HPV 6 and HPV 43).

Region E6-16-2(a) [Starting at Nucleotide 404] (SEQ ID NOS 30-40, respectively in order of appearance)

|    | ATTAG | GTGTA | TTAAC | TGTCA | AAAGC | CACTG | TGTCC | mismatches |
|----|-------|-------|-------|-------|-------|-------|-------|------------|
| 16 | ATTAG | GTGTA | TTAAC | TGTCA | AAAGC | CACTG | TGTCC |            |
| 35 | ----- | ----- | ---CA | ----- | ---A- | -G--- | ----- | 4 |
| 31 | ----- | ----- | --A-CG | ----- | --GA- | -GT-- | ----- | 7 |
| 52 | ----- | A---- | --A-TT | ----- | --C-- | --T-A | ----- | 7 |
| 33 | ----- | ----- | ---TA | ----- | --GA- | -TT-- | ----- | 6 |
| 58 | ----- | A---- | ---TT | ----- | --GA- | --T-- | ----- | 6 |
|  6 | ---C- | ---CT | ACCTG | ----- | C--A- | -G--- | ---GA | 13 |
| 11 | ---C- | T---T | ACCTG | ----- | C----- | -GT-- | ---GA | 13 |
| 42 | ---C- | C---G | C--TA | ----- | ----- | -GT-A | -CA-A | 12 |
| 43 | ----- | A--CT | G---G | ----- | C----- | --T-A | -CA-- | 10 |
| 44 | --AC- | C--CT | A-TTG | TGCCA | C--A- | --T-- | --C-A | 19 |

Potential Consensus E6-16-2(b) (SEQ ID NOS 41-52, respectively in order of appearance)

|    | ATTAG | GTGTA | TTATC | TGTCA | AAAAC | CATTG | TGTCC | mismatches |
|----|-------|-------|-------|-------|-------|-------|-------|------------|
| 16 | ----- | ----- | ---A- | ----- | ---G- | --C-- | ----- | 3 |
| 35 | ----- | ----- | ---CA | ----- | ----- | -GC-- | ----- | 4 |
| 31 | ----- | ----- | --A-CG | ----- | --G-- | -G--- | ----- | 5 |
| 52 | ----- | A---- | -A--T | ----- | --CG-- | ----A | ----- | 6 |
| 33 | ----- | ----- | ----A | ----- | --G-- | -T--- | ----- | 3 |
| 58 | ----- | A---- | ----T | ----- | --G-- | ----- | ----- | 3 |
|  6 | ---C- | ---CT | ACC-G | ----- | C---- | GC--- | ---GA | 12 |
| 11 | ---C- | T---T | ACC-G | ----- | C--G- | -G--- | ---GA | 12 |
| 42 | ---C- | C---G | C---A | ----- | ---G- | -T--A | -CA-A | 11 |
| 43 | ----- | A--CT | G--AG | ----- | C--G- | ----A | -CA-- | 11 |
| 44 | --AC- | C--CT | A-T-G | TGCCA | C---- | ----- | --C-A | 16 |

For consensus sequence E6-16-2(b), the lowest match with HPV 16, HPV 31, HPV 33, HPV 35, HPV 52 and HPV 58 is 29 out of the 35 bases; the highest match for HPV 6, HPV 11, HPV 42, HPV 43 and HPV 44 is 24 out of 35.

Potential Consensus E6-16-2(c) [Using Degenerate Base "P" for C and T and Using Degenerate Base "K" for A and G] (SEQ ID NOS 53-64, respectively in order of appearance)

| | ATTAG | GTGTA | TTAPP | TGTCA | AAKKC | CKTTG | TGTCC | mismatches |
|---|---|---|---|---|---|---|---|---|
| 16 | ----- | ----- | ---A- | ----- | ----- | --C-- | ----- | 2 |
| 35 | ----- | ----- | ----A | ----- | ----- | --C-- | ----- | 2 |
| 31 | ----- | ----- | -A--G | ----- | ----- | ----- | ----- | 2 |
| 52 | ----- | A---- | -A--- | ----- | --C-- | ----A | ----- | 4 |
| 33 | ----- | ----- | ----A | ----- | ----- | -T--- | ----- | 2 |
| 58 | ----- | A---- | ----- | ----- | ----- | ----- | ----- | 1 |
| 6 | ---C- | ---CT | ACC-G | ----- | C---- | --C-- | ---GA | 11 |
| 11 | ---C- | T---T | ACC-G | ----- | C---- | ----- | ---GA | 10 |
| 42 | ---C- | C---G | C---A | ----- | ----- | -T--A | -CA-A | 10 |
| 43 | ----- | A--CT | G--AG | ----- | C---- | ----A | -CA-- | 10 |
| 44 | --AC- | C--CT | A-T-G | TGCCA | C---- | ----- | --C-A | 16 |

After using degenerate bases (P and K), the lowest match for consensus sequence E6-16-2(c) with HPV 16, HPV 31, HPV 33, HPV 35, HPV 52 and HPV 58 is 31 out of the 35 bases; the highest match for HPV 6, HPV 11, HPV 42, HPV 43 and HPV 44 is 25 out of 35.

B) HPV 18 Cluster

Region E6-18-1(a) [Starting at Nucleotide 132] (SEQ ID NOS 65-70, respectively in order of appearance)

| | CGACC | CTACA | AGCTA | CCTGA | TCTTG | CA | mismatches |
|---|---|---|---|---|---|---|---|
| 18 | | | | | | | |
| 45 | ----- | ----- | ----- | --A-- | -T--- | -- | 2 |
| 39 | --G-- | A---- | -AT-G | --A-- | C---- | -- | 7 |
| 68 | --G-- | A---- | -AT-G | --A-- | C---- | -- | 7 |
| 70 | --G-- | A---- | -AT-G | ----- | C---- | -- | 6 |
| 59 | ----- | A---- | -A--G | ----- | -T-A- | -- | 5 |

Potential Consensus E6-18-1(b) (SEQ ID NOS 71-82, respectively in order of appearance)

| | CGACC | CTACA | AACTA | CCTGA | TTTTG | CA | mismatches |
|---|---|---|---|---|---|---|---|
| 18 | ----- | ----- | -G--- | ----- | -C--- | -- | 2 |
| 45 | ----- | ----- | -G--- | --A-- | ----- | -- | 2 |
| 39 | --G-- | A---- | --T-G | --A-- | CC--- | -- | 7 |
| 68 | --G-- | A---- | --T-G | --A-- | CC--- | -- | 7 |
| 70 | --G-- | A---- | --T-G | ----- | CC--- | -- | 6 |
| 59 | ----- | A---- | ----G | ----- | ---A- | -- | 3 |
| 6 | GC-A- | GAC-- | T-GAC | -AG** | *---- | -- | 15 |
| 11 | GC-A- | A-CT- | T-GAC | -AG** | *---- | -- | 15 |
| 42 | -AG-- | ACGC- | C-T-- | TACC- | ----- | -- | 12 |
| 43 | GC--G | GACT- | T-T-T | GAG** | *---- | -- | 16 |
| 44 | GC--A | AAGT- | T-GAC | -AG** | *---- | -- | 16 |

In the example above (and in following examples), the symbol * was used to indicate the absence of a base when the sequences were aligned for best fits.

Potential Consensus E6-18-1(c) (SEQ ID NOS 83-94, respectively in order of appearance)

| | CGGCC | ATACA | AATTG | CCAGA | CCTTG | CA | mismatches |
|---|---|---|---|---|---|---|---|
| 18 | --A-- | C---- | -GC-A | --T-- | T---- | -- | 7 |
| 45 | --A-- | C---- | -GC-A | ----- | TT--- | -- | 7 |
| 39 | ----- | ----- | ----- | ----- | ----- | -- | 0 |
| 68 | ----- | ----- | ----- | ----- | ----- | -- | 0 |
| 70 | ----- | ----- | ----- | --T-- | ----- | -- | 1 |
| 59 | --A-- | ----- | --C-- | --T-- | TT-A- | -- | 6 |
| 6 | GCAA- | GAC-- | T-GAC | -AG** | *T--- | -- | 14 |
| 11 | GCAA- | --CT- | T-GAC | -AG** | *T--- | -- | 15 |
| 42 | -A--- | -CGC- | C---A | TACC- | ----- | -- | 10 |
| 43 | GCA-G | GACT- | T---T | GAG** | *T--- | -- | 17 |
| 44 | GCAA- | -AGT- | T-GAC | -AG** | *T--- | -- | 17 |

For consensus sequence E6-18-1(b), the lowest match with HPV 18, HPV 45 and HPV 59 is 24 out of the 27 bases; the highest match for HPV 6, HPV 11, HPV 42, HPV 43 and HPV 44 is 15 out of 27. For consensus sequence E6-18-1(c), the lowest match with HPV 39, HPV 68 and HPV 70 is 26 out of the 27 bases; the highest match for HPV 6, HPV 11, HPV 42, HPV 43 and HPV 44 is 17 out of 27.

Region E6-18-2(a) [Starting at Nucleotide 228] (SEQ ID NOS 95-105, respectively in order of appearance)

| 18 | ACAGA | GGTAT | TTGAA | TTTGC | mismatches |
|---|---|---|---|---|---|
| 45 | ----- | ----- | A-C-- | ----- | 2 |
| 39 | --C-- | ----- | A---- | ----- | 2 |
| 68 | ----- | ----- | A---- | ----- | 1 |
| 70 | ----- | ----- | A---- | ----- | 1 |
| 59 | -G--- | ----- | ----- | ----- | 1 |
| 6  | G---- | -AAT- | A-TC- | -A--- | 8 |
| 11 | G---- | -A--- | A--C- | -A--- | 5 |
| 42 | G---- | GG-GC | -C-CG | -ACCA | 12 |
| 43 | --G-- | A---- | -ATCG | ----- | 6 |
| 44 | AA-TC | TGG-C | G-TC- | G---- | 14 |

Potential Consensus E6-18-2(b) (SEQ ID NOS 106-117, respectively in order of appearance)

|    | ACAGA | GGTAT | ATGAA | TTTGC | mismatches |
|---|---|---|---|---|---|
| 18 | ----- | ----- | T---- | ----- | 1 |
| 45 | ----- | ----- | --C-- | ----- | 1 |
| 39 | --C-- | ----- | ----- | ----- | 1 |
| 68 | ----- | ----- | ----- | ----- | 0 |
| 70 | ----- | ----- | ----- | ----- | 0 |
| 59 | -G--- | ----- | T---- | ----- | 2 |
| 6  | G---- | -AAT- | --TC- | -A--- | 7 |
| 11 | G---- | -A--- | ---C- | -A--- | 4 |
| 42 | G---- | GG-GC | TC-CG | -ACCA | 13 |
| 43 | --G-- | A---- | TATCG | ----- | 7 |
| 44 | AA-TC | TGG-C | G-TC- | G---- | 12 |

For consensus sequence E6-18-2(b), the lowest match with HPV 18, HPV 45, HPV 39, HPV 68, HPV 70 and HPV 59 is 18 out of the 20 bases; the highest match for HPV 6, HPV 11, HPV 42, HPV 43 and HPV 44 is 16 out of 20.

Region E6-18-3(a) [Starting at Nucleotide 331] (SEQ ID NOS 118-123, respectively in order of appearance)

| 18 | GAGAA | TTAAG | ACATT | ATTCA | GACTC | TGTGT | ATG | mismatches |
|---|---|---|---|---|---|---|---|---|
| 45 | ----- | ----- | -T--- | ----- | A---- | ---A- | --- | 3 |
| 39 | -G--G | C--C- | -T--- | -C--G | ----- | G---- | --- | 8 |
| 68 | -G--- | C--C- | -T--- | -C--- | --A-- | G---- | --- | 7 |
| 70 | -G--- | C--C- | G---- | ----G | A---- | G---- | --- | 7 |
| 59 | ----- | ----- | -T--- | ---G- | ----- | C---- | --- | 3 |

Potential Consensus E6-18-3(b) (SEQ ID NOS 124-132, respectively in order of appearance)

|    | GAGAA | TTAAG | ATATT | ATTCA | GACTC | TGTGT | ATG | mismatches |
|---|---|---|---|---|---|---|---|---|
| 18 | ----- | ----- | -C--- | ----- | ----- | ----- | --- | 1 |
| 45 | ----- | ----- | ----- | ----- | A---- | ---A- | --- | 2 |
| 59 | ----- | ----- | ----- | ---G- | ----- | C---- | --- | 2 |
| 6  | ACC-- | -AT-- | -C-C- | T-GAT | T-TG- | --GA- | --- | 16 |
| 11 | ACC-- | -AT-- | -C-C- | T-AAT | T-TG- | --CA- | --- | 16 |
| 42 | -T-C- | C-GC- | -C-C- | -CGA- | AGA-- | A-CA- | TTT | 19 |
| 43 | -TC-- | -AT-- | GC-C- | T-GAC | T--G- | A-CA- | --- | 16 |
| 44 | ATC-- | --T-- | GC--- | T-AAC | T--G- | G-GA- | --- | 15 |

Potential Consensus E6-18-3(c) (SEQ ID NOS 133-141, respectively in order of appearance)

|    | GGGAA | CTACG | GTATT | ACTCG | GACTC | GGTGT | ATG | mismatches |
|----|-------|-------|-------|-------|-------|-------|-----|------------|
| 39 | ----G | ----- | A---- | ----- | ----- | ----- | --- | 2 |
| 68 | ----  | ----- | A---- | ----A | --A-- | ----- | --- | 3 |
| 70 | ----- | ----- | -C--- | ----- | A---- | C---- | --- | 2 |
|  6 | ACC-- | TATA- | AC-C- | TTGAT | T-TG- | T-GA- | --- | 21 |
| 11 | ACC-- | TATA- | AC-C- | TTAAT | T-TG- | T-CA- | --- | 21 |
| 42 | -T-C- | --G-- | AC-C- | --GAA | AGA-- | A-CA- | TTT | 18 |
| 43 | -TC-- | TATA- | -C-C- | TTGAC | T--G- | A-CA- | --- | 18 |
| 44 | ATC-- | T-TA- | -C--- | TTAAC | T--G- | --GA- | --- | 16 |

For consensus sequence E6-18-3(b), the lowest match with HPV 18, HPV 45 and HPV 59 is 31 out of the 33 bases; the highest match for HPV 6, HPV 11, HPV 42, HPV 43 and HPV 44 is 18 out of 33. For consensus sequence E6-18-3(c), the lowest match with HPV 39, HPV 68 and HPV 70 is 30 out of the 33 bases; the highest match for HPV 6, HPV 11, HPV 42, HPV 43 and HPV 44 is 17 out of 33.

A single consensus probe or primer can also be designed using either universal or degenerate bases. To preserve the highest level of discrimination, degenerate bases are preferred over universal bases.

Potential Consensus E6-18-3(d) [Using Degenerate Base "P" for C and T and Using Degenerate Bases "K" for A and G] (SEQ ID NOS 142-153, respectively in order of appearance)

|    | GKGAA | PTACG | ATATT | APTCK | KACTC | TGTGT | ATG | mismatches |
|----|-------|-------|-------|-------|-------|-------|-----|------------|
| 18 | ----- | ---A- | -C--- | ----- | ----- | ----- | --- | 2 |
| 45 | ----- | ---A- | ----- | ----- | ----- | ---A- | --- | 2 |
| 39 | ----G | ----- | ----- | ----- | ----- | G---- | --- | 2 |
| 68 | ----- | ----- | ----- | ----- | --A-- | G---- | --- | 2 |
| 70 | ----- | ----- | GC--- | ----- | ----- | G---- | --- | 3 |
| 59 | ----- | ---A- | ----- | ---G- | ----- | C---- | --- | 3 |
|  6 | ACC-- | -ATA- | -C-C- | T-GAT | T-TG- | --GA- | --- | 17 |
| 11 | ACC-- | -ATA- | -C-C- | T-AAT | T-TG- | --CA- | --- | 17 |
| 42 | -T-C- | --G-- | -C-C- | --GA- | -GA-- | A-CA- | TTT | 15 |
| 43 | -TC-- | -ATA- | GC-C- | T-GAC | T--G- | A-CA- | --- | 17 |
| 44 | ATC-- | --TA- | GC--- | T-AAC | T--G- | G-GA- | --- | 16 |

Degenerate bases are used in 5 different sites and the lowest match for consensus E6-18-3(d) with HPV 18, HPV 45, HPV 39, HPV 70, HPV 68 and HPV 59 is 30 out of the 33 bases; the highest match for consensus E6-18-3(d) with HPV 6, HPV 11, HPV 42, HPV 43 and HPV 44 is only 16 out of 33.

Region E6-18-4(a) [Starting at Nucleotide 395] (SEQ ID NOS 154-164, respectively in order of appearance)

|    | GTTAT | ACAAT | TTATT | AATAA | GGTGC | mismatches |
|----|-------|-------|-------|-------|-------|------------|
| 18 | GTTAT | ACAAT | TTATT | AATAA | GGTGC |  |
| 45 | ---G- | -T--- | --T-- | ----- | ----- | 3 |
| 39 | ----- | -T--- | ----- | ----- | ----- | 1 |

-continued

| | GTTAT | ACAAT | TTATT | AATAA | GGTGC | mismatches |
|---|---|---|---|---|---|---|
| 18 | | | | | | |
| 68 | ----- | -TG-- | ----C | ----- | ----- | 3 |
| 70 | ----- | -T--- | ----C | ----- | ----- | 2 |
| 59 | ----C | -TG-G | C-TC- | -G--- | C-C-T | 11 |
| 6 | CA-C- | TAG-C | G-TC- | ---TC | ----- | 12 |
| 11 | TA-T- | TA--A | G-T-- | ---TC | -T--T | 12 |
| 42 | T---G | -AG-A | -A-CA | ---T- | -A--T | 11 |
| 43 | AG-G- | TTG-- | --G-G | C--T- | -A--- | 11 |
| 44 | AA-TC | TGG-C | G-TC- | G---C | -C--T | 14 |

Potential Consensus E6-18-4(b) (SEQ ID NOS 165-176, respectively in order of appearance)

| | GTTAT | ATGAT | TTATT | AATAA | GGTGC | mismatches |
|---|---|---|---|---|---|---|
| 18 | ----- | -CA-- | ----- | ----- | ----- | 2 |
| 45 | ---G- | --A-- | --T-- | ----- | ----- | 3 |
| 39 | ----- | --A-- | ----- | ----- | ----- | 1 |
| 68 | ----- | ----- | ----C | ----- | ----- | 1 |
| 70 | ----- | --A-- | ----C | ----- | ----- | 2 |
| 59 | ----C | ----G | C-TC | -G--- | C-C-T | 9 |
| 6 | CA-C- | TA--C | G-TC- | ---TC | ----- | 11 |
| 11 | TA-T- | TAG-A | G-T-- | ---TC | -T--T | 13 |
| 42 | T---G | -A--A | -A-CA | ---T- | -A--T | 10 |
| 43 | AG-G- | T---- | --G-G | C--T- | -A--- | 9 |
| 44 | AA-TC | TG--C | G-TC- | G---C | -C--T | 14 |

For consensus sequence E6-184(b), the lowest match with HPV 18, HPV 45, HPV 39, HPV 68 and HPV 70 is 22 out of the 25 bases; the highest match for HPV 6, HPV 11, HPV 42, HPV 43 and HPV 44 is 15 out of 24. In this particular example, the match with HPV 59 is low (15 out of 24). This consensus sequence could be used if HPV 59 was not desired as a target. Contrariwise, if HPV 59 was desired to be a target, the E6-184(b) consensus sequence could be used after supplementation with an additional primer or probe derived from the HPV 59 sequence of the homologous region:

GTTAC ATGAG CTTCT AGTAA CGCGT

C) HPV 51 Cluster

Region E6-51-1(a) [Starting at Nucleotide 271] (SEQ ID NOS 178-186, respectively in order of appearance)

| 51 | CCATA | TGCAG | TATGC | AAACA | ATGTT | TA | mismatches |
|---|---|---|---|---|---|---|---|
| 56 | --T-- | ----- | -G--- | -G-GT | ----- | -- | 5 |
| 66 | ----- | ----- | ----T | -GGGT | ----- | -- | 5 |
| 53 | --G-- | --G-- | -G--- | ---TT | C---- | -G | 7 |
| 6 | ----- | ----- | CC--- | GCGTG | C--CC | -- | 11 |
| 11 | --C-T | ----- | CG--T | GCCTG | T--C- | -- | 12 |
| 42 | ----- | ---T- | C---T | GC-TT | T---- | -- | 8 |
| 43 | --G-T | ---T- | C---- | TTGGC | C---C | -- | 11 |
| 44 | ----T | ----- | CC-T | GCCAT | T---- | -- | 10 |

Potential Consensus E6-51-1(b) (SEQ ID NOS 187-196, respectively in order of appearance)

| | CCATA | TGCAG | TATGC | AGACT | ATGTT | TA | mismatches |
|---|---|---|---|---|---|---|---|
| 51 | ----- | ----- | ----- | -A--A | ----- | -- | 2 |
| 56 | --T-- | ----- | -G--- | ---G- | ----- | -- | 3 |
| 66 | ----- | ----- | ----T | --GG- | ----- | -- | 3 |
| 53 | --G-- | --G-- | -G--- | -A-T- | C---- | -- | 6 |
| 6 | ----- | ----- | CC--- | GCGTG | C--CC | -- | 11 |
| 11 | --C-T | ----- | CG--T | GCCTG | T--C- | -- | 12 |
| 42 | ----- | ---T- | C---T | GC-T- | T---- | -- | 8 |
| 43 | --G-T | ---T- | C---- | TTGGC | C---C | -- | 11 |
| 44 | ----T | ----- | CC--T | GCCAT | T---- | -- | 10 |

For consensus sequence E6-51-1(b), the lowest match with HPV 51, HPV 56 and HPV 66 is 24 out of the 27 bases; there are only 21 matches with HPV 53 and the highest match for HPV 6, HPV 11, HPV 42, HPV 43 and HPV 44 is 19 out of 27.

Region E6-51-2 (a) [Starting at Nucleotide 381] (SEQ ID NOS 197-205, respectively in order of appearance)

| 51 | CTTAT | ATGAT | TTATC | GATAA | CGTG | mismatches |
|---|---|---|---|---|---|---|
| 56 | G---- | G---- | ----T | A---- | ---- | 4 |
| 66 | G---- | C---- | ----T | A---- | ---- | 4 |
| 53 | G---- | C---- | ----- | A---- | ---- | 2 |
| 6 | -A-C- | TA--C | G-TC- | A--TC | ---- | 11 |
| 11 | TA-T- | TAA-A | G-T-- | A--TC | -T-- | 13 |
| 42 | T---G | -A--A | CA-CA | A--T- | -A-- | 11 |
| 43 | AG-G- | T---- | --G-G | C--T- | -A-- | 9 |
| 44 | AA-TC | TG--C | G-TC- | ----C | -C-- | 12 |

Potential Consensus E6-51-2(b) (SEQ ID NOS 206-215, respectively in order of appearance)

|    | GTTAT | ATGAT | TTATT | GATAA | GGTG  | mismatches |
|----|-------|-------|-------|-------|-------|------------|
| 51 | C---- | ----- | ----C | ----- | ----- | 2          |
| 56 | ----- | G---- | ----- | A---- | ----  | 2          |
| 66 | ----- | C---- | ----- | A---- | ----  | 2          |
| 53 | ----- | C---- | ----C | A---- | ----  | 3          |
| 6  | CA-C  | TA--C | G-TC- | A--TC | ----  | 11         |
| 11 | TA-T- | TAA-A | G-T-- | A--TC | -T--  | 12         |
| 42 | T---G | AA--A | CA-CA | A--T- | -A--  | 10         |
| 43 | AG-G- | T---- | --G-G | C--T- | -A--  | 9          |
| 44 | AA-TC | TG--C | G-TC- | ----C | -C--  | 13         |

For consensus sequence E6-51-2(b), the lowest match with HPV 51, HPV 56 and HPV 66 is 22 out of the 24 bases; there are 21 matches with HPV 53 and the highest match for HPV 6, HPV 11, HPV 42, HPV 43 and HPV 44 is 15 out of 24.

As described previously, the E6-51-2(a) region is homologous to the E6-184(a) region described previously. Due to the conservatism of this sequence, the E6-18-4(b) consensus sequence described previously could potentially be used for HPV 51, HPV 56 and HPV 66 as shown below:

Using Consensus E6-18-4 (b) from Above (SEQ ID NOS 216-219 & 848, respectively in order of appearance)

|    | GTTAT | ATGAT | TTATT | AATAA | GGTG  | mismatches |
|----|-------|-------|-------|-------|-------|------------|
| 51 | C---- | ----- | ----C | G---- | ----  | 3          |
| 56 | ----- | G---- | ----- | ----- | ----  | 1          |
| 66 | ----- | C---- | ----- | ----- | ----  | 1          |
| 53 | ----- | C---- | ----C | ----- | ----  | 2          |

For consensus sequence E6-184(b), the lowest match with HPV 51, HPV 56 and HPV 66 is 21 out of the 24 bases; as described above, the highest match for HPV 6, HPV 11, HPV 42, HPV 43 and HPV 44 is 15 out of 24

Region E6-51-3(a) [Starting at Nucleotide 477] (SEQ ID NOS 220-223, respectively in order of appearance)

|    | AATAG | CGGGA | CGTTG | GACGG | GG | mismatches |
|----|-------|-------|-------|-------|----|------------|
| 51 |       |       |       |       |    |            |
| 56 | ----- | -ACAT | G---- | ---C- | -- | 6          |
| 66 | T---- | -ATAT | GCA-- | ---C- | -- | 9          |
| 53 | ---TT | -ACAT | ATG-- | ---C- | -- | 10         |

Potential Consensus E6-51-3(b) (SEQ ID NOS 224-233, respectively in order of appearance)

|    | AATAG | CGGAT | CGTTG | GACCG | GG  | mismatches |
|----|-------|-------|-------|-------|-----|------------|
| 51 | ----- | ---GA | ----- | ---G- | --  | 3          |
| 56 | ----- | -AC-- | G---- | ----- | --  | 3          |
| 66 | T---- | -AT-- | GCA-- | ----- | --  | 6          |
| 53 | ---TT | -AC-- | ATG-- | ----- | --  | 7          |
| 6  | GC--A | ATTG- | ACG-- | --AG- | -T  | 13         |
| 11 | AC--A | ATAAC | -AG-- | --AG- | -T  | 13         |
| 42 | T---T | T-TG- | -AG-- | --CG- | -T  | 10         |
| 43 | ----C | ATAGC | GTG-- | ---A- | --  | 10         |
| 44 | -T--C | AA--- | ACC-- | --AG- | -T  | 10         |

Consensus sequence E6-51-3(b), may find use when HPV 51 and 56 are desired to be detected under conditions where HPV 66 and 53 are not desired to generate signals. The lowest match with HPV 51 and HPV 56 is 19 out of the 22 bases; HPV 66 and HPV 53 have 16 and 15 matches respectively and the highest match for HPV 6, HPV 11, HPV 42, HPV 43 and HPV 44 is 12 out of 22.

Example 2

Amplification Using Oncogenic HPV E6 Gene Sequences from Example I

A) Selection of Consensus Sequences from Example 1

|            | targets              | crossreactions |
|------------|----------------------|----------------|
| Forward    |                      |                |
| E6-16-1(b) | 16, 33, 52, 58       |                |
| E6-16-1(c) | 31 and 35            |                |
| E6-18-1(b) | 18, 45 and 59        |                |
| E6-18-1(c) | 39 and 68            | 70             |
| E6-51-1(b) | 51 and 56            | 66             |
| Reverse    |                      |                |
| E6-16-2(c) | 16, 31, 33, 35, 52 and 58 |           |
| E6-18-3(b) | 18, 45 and 59        |                |
| E6-18-3(c) | 39 and 68            | 70             |
| E6-51-2(b) | 51 and 56            | 53 and 66      |

B) Selection of Consensus Sequences from Consensus Sequences of Example 1
Forward Primer Sequences

| Primer FP-1 | TCTAA AATAA GTGAG TATAG ACATT AT (SEQ ID NO: 234) |
|---|---|
| Source | E6-16-1(b) |
| targets | 16, 33, 52 and 58 |
| minimal target match | 25 out of 27 |
| maximal non-target match | 20 out of 27 |
| Theoretical Tm | 64° C. |
| Primer FP-2 | TCAAA AGTAA GTGAA TATAG ATGGT AT (SEQ ID NO: 235) |

```
Source                      E6-16-1(c)
targets                     31 and 35
minimal target match        26 out of 27
maximal non-target match    17 out of 27
Theoretical Tm              68° C.

Primer FP-3                 CGACC CTACA AACTA CCTGA
                            TTTTG CA (SEQ ID NO: 236)
Source                      E6-18-1(b)
targets                     18,45 and 59
minimal target match        24 out of 27
maximal non-target match    15 out of 27
Theoretical Tm              78° C.

Primer FP-4                 CATAC AAATT GCCAG ACCTT
                            GCA (SEQ ID NO: 237)
Source                      E6-18-1(c)
targets                     39 and 68
minimal target match        22 out of 23
maximal non-target match    14 out of 23
Theoretical Tm              66° C.

Primer FP-5                 CCATA TGCAG TATGC AGACT
                            ATGTT TA (SEQ ID NO: 238)
Source                      E6-51-1(b)
targets                     51 and 56
minimal target match        24 out of 27
maximal non-target match    19 out of 27
Theoretical Tm              74° C.
```

Reverse Primer Sequences

```
Primer RP-1                 GGACA CAAPG GPPTT TGACA
                            KKTAA TACAC CTAAT
                            (SEQ ID NO: 239)
Source                      E6-16-2(c)
targets                     16, 31, 33, 35, 52 and 58
minimal target match        31 out of 35
maximal non-target match    25 out of 35
Theoretical Tm              80° C.

Primer RP-2                 CATAC ACAGT GTCTG AATAA
                            TATCT AA (SEQ ID NO: 240)
Source                      E6-18-3(b)
targets                     18, 45 and 59
minimal target match        26 out of 28
maximal non-target match    16 out of 28
Theoretical Tm              72° C.

Primer RP-3                 CATAC ACCGA GTCCG AGTAA
                            TACCG TAG (SEQ ID NO: 241)
Source                      E6-18-3(c)
targets                     39 and 28
minimal target match        25 out of 28
maximal non-target match    15 out of 28
Theoretical Tm              84° C.

Primer RP-4                 CCCGG TCCAA CGATC CGCTA TT
                            (SEQ ID NO: 242)
Source                      E6-51-2(b)
targets                     51 and 56
minimal target match        20 out of 22
maximal non-target match    13 out of 22
Theoretical Tm              70° C.
```

The primers listed above may be used as a single mixture or in various combinations. They may be used in PCR reactions or modifications can be made to them for use in other amplification systems. For example, restriction enzyme sites can be added for the purpose of carrying out SDA and phage promoter sequences can be added for carrying out NASBA. Detection of amplification products can be carried out by any of various methods that have been described in the literature. These can include post-synthesis detection as well as real-time detection.

Example 3

Selection of Conserved Differential Sequences from the E7 Gene

A) HPV 16 Cluster

Region E7-16-1(a) [Starting at Nucleotide 617] (SEQ ID NOS 243-252, respectively in order of appearance)

| 16 | CAACT | GATCT | CTACT | GTTAT | GAGCA | ATT | mismatches |
|---|---|---|---|---|---|---|---|
| 35 | ----- | --C-- | A---- | ----- | ----- | --- | 2 |
| 31 | ----- | --C-- | -C--- | ----- | ----- | --- | 2 |
| 52 | ----- | --C-- | AC--- | -C--- | ----- | --- | 4 |
| 33 | ----- | --C-- | A---- | -C--- | ----- | --- | 3 |
| 58 | ----- | --C-- | A-T-- | -C--- | ----- | --- | 4 |
| 6  | -TGTA | -GGT- | AC-T- | -C--- | ----- | --- | 11 |
| 11 | -TGTA | -GGT- | AC-T- | -C--- | ----- | --- | 11 |
| 42 | -CAT- | --C-- | G--T- | -C--- | --A-- | --- | 8 |
| 44 | -TGTA | -GC-- | AC-T- | -CA-- | ----- | --- | 11 |

Potential Consensus E7-16-1(b) (SEQ ID NOS 253-263, respectively in order of appearance)

|    | CAACT | GACCT | CTACT | GCTAT | GAGCA | ATT | mismatches |
|---|---|---|---|---|---|---|---|
| 16 | ----- | --T-- | ----- | -T--- | ----- | --- | 2 |
| 35 | ----- | ----- | A---- | -T--- | ----- | --- | 2 |
| 31 | ----- | ----- | -C--- | -T--- | ----- | --- | 2 |
| 52 | ----- | ----- | AC--- | ----- | ----- | --- | 2 |
| 33 | ----- | ----- | A---- | ----- | ----- | --- | 1 |
| 58 | ----- | ----- | A-T-- | ----- | ----- | --- | 2 |
| 6  | -TGTA | -GGT- | AC-T- | ----- | ----- | --- | 10 |
| 11 | -TGTA | -GGT- | AC-T- | ----- | ----- | --- | 10 |
| 42 | -CAT- | ----- | G--T- | ----- | --A-- | --- | 6 |
| 44 | -TGTA | -G--- | AC-T- | --A-- | ----- | --- | 9 |

For consensus sequence E7-16-1(b), the lowest match with HPV 16, HPV 31, HPV 33, HPV 35, HPV 52 and HPV 58 is 26 out of the 28 bases; the highest match for HPV 6, HPV 11, HPV 42 and HPV 44 is 22 out of 28. Also note that part of this region corresponds to a sequence used by Evander and Waddell (1991) for a general consensus primer for low risk as well as high risk HPV starting with position 636 of HPV Region E7-16-2(a) [Starting at Nucleotide 649] (SEQ ID NOS 264-273, respectively in order of appearance)

| 16 | GACAG | CTCAG | AGGAG | GAGGA | mismatches |
|----|-------|-------|-------|-------|------------|
| 35 | ----- | ----- | ----- | ----- | 0 |
| 31 | ----- | ----- | -T--- | ----- | 1 |
| 52 | ----- | ----- | -T--- | ----- | 1 |
| 33 | ----- | ----- | -T--- | --T-- | 2 |
| 58 | ----- | ----- | -C--- | --T-- | 2 |
| 6  | ----- | ----- | -A--T | ----T | 3 |
| 11 | ----- | ----- | -A--T | ----T | 3 |
| 42 | ----- | ----- | -T--A | --T-- | 3 |
| 44 | ----- | ----- | -A--- | --T-- | 2 |

For HPV 16 sequence E7-16-2(a), the lowest match with HPV 16, HPV 31, HPV 33, HPV 35, HPV 52 and HPV 58 is 18 out of the 20 bases; the highest match for HPV 6, HPV 11, HPV 42 and HPV 44 is 18 out of 20.

Even though the differences between target and homologous non-target sequences are similar, the conserved nature of this sequence may still allow the use of the E7-16-2(a) region to find use as part of a design of a pair of amplification primers, where the other primer or primers provides discrimination. For instance, one of the E6-16 regions described in Example 1 could be used to design a forward primer and the E7-16-2(a) region could be used for design of a reverse primer. This primer set should be much more efficient for amplification by target templates than non-target template sequences. Further maintenance of discrimination can be achieved by the use of probes that provide signal generation specificity for target amplicon sequences.

B) HPV 18 Cluster

Region E7-18-1(a) [Starting at Nucleotide 656] (SEQ ID NOS 274-283, respectively in order of appearance)

| 18 | GTTGA | CCTTC | TATGT | CACGA | GCAAT | T | mismatches |
|----|-------|-------|-------|-------|-------|---|------------|
| 39 | ----- | ----G | ----- | ----- | ----- | - | 1 |
| 45 | ----- | ---GT | -G--- | T---- | ----- | - | 4 |
| 59 | ----- | ----G | -G--C | T---- | ----- | - | 4 |
| 68 | --C-- | ----G | ----- | ----- | ----- | - | 2 |
| 70 | --C-- | ----G | ----- | ----- | ----- | - | 2 |
| 6  | --A-G | GT-A- | AT--C | T-T-- | ----- | - | 10 |
| 11 | --A-G | GT-A- | AT--C | T-T-- | ----- | - | 10 |
| 42 | A---- | ---GT | AT--C | T-T-- | A---- | - | 9 |
| 44 | --A-G | GT-A- | AT--C | A-T-- | ----- | - | 10 |

Potential Consensus E7-18-1(b) (SEQ ID NOS 284-294, respectively in order of appearance)

| | GTTGA | CCTTC | TATGT | TACGA | GCAAT | T | mismatches |
|----|-------|-------|-------|-------|-------|---|------------|
| 18 | ----- | ----C | ----- | C---- | ----- | - | 2 |
| 39 | ----- | ----- | ----- | C---- | ----- | - | 1 |
| 45 | ----- | ----GT | -G--- | ----- | ----- | - | 3 |
| 59 | ----- | ----- | -G--C | ----- | ----- | - | 2 |
| 68 | --C-- | ----- | ----- | C---- | ----- | - | 2 |
| 70 | --C-- | ----- | ----- | C---- | ----- | - | 2 |
| 6  | --A-G | GT-AC | AT--C | --T-- | ----- | - | 10 |
| 11 | --A-G | GT-AC | AT--C | --T-- | ----- | - | 10 |
| 42 | A---- | ---GT | AT--C | --T-- | A---- | - | 8 |
| 44 | --A-G | GT-AC | AT--C | A-T-- | ----- | - | 11 |

For consensus sequence E7-18-1(b), the lowest match with HPV 18, HPV 39, HPV 45, HPV 59, HPV 68 and HPV 70 is 23 out of 26 bases; the highest match for HPV 6, HPV 11, HPV 42, HPV 43 and HPV 44 is 18 out of 26.

Region E7-18-2(a) [Starting at Nucleotide 689] (SEQ ID NOS 295-304, respectively in order of appearance)

| 18 | TCAGAGGAAG | AAAACGATGAAATAGATGGAGTTA | mismatches |
|----|------------|--------------------------|------------|
| 45 | --------G- | ------------CC---------- | 3 |
| 39 | --------T- | ---TA------CCC--CCAT-CAG | 12 |
| 68 | -----C--T- | ---TA------CCC--CCAT-CAG | 13 |
| 70 | -----CA-T- | ---CA------CCC--CCAT--AG | 14 |
| 59 | --C---A-T- | ----A------CC----------- | 6 |
| 6  | -----A---- | ---TG--C---G-G---------- | 6 |
| 11 | -----A---- | ---TG--CA-GG-G---A------ | 10 |
| 44 | -----A---- | ---TG------C---C-ACG---- | 8 |
| 42 | -----T---- | -TG-CC-A-CC-A-C-G-ACA-AC | 16 |

Potential Region E7-18-2(b) (SEQ ID NOS 305-315, respectively in order of appearance)

| | TCAGAGGAAG | AAAACGATGAAACAGATGGAGTTA | mismatches |
|----|------------|--------------------------|------------|
| 18 | ---------- | ------------T----------- | 1 |
| 45 | --------G- | ------------C----------- | 2 |
| 39 | --------T- | ---TA------C-C--CCAT-CAG | 12 |
| 68 | -----C--T- | ---TA------C-C--CCAT-CAG | 13 |
| 70 | -----CA-T- | ---CA------C-C--CCAT--AG | 13 |
| 59 | --C---A-T- | ----A------C----------- | 5 |
| 6  | -----A---- | ---TG--C---GTG---------- | 7 |

-continued

| | TCAGAGGAAG | AAAACGATGAAACAGATGGAGTTA | mismatches |
|---|---|---|---|
| 11 | -----A---- | ---TG--CA-GGTG---A------- | 10 |
| 44 | -----A---- | ---TG------CT--C-ACG----- | 9 |
| 42 | -----T---- | -TG--C-A-CC-A-C-G-ACA-AC | 15 |

Potential Region E7-18-2(c) (SEQ ID NOS 316-326, respectively in order of appearance)

| | TCAGACGATG | AAACAGATGAACCCGACCATGCAG | mismatches |
|---|---|---|---|
| 18 | -----G--A- | ---AC------ATA--TGGA-TTA | 14 |
| 45 | -----G--G- | ---AC--------A--TGGA-TTA | 12 |
| 39 | -----G---- | ---T-------------------- | 2 |
| 68 | ---------- | ---T-------------------- | 1 |
| 70 | ------A--- | --------------------T-- | 2 |
| 59 | --C--GA--- | ---A---------A--TGGA-TTA | 12 |
| 6 | -----A--A- | ---TG--C---GTG--TGGA-TTA | 15 |
| 11 | -----A--A- | ---TG--CA-GGTG--TAGA-TTA | 17 |
| 44 | -----A--A- | ---TG-------TA-CTACG-TTA | 14 |
| 42 | -----T--A- | -TGACC-A-CCAAAC-GGACATAC | 22 |

For consensus sequence E7-18-2(b), the lowest match with HPV 18 and HPV 45 is 32 out of 34 bases; the highest match for HPV 6, HPV 11, HPV 42, HPV 43 and HPV 44 is 27 out of 34. For consensus sequence E7-18-2(c), the lowest match with HPV 39, HPV 68 and HPV 70 is 32 out of the 34 bases; the highest match for HPV 6, HPV 11, HPV 42, HPV 43 and HPV 44 is 20 out of 34. For HPV 59, the degree of matching is depending upon which portion of E7-18-2 is used and thereby dependent upon whether the sequence is being used to design a) a probe b) a forward primer going rightwards or c) a reverse primer going leftwards and whether it is desired to generate a signal or not with HPV 59.

C) HPV 51 Cluster

Region E7-51-1(a) [Starting at Nucleotide 619] (SEQ ID NOS 327-334, respectively in order of appearance)

| 51 | GAAAT | TGACT | TGCAA | TGCTA | CGAGC | AATT | mis-matches |
|---|---|---|---|---|---|---|---|
| 56 | ----- | ----C | -A--G | ---A- | T---- | ---- | 5 |
| 66 | ----- | ----C | -A--- | ---A- | T---- | ---- | 4 |
| 53 | --G-- | ----C | ----- | ---C- | T---- | ---- | 4 |
| 6 | CCTG- | A-GG- | -A--T | ----- | T---- | ---- | 10 |
| 11 | CCTG- | A-GG- | -A--T | ----- | T---- | ---- | 10 |
| 42 | CCC-- | ----C | --T-T | ----- | T--A- | ---- | 8 |
| 44 | CCTG- | A-G-C | -A--T | ---A- | T---- | ---- | 11 |

Potential Consensus E7-51-1(b) (SEQ ID NOS 335-343, respectively in order of appearance)

| | GAAAT | TGACT | TACAA | TGCAA | CGAGC | AATT | mis-matches |
|---|---|---|---|---|---|---|---|
| 51 | ----- | ----- | -G--- | ---T- | ----- | ---- | 2 |
| 56 | ----- | ----C | ----G | ----- | T---- | ---- | 3 |
| 66 | ----- | ----C | ----- | ----- | T---- | ---- | 2 |
| 53 | --G-- | ----C | -G--- | ---C- | T---- | ---- | 5 |
| 6 | CCTG- | A-GG- | ----T | ---T- | T---- | ---- | 10 |
| 11 | CCTG- | A-GG- | ----T | ---T- | T---- | ---- | 10 |
| 42 | CCC-- | ----C | -GT-T | ---T- | T--A- | ---- | 10 |
| 44 | CCTG- | A-G-C | -A--T | ----- | T---- | ---- | 10 |

For consensus sequence E7-51-1(b), the lowest match with HPV 51, HPV 56 and HPV 66 is 22 out of the 24 bases; there are 21 matches with HPV 53 and the highest match for HPV 6, HPV 11, HPV 42, HPV 43 and HPV 44 is 15 out of 24.

Region E7-51-2(a) [Starting at Nucleotide 649] (SEQ ID NOS 344-351, respectively in order of appearance)

| 51 | GACAG | CTCAG | AGGAG | GAGGA | TGA | mismatches |
|---|---|---|---|---|---|---|
| 56 | ----- | ----- | ----T | ----- | --- | 1 |
| 66 | ----- | ----- | ----T | ----- | --- | 1 |
| 53 | A---- | ----- | ----T | ----- | --- | 2 |
| 6 | ----- | ----- | -A--T | ----T | G-- | 4 |
| 11 | ----- | ----- | -A--T | ----T | G-- | 4 |
| 42 | ----- | ----- | -T--A | --T-- | G-- | 4 |
| 44 | ----- | ----- | -A--- | ----T | G-- | 3 |

For sequence E7-51-2(a), the lowest match with HPV 51, HPV 56 and HPV 66 is 22 out of the 23 bases; there are 21 matches with HPV 53 and the highest match for HPV 6, HPV 11, HPV 42, HPV 43 and HPV 44 is 20 out of 23. It should be noted that although the HPV 53 has only two mismatches with the sequence above, the effectiveness of a primer using HPV 53 as a template can be determined by the design of a primer. For instance, a primer that had the sequence TCATC-CTCCTCCTCTGAGCTGT (SEQ ID NO: 846) would only have a single mismatch with the HPV 53 sequence and this would be in the middle of the primer; consequently it could be used to effectively amplify HPV 53 sequences. On the other hand, the sequence TCATCCTCCTCCTCTGAGCTGTC (SEQ ID NO: 847) would have two mismatches, with one of them being at the 3' end; this is a much more serious mismatch and should reduce the efficiency of extension using HPV 53 as a template. It should also be noted that the first 20 bases of this sequence are identical to the E7-16-2(b) region described previously. As such, if the E7-16-2(b) sequence was used for a primer design it would cover HPV 51, 56 and 66 as well, eliminating the need for a separate primer for these types.

Region E7-51-3(a) [Starting at Nucleotide 701] (SEQ ID NOS 352-355, respectively in order of appearance)

| 51 | AGACG | GGCTG | GACAG | GCTAC | GTGTT | AC | mismatches |
|----|-------|-------|-------|-------|-------|-----|------------|
| 56 | ----A | A---A | A---A | CA--- | ----- | -- | 7 |
| 66 | ----A | A---A | A---A | CA--A | ----- | -- | 8 |
| 53 | ----- | --AC- | A---A | CA-C- | T---- | -- | 8 |

Potential Consensus E7-51-3(b) (High Mismatch with HPV 53) (SEQ ID NOS 356-364, respectively in order of appearance)

|    | AGACG | AGCTA | GACAA | GCTAC | GTGTT | AC | mismatches |
|----|-------|-------|-------|-------|-------|-----|------------|
| 51 | ----- | G---G | ----G | ----- | ----- | -- | 3 |
| 56 | ----A | ----- | A---- | CA--- | ----- | -- | 4 |
| 66 | ----A | ----- | A---- | CA--A | ----- | -- | 5 |
| 53 | ----- | G-ACG | A---- | CA-C- | T---- | -- | 9 |
| 6  | CA--C | TTTA- | A---- | CA*** | ***-- | -- | 16 |
| 11 | CA--C | TTTA- | C---- | CA*** | ***-- | -- | 16 |
| 42 | -A--A | G-AC- | T---G | CG*** | ***-- | -- | 15 |
| 44 | CA-GA | C-T-- | C---G | C-*** | ***-- | -- | 15 |

For consensus sequence E7-51-3(b), the lowest match with HPV 51 and HPV 56 is 23 out of the 27 bases; there are 22 matches with HPV 66; there are 21 matches with HPV 53 and the highest match for HPV 6, HPV 11, HPV 42, HPV 43 and HPV 44 is 14 out of 27.

Example 4

Primers and Probes from E6 Conserved Differential Sequences from Example 1 and Primers from E7 Conserved Differential Sequences from Example 3

Selection of Consensus Sequences from Examples 1 and 3

|  | targets | crossreactions |
|---|---|---|
| Forward Primers | | |
| E6-16-1(b) | 16, 33, 52, and 58 | |
| E6-16-1(c) | 31 and 35 | |
| E6-18-1(b) | 18, 45 and 59 | |
| E6-18-1(c) | 39 and 68 | 70 |
| E6-51-1(b) | 51 and 56 | 66 |
| (2) Reverse Primers | | |
| E7-16-1(b) | 16, 31, 33, 35, 52 and 58 | |
| E7-18-1(b) | 18, 39, 45, 59 and 68 | 70 |
| E7-51-1(b) | 51 and 56 | 66 |
| (3) Probes | | |
| E6-16-2(c) | 16, 31, 33, 35, 52 and 58 | |
| E6-18-3(d) | 18, 45, 59, 39, and 68 | 70 |
| E6-51-3(b) | 51 and 56 | |

B) Selection of Primer Sequences from Examples 1 and 3

(1) Forward Primer Sequences are as described in Example 2 (i.e. Primers FP-1, FP-2, FP-3, FP-4 and FP-5)

(2) Reverse Primer Sequences

| Primer RP-11 | TGCTC ATAGC AGTAG AGGTC AGTTG (SEQ ID NO: 365) |
|---|---|
| Source | E7-16-1(b) |
| targets | 16, 31, 33, 35, 52 and 58 |
| minimal target match | 23 out of 25 |
| maximal non-target match | 19 out of 25 |
| Theoretical Tm | 74° C. |
| Primer RP-12 | AATTG CTCGT AACAT ACAAG GTCAA C (SEQ ID NO:366) |
| Source | E7-18-1(b) |
| targets | 18, 39, 45, 59 and 68 |
| minimal target match | 23 out of 26 |
| maximal non-target match | 18 out of 26 |
| Theoretical Tm | 72° C. |
| Primer RP-13 | AATTG CTCGT TGCAT TGTAA GTCAA TTTC (SEQ ID NO: 367) |
| Source | E7-51-1(b) |
| targets | 51 and 56 |
| minimal target match | 26 out of 29 |
| maximal non-target match | 19 out of 29 |
| Theoretical Tm | 78° C. |

Probe Sequences

| Probe Pro-11 | ATTAG GTGTA TTAPP TGTCA AAKKC CKTTG TGTCC (SEQ ID NO: 368) |
|---|---|
| Source | E6-16-2(c) |
| targets | 16, 31, 33, 35, 52 and 58 |
| minimal target match | 31 out of 35 |
| maximal non-target match | 25 out of 35 |
| Theoretical Tm | 82° C. |
| Probe Pro-12 | GKGAA PTACG ATATT APTCK KACTC TGTGT ATG (SEQ ID NO: 369) |
| Source | E6-18-3(d) |
| targets | 18, 39, 45, 59 and 68 |
| minimal target match | 30 out of 33 |
| maximal non-target match | 17 out of 33 |
| Theoretical Tm | 76° C. |
| Probe Pro-13 | ATTAG CGGAT CGTTG GACCG GG (SEQ ID NO: 370) |
| Source | E6-51-3(b) |
| targets | 51 and 56 |
| minimal target match | 19 out of 22 |
| maximal non-target match | 12 out of 22 |
| Theoretical Tm | 70° C. |

Example 5

Primers from E6 Conserved Differential Sequences from Example 1 and Primers and Probes from E7 Conserved Differential Sequences from Example 3

Selection of Consensus Sequences from Examples 1 and 3

|  | targets | crossreactions |
|---|---|---|
| (1) Forward Primers |  |  |
| E6-16-1(b) | 16, 31, 33, 52, 58 |  |
| E6-16-1(c) | 31 and 35 |  |
| E6-18-1(b) | 18, 45 and 59 |  |
| E6-18-1(c) | 39 and 68 | 70 |
| E6-51-1(b) | 51 and 56 | 66 |
| (2) Reverse Primers |  |  |
| E7-16-2(a) | 16, 31, 33, 35, 51, 52, 56 and 58 | 6, 11, 42, 43, 44 and 66 |
| E7-18-2(b) | 18, 45 and 59 |  |
| E7-18-2(c) | 39 and 68 | 70 |
| (3) Probes |  |  |
| E7-16-1(b) | 16, 31, 33, 35, 52 and 58 |  |
| E7-18-1(b) | 18, 39, 45, 59 and 68 | 70 |
| E7-51-1(b) | 51 and 56 | 66 |

As noted above, one of the Reverse primers (from the E7-16-2(a) sequence) has extended breadth. Although selected from an HPV 16 sequence, it will also be able to use the more distantly related HPV 51 and HPV 56 genomic sequences as targets for binding/extension events. On the other hand, this breadth will also allow extension with non-target HPV types (6, 11, 42, 43, and 44) as templates if present in a sample. However, due to the specificity of the Forward primers there should be low efficiency at best for amplification of such non-targets. Additionally, specificity of signal generation should be strengthened by the properties of the probes used in this example.

B) Selection of Primer Sequences from Examples 1 and 3
(1) Forward Primer Sequences are as Described in Example 2 (i.e. Primers FP-1, FP-2, FP-3, FP4 and FP-5)
(2) Reverse Primer Sequences

```
Primer RP-21              TCCTC CTCCT CTGAG CTGTC
                          (SEQ ID NO: 371)
Source                    E7-16-2(a)
targets                   16, 31, 33, 35, 51, 52, 56
                          and 58
minimal target match      18 out of 20
maximal non-target match  18 out of 20
Theoretical Tm            64° C.

Primer RP-22              TAACT CCATC TGTTT CATCG
                          TTTTC (SEQ ID NO: 372)
Source                    E7-18-2(b)
targets                   18, 45 and 59
minimal target match      23 out of 25
maximal non-target match  19 out of 25
Theoretical Tm            68° C.

Primer RP-23              CTGCA TGGTC GGGTT CATCT
                          GTTTC AT (SEQ ID NO: 373)
Source                    E7-18-2(c)
targets                   39 and 68
minimal target match      26 out of 27
maximal non-target match  14 out of 27
Theoretical Tm            80° C.
```

(3) Probe Sequences

```
Probe Pro-21              CAACT GACCT CTACT GCTAT
                          GAGC (SEQ ID NO: 374)
Source                    E7-16-1(b)
targets                   16, 31, 33, 35, 52 and 58
minimal target match      22 out of 24
maximal non-target match  18 out of 24
Theoretical Tm            72° C.

Probe Pro-22              GTTGA CCTTG TATGT TACGA
                          GCAAT T (SEQ ID NO:375)
Source                    E7-18-1(b)
targets                   18, 39, 45, 59 and 68
minimal target match      23 out of 26
maximal non-target match  18 out of 26
Theoretical Tm            72° C.

Probe Pro-23              GAAAT TGACT TACAA TGCAA
                          CGAGC AATT (SEQ ID NO:
                          376)
Source                    E7-51-1(b)
targets                   51 and 56
minimal target match      26 out of 29
maximal non-target match  19 out of 29
Theoretical Tm            78° C.
```

Example 6

Selection of Conserved Differential Sequences from the E1 Gene

HPV 16 Cluster
Region E1-16-1(a) [starting at nucleotide 865] (SEQ ID NOS 377-386, respectively in order of appearance)

| 16 | ATGGC | TGATC | CTGCA | GGTAC | mismatches |
|---|---|---|---|---|---|
| 35 | ----- | ----- | ----- | ----- | 0 |
| 31 | ----- | ----- | -A--- | ----- | 1 |
| 52 | ----A | G--C- | ---A- | ----- | 4 |
| 33 | ----- | C---- | ---A- | ----- | 2 |
| 58 | ----A | ---C- | ---A- | ----- | 3 |
| 6  | ----- | ---CG | A-T-- | ----- | 4 |
| 11 | ----- | ---CG | A-T-- | ----- | 4 |
| 42 | ----- | ---CA | A-A-- | ----- | 4 |
| 44 | ----- | G---G | A-A-- | ----- | 4 |

Potential Region E1-16-1(b) (SEQ ID NOS 387-397, respectively in order of appearance)

|    | ATGGA | CGACC | CTGAA | GGTAC | mismatches |
|----|-------|-------|-------|-------|------------|
| 16 | ----C | T--T- | ---C- | ----- | 4 |
| 35 | ----C | T--T- | -A-C- | ----- | 5 |
| 31 | ----C | T--T- | ---C- | ----- | 4 |
| 52 | ----- | G---- | ----- | ----- | 1 |
| 33 | ----C | ---T- | ----- | ----- | 2 |
| 58 | ----- | T---- | ----- | ----- | 1 |
| 6  | ----C | T---G | A-TC- | ----- | 6 |
| 11 | ----C | T---G | A-TC- | ----- | 6 |
| 42 | ----C | T---A | A-AC- | ----- | 6 |
| 44 | ----C | T--TG | A-AC- | ----- | 7 |

For consensus sequence E1-16-1(a), the lowest match with HPV 16, HPV 31, HPV 33 and HPV 35 is 18 out of the 20 bases; the highest match for HPV 6, HPV 11, HPV 42 and HPV 44 is 16 out of 20. For consensus sequence E1-16-1(b), the lowest match with HPV 52 and HPV 58 is 19 out of the 20 bases; the highest match for HPV 6, HPV 11, HPV 42 and HPV 44 is 14 out of 20.

Region E1-16-2(a) [Starting at Nucleotide 1057] (SEQ ID NOS 398-403, respectively in order of appearance)

|    | GAGAC | AGCAC | ATGCG | TTGTT | TACTG | CACAG | GA | mismatches |
|----|-------|-------|-------|-------|-------|-------|-----|----|
| 16 |       |       |       |       |       |       |     |    |
| 35 | ----- | ----- | -A--A | ----- | -CA-- | ----- | -- | 4 |
| 31 | ----- | ----- | -G--A | ----- | -CA-- | ----- | -- | 4 |
| 52 | ---G- | ---C- | GG--A | ----- | --A-- | ----- | -- | 6 |
| 33 | ---G- | ---C- | GG--A | ----- | --A-A | T---- | -- | 8 |
| 58 | ---G- | ---C- | GA--- | ----- | --A-- | T---- | -- | 6 |

Potential Consensus E1-16-2(b) (SEQ ID NOS 404-414, respectively in order of appearance)

|    | GAGAC | AGCAT | ATGCA | TTGTT | TAATG | CACAG | GA | mismatches |
|----|-------|-------|-------|-------|-------|-------|-----|----|
| 16 | ----- | ----- | ----G | ----- | --C-- | ----- | -- | 2 |
| 35 | ----- | ----- | -A--- | ----- | -C--- | ----- | -- | 2 |
| 31 | ----- | ----- | -G--- | ----- | -C--- | ----- | -- | 2 |
| 52 | ---G- | ---C- | GG--- | ----- | ----- | ----- | -- | 4 |
| 33 | ---G- | ---C- | GG--- | ----- | ----A | T---- | -- | 6 |
| 58 | ---G- | ---C- | GA--G | ----- | ----- | T---- | -- | 6 |
| 6  | CT-GA | ----- | -G--- | ----- | ---CA | GG--- | -- | 9 |
| 11 | CT-GA | ----- | -G--- | ----- | ----A | GG--- | -- | 8 |
| 42 | CT-GA | ----- | -G---C | --A-- | A--A | A---- | CA | 12 |
| 44 | -TACA | T---- | -A--- | ----- | A--C- | AG--- | -- | 10 |

Potential Consensus E1-16-2(c) (SEQ ID NOS 415-425, respectively in order of appearance)

|    | GAGGC | AGCCT | GGGCA | TTGTT | TAATG | TACAG | GA | mismatches |
|----|-------|-------|-------|-------|-------|-------|-----|----|
| 16 | ---A- | ---A- | AT--G | ----- | --C-- | C---- | -- | 7 |
| 35 | ---A- | ---A- | AA--- | ----- | -C--- | C---- | -- | 6 |
| 31 | ---A- | ---A- | AG--- | ----- | -C--- | C---- | -- | 6 |

-continued

|  | GAGGC | AGCCT | GGGCA | TTGTT | TAATG | TACAG | GA | mismatches |
|---|---|---|---|---|---|---|---|---|
| 52 | ----- | ----- | ----- | ----- | ----- | C---- | -- | 1 |
| 33 | ----- | ----- | ----- | ----- | ----A | ----- | -- | 1 |
| 58 | ----- | ----- | -A--G | ----- | ----- | ----- | -- | 2 |
| 6 | CT--A | ---A- | A---- | ----- | ---CA | GG--- | -- | 9 |
| 11 | CT--A | ---A- | A---- | ----- | ----A | GG--- | -- | 8 |
| 42 | CT--A | ---A- | A---C | --A-- | A---A | A---- | CA | 12 |
| 44 | -TACA | T--A- | A---- | ----- | A--C- | AG--- | -- | 11 |

For consensus sequence E1-16-2(b), the lowest match with HPV 16, HPV 31 and HPV 35 is 30 out of the 32 bases; the highest match for HPV 6, HPV 11, HPV 42 and HPV 44 is 24 out of 32. For consensus sequence E1-16-2(c), the lowest match with HPV 33, HPV 52 and HPV 58 is 30 out of the 32 bases; the highest match for HPV 6, HPV 11, HPV 42 and HPV 44 is 24 out of 32.

Region E1-16-3(a) [Starting at Nucleotide 1656] (SEQ ID NOS 426-435, respectively in order of appearance)

| 16 | CAAAG | TTTAG | CATGT | TCATG | GGGAA | TGGT | mismatches |
|---|---|---|---|---|---|---|---|
| 35 | ---T- | ----T | -G--- | ----- | ---T- | ---- | 4 |
| 31 | ----- | ----- | ----- | --C-- | ---C- | ----- | 1 |
| 52 | ---T- | ----A | ----- | GACA- | A--CG | -C-- | 10 |
| 33 | ---T- | ----A | -T--C | GATA- | A---- | -AA- | 11 |
| 58 | ---T- | ----A | -G--- | GACA- | A---- | -AA- | 10 |
| 6 | ---T- | GC--A | --AA- | G---- | ----- | ----- | 7 |
| 11 | ---T- | GC-TA | --AA- | G---- | ----- | ----- | 8 |
| 42 | ---T- | GC--A | -C--- | G-G-- | ---C- | ----- | 8 |
| 44 | ---T- | GC-TA | --AA- | G---- | ----- | ----- | 8 |

Potential Consensus E1-16-3(b) (SEQ ID NOS 436-446, respectively in order of appearance)

|  | CAAAG | TTTAG | CGTGT | TCATG | GGGAA | TGGT | mismatches |
|---|---|---|---|---|---|---|---|
| 16 | ----- | ----- | -A--- | ----- | ----- | ---- | 1 |
| 35 | ---T- | ----T | ----- | ----- | ---T- | ---- | 3 |
| 31 | ----- | ----- | -A--- | --C-- | ---C- | ---- | 3 |
| 52 | ---T- | ----A | -A--- | GACA- | A--CG | -C-- | 11 |
| 33 | ---T- | ----A | -T--C | GATA- | A---- | -AA- | 11 |
| 58 | ---T- | ----A | ----- | GACA- | A---- | -AA- | 9 |
| 6 | ---T- | GC--A | -AAA- | G---- | ----- | ---- | 8 |
| 11 | ---T- | GC-TA | -AAA- | G---- | ----- | ---- | 9 |
| 42 | ---T- | GC--A | -C--- | G-G-- | ---C- | ---- | 8 |
| 44 | ---T- | GC-TA | -AAA- | G---- | ----- | ---- | 9 |

Potential Consensus E1-16-3(c) (SEQ ID NOS 447-457, respectively in order of appearance)

|  | CAATG | TTTAA | CTTGT | GACAG | AGG | mismatches |
|---|---|---|---|---|---|---|
| 16 | ---A- | ----G | -A--- | TCAT- | G-- | 8 |
| 35 | ----- | ----T | -G--- | TCAT- | G-- | 7 |
| 31 | ---A- | ----G | -A--- | TC-T- | G-- | 7 |
| 52 | ----- | ----- | -A--- | ----- | --- | 1 |
| 33 | ----- | ----- | ----C | --T-- | --- | 2 |
| 58 | ----- | ----- | -G--- | ----- | ----- | 1 |
| 6 | ----- | GC--- | -AAA- | -CAT- | G-- | 9 |
| 11 | ----- | GC-T- | -AAA- | -CAT- | G-- | 10 |
| 42 | ----- | GC--- | -C--- | -CGT- | G-- | 7 |
| 44 | ----- | GC-T- | -AAA- | -CAT- | G-- | 10 |

The theoretical Tm of Consensus E1-16-3(c) would be 64° C. Substitution of two NH$_2$-amino-dA analogues would raise the theoretical Tm to 70° C.

B) HPV 18 Cluster

Regional E1-18-1(a) [Starting at Nucleotide 926] (SEQ ID NOS 458-467, respectively in order of appearance)

| 18 | GAAGG | TACAG | ACGGG | GAGGG | mismatches |
|---|---|---|---|---|---|
| 39 | ----- | ----- | ----- | --T-- | 1 |
| 45 | ----- | ---C- | ----- | ----- | 1 |
| 59 | ----- | ----- | -T--- | --A-- | 2 |
| 68 | ----- | ----- | -T--- | --C-- | 2 |

```
18  GAAGG  TACAG  ACGGG  GAGGG     mismatches

70  -----  -----  -T---  --T--         2

6  TC---  -----  -AAAT  -----         6

11  TC---  -----  -AAAT  -----         6

42  AC---  -----  -G---  -----         3

44  AC---  -----  -G--A  AC---         6
```

For consensus sequence E1-18-1(a), the lowest match with HPV 18, HPV 45, HPV 39, HPV 59, HPV 68 and HPV 70 is 18 out of 20 bases; the highest match for HPV 6, HPV 11, HPV 42 and HPV 44 is 17 out of 20. If E1-18-1 were used as a leftwards primer, the first mismatch with the HPV 18 group would be 9 bases from the 3' end (for HPV 45 targets) but the HPV 6, 11, 42 and 44 would have two mismatches at the 3' end itself resulting in very poor efficiency for extension or amplification.

Region E1-18-2(a) [Starting at Nucleotide 1019] (SEQ ID NOS 468-473, respectively in order of appearance)

```
18 GAGGA  CGAAA  ATGCA  ACAGA  CACAG  G  mismatches

39 -----  T----  -----  -----  T----  -      2

45 -----  T----  C----  -----  T----  -      3

59 -----  -----  -----  -----  T----  -      1

68 -----  T----  -C---  -----  T----  -      3

70 -----  -----  ----G  -----  T----  -      2
```

Potential Consensus E1-18-2(b) (SEQ ID NOS 474-484, respectively in order of appearance)

```
   GAGGA  TGAAA  ATGCA  ACAGA  TACAG  G  mismatches

18 -----  C----  -----  -----  C----  -      2

39 -----  -----  -----  -----  -----  -      0

45 -----  -----  C----  -----  -----  -      1

59 -----  C----  -----  -----  -----  -      1

68 -----  -----  -C---  -----  -----  -      1

70 -----  C----  ----G  -----  -----  -      2

6 -----  C--GG  -G-TG  GAG--  C-GT-  -     12

11 -----  A--GG  -G-TG  GAG--  C-GT-  -     12

42 -----  C----  ---T-  GAC--  --GT-  -      7

44 -----  C--GG  CA-TG  GAG--  --GT-  -     12
```

For consensus sequence E1-18-2(b), the lowest match with HPV 18, HPV 45, HPV 39, HPV 59, HPV 68 and HPV 70 is 24 out of 26 bases; the highest match for HPV 6, HPV 11, HPV 42, HPV 43 and HPV 44 is 19 out of 26.

Region E1-18-3(a) [Starting at Nucleotide 1090] (SEQ ID NOS 485-490, respectively in order of appearance)

```
18 ACAGG  CAGAG  CTAGA  GACAG  CACAG  G  mismatches

45 -----  -----  -A---  -----  -----  -      1

39 -----  -----  -GT--  -----  -----  -      2

68 -----  -----  -GT--  -----  -----  -      2

70 -----  -----  -GC--  -----  -----  -      2

59 -----  -----  -GC--  -----  -----  -      2
```

Potential Consensus E1-18-3(b) (SEQ ID NOS 491-501, respectively in order of appearance)

```
   ACAGG  CAGAG  CGAGA  GACAG  CACAG  G  mismatches

18 -----  -----  -T---  -----  -----  -      1

45 -----  -----  -A---  -----  -----  -      1

39 -----  -----  --T--  -----  -----  -      1

68 -----  -----  --T--  -----  -----  -      1

70 -----  -----  --C--  -----  -----  -      1

59 -----  -----  --C--  -----  -----  -      1

6 ---CA  ATTCA  -T---  A***-  -----  -     12

11 ---AA  ATTCT  GT---  A***-  -----  -     13

42 ---TA  --A--  -A--T  A***-  -----  -      9

44 ---CA  ATTCC  AT---  A***-  -----  -     13
```

For consensus sequence E1-18-1(b), the lowest match with HPV 18, HPV 45, HPV 39, HPV 59, HPV 68 and HPV 70 is 25 out of the 26 bases; the highest match for HPV 6, HPV 11, HPV 42, HPV 43 and HPV 44 is 17 out of 26.

Region E1-18-4(a) [Starting at Nucleotide 1129] (SEQ ID NOS 502-507, respectively in order of appearance)

```
18 GCAGG  AGGTC  CACAA  TGATG  CAC  mismatches

45 -----  -A--T  --G--  -----  ---       3

39 ---A-  ---C-  --A-G  G----  ---       5

68 ---AC  ---C-  --A-G  G----  ---       6

70 ---A-  ---C-  --A-G  G----  ---       5

59 -----  -A-C-  --A-G  G----  ---       5
```

Potential Consensus E1-18-4(b) (SEQ ID NOS 508-518, respectively in order of appearance)

```
   GCAGG  AAGTC  CAGAA  TGATG  CAC  mismatches

18 -----  -G---  --C--  -----  ---       2

45 -----  ----T  -----  -----  ---       1
```

-continued

| | GCAGG | AAGTC | CAGAA | TGATG | CAC | mismatches |
|---|---|---|---|---|---|---|
| 39 | ---A- | -G-C- | --A-G | G---- | --- | 6 |
| 68 | ---AC | -G-C- | --A-G | G---- | --- | 7 |
| 70 | ---A- | -G-C- | --A-G | G---- | --- | 6 |
| 59 | ----- | ---C- | --A-G | G---- | --- | 4 |
| 6 | ----- | -G-CG | G-C-C | CC--T | ATG | 12 |
| 11 | ----- | -G-CG | G-TGC | -C--T | ATG | 12 |
| 42 | A--AC | ---CA | --TGC | A---C | AGG | 13 |
| 44 | ----- | -G-CG | G-TGC | -C--T | ATG | 12 |

Potential Consensus E-1-18-4(c) (SEQ ID NOS 519-529, respectively in order of appearance)

| | GCAAG | AGGCC | CAAAG | GGATG | CAC | mismatches |
|---|---|---|---|---|---|---|
| 18 | ---G- | ---T- | --C-A | T---- | --- | 5 |
| 45 | ---G- | -A-TT | --G-A | T---- | --- | 7 |
| 39 | ----- | ----- | ----- | ----- | --- | 0 |
| 68 | ----C | ----- | ----- | ----- | --- | 1 |
| 70 | ----- | ----- | ----- | ----- | --- | 0 |
| 59 | ---G- | -A--- | ----- | ----- | --- | 2 |
| 6 | ---G- | ----G | G-C-C | CC--T | ATG | 11 |
| 11 | ---G- | ----G | G-TGC | TC--T | ATG | 12 |
| 42 | A---C | -A--A | --TGC | A---C | AGG | 12 |
| 44 | ---G- | ----G | G-TGC | TC--T | ATG | 12 |

For consequence E1-18-4(b), the lowest match with HPV 18 and HPV 45 is 21 out of the 23 bases; the highest match for HPV 6, HPV 11, HPV 42, HPV 43 and HPV 44 is 11 out of 23. For consensus sequence E1-18-4(c), the lowest match with HPV 39, HPV 59, HPV 68 and HPV 70 is 21 out of the 23 bases; the highest match for HPV 6, HPV 11, HPV 42, HPV 43 and HPV 44 is 12 out of 23.

C) HPV 51 Cluster

Using the Region E1-18-1(a) from above (SEQ ID NOS 530-534, respectively in order of appearance)

| | GAAGG | TACAG | ACGGG | GAGGG | mismatches |
|---|---|---|---|---|---|
| 18 | | | | | |
| 51 | ----- | ----- | -G-AT | ----- | 3 |
| 56 | ----- | ----- | -T--- | ----- | 1 |
| 66 | ----- | ----- | -T--- | ----- | 1 |
| 53 | ----- | ----- | -T-AT | ----- | 3 |

Potential Consensus E1-51-1(a) [Starting at Nucleotide 883] (SEQ ID NOS 535-543, respectively in order of appearance)

| | GAAGG | TACAG | ATGGT | GAGGG | G | mismatches |
|---|---|---|---|---|---|---|
| 51 | ----- | ----- | -G-A- | ----- | - | 2 |
| 56 | ----- | ----- | ----G | ----- | - | 1 |
| 66 | ----- | ----- | ----G | ----- | - | 1 |
| 53 | ----- | ----- | ---A- | ----- | - | 1 |
| 6 | TC--- | ----- | -AAA- | ----- | - | 5 |
| 11 | TC--- | ----- | -AAA- | ----- | - | 5 |
| 42 | AC--- | ----- | -G*** | ----- | - | 6 |
| 44 | AC--- | ----- | -G--A | AC--- | - | 6 |

For consensus sequence E1-51-1(a), the lowest match with HPV 51, HPV 56 and HPV 66 is 19 out of 21 bases; the highest match for HPV 6, HPV 11, HPV 42, HPV 43 and HPV 44 is 16 out of 21. This consensus sequence also matches well with HPV 53 (20 out of 21).

Region E1-51-2(a) [Starting at Nucleotide 931] (SEQ ID NOS 544-547, respectively in order of appearance)

| | GAAGC | AATAG | TAGAA | AAAAA | AACAG | GA | mismatches |
|---|---|---|---|---|---|---|---|
| 51 | ----- | ----- | ----- | ----- | ----- | -- | |
| 56 | --G-- | ---T- | ----- | ----- | ----- | -- | 2 |
| 66 | ----- | ---T- | ----- | -G--- | ---G- | -G | 4 |
| 53 | --G-- | ----- | --A-- | ---CG | T---- | -G | 6 |

Potential Consensus E1-51-2(b) (SEQ ID NOS 548-556, respectively in order of appearance)

| | GAAGC | AATTG | TAGAA | AAAAA | AACAG | GA | mismatches |
|---|---|---|---|---|---|---|---|
| 51 | ----- | ---A- | ----- | ----- | ----- | -- | 1 |
| 56 | --G-- | ----- | ----- | ----- | ----- | -- | 1 |
| 66 | ----- | ----- | ----- | -G--- | ---G- | -G | 3 |
| 53 | --G-- | ---A- | --A-- | ---CG | T---- | -G | 7 |
| 6 | ----- | T--A- | -GC-- | C-CCC | ----- | -T | 9 |
| 11 | ----- | C--A- | ----G | C-C-C | T---- | -T | 8 |
| 42 | ----- | T--A- | ----C | ----C | ----- | A- | 5 |
| 44 | --G-- | T--A- | -G--G | --C-C | ---C- | -G | 9 |

For consensus sequence E1-51-2(b) the lowest match with HPV 51, HPV 56 and HPV 66 is 24 out of 27 bases; the highest match for HPV 6, HPV 11, HPV 42, HPV 43 and HPV 44 is 22 out of 27. If E1-51-2(b) was used as a rightwards primer, HPV 51 and HPV 56 would be extended or amplified but HPV 66 and HPV 53 would not be.

Region E1-51-3(a) Immediately Adjacent to E1-51-2 [Starting at Nucleotide 958] (SEQ ID NOS 557-560, respectively in order of appearance)

|    | GATAA | TGTTT | CGGAT | GATGA | mismatches |
|----|-------|-------|-------|-------|------------|
| 56 | ----- | AA-A- | -A--- | ----- | 4 |
| 66 | ----C | AA-A- | -A--- | ----- | 5 |
| 53 | ---GT | AA-A- | -T--A | ----- | 6 |

Potential Consensus 51 E1-51-3(b) (SEQ ID NOS 561-569, respectively in order of appearance)

|    | GATAA | AGTTT | CAGAT | GATGA | mismatches |
|----|-------|-------|-------|-------|------------|
| 51 | ----- | T---- | -G--- | ----- | 2 |
| 56 | ----- | -A-A- | ----- | ----- | 2 |
| 66 | ----C | -A-A- | ----- | ----- | 3 |
| 53 | ---GT | -A-A- | -T--A | ----- | 6 |
| 6  | ACAC- | -A-A- | ----C | ----- | 7 |
| 11 | ACAC- | -A-A- | ----A | ----- | 7 |
| 42 | A--GC | TA--- | ----- | ----- | 5 |
| 44 | CAAC- | -A-A- | ----G | ----- | 7 |

For consensus sequence E1-51-2(b) the lowest match with HPV 51, HPV 56 and HPV 66 is 17 out of 20 bases; the highest match for HPV 6, HPV 11, HPV 42, HPV 43 and HPV 44 is 15 out of 20.

Region E1-51-4(a) [Starting at Nucleotide 1609] (SEQ ID NOS 570-578, respectively in order of appearance)

|    | TTATA ATGTA | TGCAC CTACC | ATATA ATATA | CAATG CAATG | TTTAA TTTAA | CATGT CATGT | mismatches |
|----|-------|-------|-------|-------|-------|-------|------------|
| 56 | ----- | T--T- | ----G | ----- | ----A | ----- | 4 |
| 66 | G---- | ---T- | ----G | ----- | ----A | ----- | 4 |
| 53 | --A-- | T---- | ----G | ----- | ----A | ----- | 4 |
| 6  | T-A-- | TGC-- | ----- | ----- | GC--A | --AA- | 10 |
| 11 | T-A-- | TGC-- | ----- | ----- | GC-TA | --AA- | 11 |
| 42 | T-A-- | TAC-- | ----- | ----- | GC--A | -C--- | 9 |
| 44 | CCA-- | TAG-- | -C--- | ----- | GC-TA | --AA- | 14 |

Potential Consensus E1-51-4(b) (SEQ ID NOS 579-587, respectively in order of appearance)

|    | ATGTA | CTATC | ATATG | CAATG | TTTAT | CATGT | mismatches |
|----|-------|-------|-------|-------|-------|-------|------------|
| 51 | ----- | ---C- | ----A | ----- | ----- | ----- | 2 |
| 56 | ----- | T---- | ----- | ----- | ----A | ----- | 4 |
| 66 | G---- | ----- | ----- | ----- | ----A | ----- | 4 |
| 53 | --A-- | T--C- | ----- | ----- | ----A | ----- | 4 |
| 6  | T-A-- | TGCC- | ----A | ----- | GC--A | --AA- | 10 |
| 11 | T-A-- | TGCC- | ----A | ----- | GC-TA | --AA- | 11 |
| 42 | T-A-- | TACC- | ----A | ----- | GC--A | -C--- | 9 |
| 44 | CCA-- | TAGC- | -C--A | ----- | GC-TA | --AA- | 14 |

Example 7

Amplification using E7 Oncogenic Specific Sequences from Example 3 as Forward Primers, GP124 (Evander and Wadell, 1991 J. Vir Methods 31; 239-250) of E1 as a Reverse Primer Set and E1 Oncogenic Specific Sequences from Example 7 as Probes A) Comparison of GP124 Sequences with Target and Non-Target Sequences (SEQ ID NOS 588-608, respectively in order of appearance)

|    | TATGGC | (A/T) | (A/G) | T | (A/T) | CTGAA | GTGGAA | mismatches |
|----|--------|-------|-------|---|-------|-------|--------|------------|
| 16 | ----- | A | A | - | A | ----- | ----- | 0 |
| 35 | ----- | A | T | - | A | ----- | ----- | 0 |
| 31 | ----- | A | A | - | A | ----- | ----- | 0 |
| 52 | ----- | A | A | - | A | G---- | ----- | 1 |
| 33 | ----- | A | A | - | A | ----- | ----- | 0 |
| 58 | ----- | A | A | - | A | ----- | ----- | 0 |
| 18 | ----- | T | G | - | T | ----- | ----- | 0 |
| 45 | ----- | T | G | - | T | ----- | ----- | 0 |
| 39 | ----- | A | A | - | A | TG--- | ----- | 2 |

-continued

| | TATGGC | (A/T) | (A/G) | T | (A/T) | CTGAA | GTGGAA | mismatches |
|---|---|---|---|---|---|---|---|---|
| 68 | ----TCA | N | A | - | A | TG--- | ----- | 5 |
| 70 | ----- | A | A | - | A | TG--- | ----- | 2 |
| 59 | ----- | T | A | - | T | ----- | ----- | 0 |
| 51 | ----- | A | A | - | A | -AC-- | ----- | 2 |
| 56 | ----- | A | A | - | A | -***- | T---- | 7 |
| 66 | ----- | A | A | - | A | -***- | T---- | 7 |
| 53 | ----- | A | A | - | A | -***T | T---- | 8 |
| 6 | ----- | T | A | - | T | ----- | ----- | 0 |
| 11 | ----- | T | A | - | T | ----- | ----- | 0 |
| 42 | ----- | T | A | - | T | ----- | ----- | 0 |
| 44 | ----- | A | A | - | A | ----- | ----- | 0 |

Some of the HPV types listed above are not likely to be amplified efficiently by the GP124 set (HPV 68, 56, 66 and 53). Also, the Tm of these primers could be as low as 58° C. even with a perfect match. As such, the substation of 2-Amino-dA for the normal A's at three of the non-permutational sites could increase the Tm by 9° C.

B) Selection of Consensus Sequences from Examples 3 and 6

| | targets | crossreactions |
|---|---|---|
| Forward Primer | | |
| E7-16-1(b) | 16, 31, 33, 35, 52, 58 | |
| E7-18-2(b) | 18, 45, 59 | |
| E7-18-2(c) | 39, 68 | 70 |
| E7-51-1(b) | 51, 56 | 66 |
| Probe | | |
| E6-16-2(b) | 16, 31, 35 | |
| E6-16-2(c) | 33, 52 and 58 | |
| E6-18-3(b) | 18, 39, 45, 59, 68 | |
| E6-51-2(b) | 51, 56 | possibly 66 |
| Reverse Primer | | |
| GP124 | 16, 31, 33, 35, 52, 58, 18, 39, 45, 59, 51 | 6, 11, 42, 44, 70 |

C) Selection of Primer and Probe Sequences from Examples 3 and 6

(1) Forward Primer Sequences

```
Primer FP-31                CAACT GACCT CTACT GCTAT
                            GAGCA (SEQ ID NO:609)
Source                      E7-16-1(b)
targets                     16, 31, 33, 33, 35, 52 and
                            58
minimal target match        23 out of 25
maximal non-target match    19 out of 25
Theoretical Tm              74° C.

Primer FP-32                AAGAA AACGA TGAAA CAGAT
                            GGAGT TA (SEQ ID NO: 610)
Source                      E7-18-2(b)
```
-continued
```
targets                     18, 45 and 59
minimal target match        24 out of 27
maximal non-target match    21 out of 27
Theoretical Tm              72° C.

Primer FP-33                ATGAA ACAGA TGAAC CCGAC
                            CATG (SEQ ID NO: 611)
Source                      E7-18-2(c)
targets                     39 and 68
minimal target match        23 out of 24
maximal non-target match    14 out of 24
Theoretical Tm              70° C.

Primer FP-34                GAAAT TGACT TACAA TGCAA
                            CGAGC AAT (SEQ ID NO: 612)
Source                      E7-51-1(b)
targets                     51 and 56
minimal target match        25 out of 28
maximal non-target match    18 out of 28
Theoretical Tm              76° C.
```

(2) Probe Sequences

```
Primer PRO-31               GAGAC AGCAT ATGCA TTGTT
                            TAATG C (SEQ ID NO: 613)
Source                      E1-16-2(b)
targets                     16, 31 and 35
minimal target match        24 out of 26
maximal non-target match    19 out of 26
Theoretical Tm              72° C.

Primer PRO-32               GAGGC AGCCT GGGCA TTGTT
                            TAAT (SEQ ID NO: 614)
Source                      E1-16-2(c)
targets                     33, 52 and 58
minimal target match        22 out of 24
maximal non-target match    19 out of 24
Theoretical Tm              72° C.

Primer PRO-33               AGGCA GAGCG AGAGA CAGCA CA
                            (SEQ ID NO: 615)
Source                      E1-18-3(b)
targets                     18, 39, 45, 59 and 68
minimal target match        21 out of 22
maximal non-target match    13 out of 22
Theoretical Tm              72° C.
```

```
Primer PRO-34              GAAGC AATTG TAGAA AAAAA
                           AACAG GA (SEQ ID NO: 616)
Source                     E1-51-2(b)
targets                    51 and 56
minimal target match       26 out of 27
maximal non-target match   22 out of 27
Theoretical Tm             70° C.
```

Example 8

Amplification Using E7 Oncogenic Specific Sequences from Example 3 as Forward Primers and E1 Oncogenic Specific Sequences from Example 6 as Probes and Reverse Primers A) Selection of Consensus Sequences from Examples 3 and 6

|  | targets | crossreactions |
|---|---|---|
| Forward Primers |  |  |
| E7-16-1(b) | 16, 31, 33, 35, 52, 58 |  |
| E7-18-2(b) | 18, 45, 59 |  |
| E7-18-2(c) | 39, 68 | 70 |
| E7-51-1(b) | 51, 56 | 66 |
| Probes |  |  |
| E1-16-1(a) | 16, 31, 33, 35, |  |
| E1-16-1(b) | 33, 52, 58 |  |
| E1-18-2(b) | 18, 39, 45, 59, 68 | 70 |
| E1-51-1(b) | 51, 56 | 53, 66 |
| Reverse Primers |  |  |
| E1-16-2(b) | 16, 31, 35 |  |
| E1-16-2(c) | 33, 52, 58 |  |
| E1-18-3(b) | 18, 39, 45, 59, 68 | 70 |
| E1-51-2(b) | 51, 56 | possibly 66 |

B) Selection of Primer Sequences from Examples 3 and 6

(1) Forward Primer Sequences are as Described in Example 7 (i.e. Primers FP-31, FP-32, FP-33 and FP-34)

(2) Probe Sequences

```
Primer Pro-41              ATGGC TGATC CTGCA GGTAC
                           (SEQ ID NO: 617)
Source                     E1-16-1(a)
targets                    16, 31, 33 and 35
minimal target match       18 out of 20
maximal non-target match   16 out of 20
Theoretical Tm             60° C.

Probe Pro-42               ATGGA CGACC CTGAA GGTAC
                           (SEQ ID NO: 618)
Source                     E1-16-1(b)
targets                    33, 52 and 58
minimal target match       18 out of 20
maximal non-target match   14 out of 20
Theoretical Tm             62° C.
```

```
Probe Pro-43               GAGGA TGAAA ATGCA ACAGA
                           TACAG G (SEQ ID NO: 619)
Source                     E1-18-2(b)
targets                    18, 39, 45, 59 and 68
minimal target match       24 out of 26
maximal non-target match   20 out of 26
Theoretical Tm             72° C.

Probe Pro-44               GAAGG TACAG ATGGT GAGGG G
                           (SEQ ID NO: 620)
Source                     E1-51-1(b)
targets                    51 and 56
minimal target match       26 out of
maximal non-target match   19 out of
Theoretical Tm             66°
```

For PRO-43, substitution of 2-amino-dA for normal A's in two positions can raise the theoretical Tm by 6° C., converting their theoretical Tm to 72° C.

(2) Reverse Primer Sequences

```
Primer RP-41               GCATT AAACA ATGCA TATGC
                           TGTCT C (SEQ ID NO: 621)
Source                     E1-16-2(b)
targets                    16, 31, and 35
minimal target match       24 out of 26
maximal non-target match   19 out of 26
Theoretical Tm             72° C.

Primer RP-42               ATTAA ACAAT GCCCA GGCTG
                           CCTC (SEQ ID NO: 622)
Source                     E1-16-2(c)
targets                    33, 52 and 58
minimal target match       22 out of 24
maximal non-target match   19 out of 24
Theoretical Tm             72° C.

Primer RP-43               TGTGC TGTCT CTCGC TCTGC CT
                           (SEQ ID NO: 623)
Source                     E1-18-3(b)
targets                    18, 39, 45, 59 and 68
minimal target match       21 out of 22
maximal non-target match   13 out of 22
Theoretical Tm             70° C.

Primer RP-44               TGCTG TTTTT TTTTC TACAA
                           TTG (SEQ ID NO: 624)
Source                     E1-51-2(c)
targets                    51 and 56
minimal target match       22 out of 23
maximal non-target match   18 out of 23
Theoretical Tm             58° C.
```

For PRO-41 and PRO-42, substitution of 2-amino-dA for normal A's in three positions can raise the theoretical Tm's by 9° C., converting their theoretical Tm's to 69° C. and 71° C. respectively.

For RP-44, substitution of 2-amino-dA for normal A's in two positions and 3-methyl-dC in two positions can raise the theoretical Tm by 8.6° C., converting the theoretical Tm to 67° C.

Example 9

Selection of Conserved Differential Sequences from the L2 Gene

A) HPV 16 Cluster

Region L2-16-6(a) [Starting at Nucleotide 5619] (SEQ ID NOS 625-634, respectively in order of appearance)

| 16 | TACCA | TATTT | TTTTT | CAGAT | GTCTC | T | mismatches |
|---|---|---|---|---|---|---|---|
| 35 | -C--- | ----- | ----G | ----- | ----- | - | 0 |
| 31 | --T-- | ----- | ----A | ----- | ----- | - | 2 |
| 52 | -T--- | ----- | ----A | ----- | ---CG | - | 4 |
| 33 | -T--- | ----- | ----A | ----- | ---CG | - | 4 |
| 58 | -T--- | ----- | ----G | ----- | ---CG | - | 4 |
| 6  | -T--C | -TA-- | ----- | ----- | --GG- | G | 7 |
| 11 | -T--C | -TA-- | ----A | ----- | --GG- | G | 8 |
| 42 | -A--- | ----- | ----G | ----- | ---CG | - | 4 |
| 44 | -T-TC | -TG-- | ----G | ----- | --GG- | G | 9 |

Potential Consensus L2-16-6(b) (SEQ ID NOS 635-645, respectively in order of appearance)

|    | TTCCA | TATTT | TTTTA | CAGAT | GTCCG | T | mismatches |
|---|---|---|---|---|---|---|---|
| 16 | -A--- | ----- | ----T | ----- | ---TC | - | 4 |
| 35 | -C--- | ----- | ----G | ----- | ---TC | - | 4 |
| 31 | -AT-- | ----- | ----- | ----- | ---TC | - | 4 |
| 52 | ----- | ----- | ----- | ----- | ----- | - | 0 |
| 33 | ----- | ----- | ----- | ----- | ----- | - | 0 |
| 58 | ----- | ----- | ----G | ----- | ----- | - | 1 |
| 6  | -T--C | -TA-- | ----T | ----- | --GGC | G | 9 |
| 11 | -T--C | -TA-- | ----- | ----- | --GGC | G | 8 |
| 42 | -A--- | ----- | ----G | ----- | ----- | - | 2 |
| 44 | -T-TC | -TG-- | ----G | ----- | --GGC | G | 10 |

B) HPV 18 Cluster

Region L2-18-6(a) [Starting at Nucleotide 5595] (SEQ ID NOS 646-654, respectively in order of appearance)

| 18 | TTCCC | TATTT | TTTTG | CAGAT | GGC | mismatches |
|---|---|---|---|---|---|---|
| 45 | ----- | ----- | ----- | ----- | --- | 0 |
| 39 | ----- | ----- | ----T | ----- | --- | 1 |
| 68 | ----T | ----- | ----- | ----- | --- | 1 |
| 70 | ----- | ----- | ----A | ----- | --- | 1 |
| 59 | ----- | ----- | ----A | ----- | --- | 1 |
| 51 | -A--- | ----- | ----A | ----- | --- | 2 |
| 56 | ----- | ----- | ----- | ----- | --- | 0 |
| 53 | ----- | ----- | -C--- | ----- | --- | 1 |

Potential Consensus L2-18-6(b) (SEQ ID NOS 655-668, respectively in order of appearance)

|    | TTCCC | TATTT | TTTTA | CAGAT | GGC | mismatches |
|---|---|---|---|---|---|---|
| 18 | ----- | ----- | ----G | ----- | --- | 1 |
| 45 | ----- | ----- | ----G | ----- | --- | 1 |
| 39 | ----- | ----- | ----T | ----- | --- | 1 |
| 68 | ----T | ----- | ----- | ----- | --- | 0 |
| 70 | ----- | ----- | ----- | ----- | --- | 0 |
| 59 | ----- | ----- | ----- | ----- | --- | 0 |
| 51 | -A--- | ----- | ----- | ----- | --- | 1 |
| 56 | ----- | ----- | ----G | ----- | --- | 1 |
| 53 | ----- | ----- | -C--G | ----- | --- | 2 |
| 6  | ----- | -TA-- | ----T | ----- | -TG | 5 |
| 11 | ----- | -TA-- | ----- | ----- | -TG | 4 |
| 42 | -A--A | ----- | ----G | ----- | -T- | 4 |
| 44 | --T-- | -TG-- | ----G | ----- | -TG | 6 |

The region L2-18-6(a) is sufficiently conserved that it can be used for HPV 51 and 56 as well.

Example 10

Selection of Conserved Differential Sequences from the L1 Gene

A) HPV 16 Cluster

Region L1-16-1(a) [Starting at Nucleotide 5658] (SEQ ID NOS 669-678, respectively in order of appearance)

```
16  GAGGC  CACTG  TCTAC  TTGCC  TCCTG  TCCCA  GT   mismatches

35  --A--  -----  -----  C----  ---A-  -GT--  --   5

31  -----  T----  -----  --A--  A----  -----  --   3

52  -----  -----  -G---  C----  -----  -A--T  --   4

33  -----  ---A-  -G---  C----  -----  ----T  --   4

58  -----  -----  -G---  C----  -----  ----T  --   3

6  --CAG  ---A-  -A--T  G----  ----C  CTAAC  CC   15

11  --CAG  ---A-  -A--T  G----  ----C  C-AAC  CC   14

42  --CAA  --AG-  -T--T  C----  ----C  CT---  GT   13

44  --AAA  --AG-  -A--T  G----  ----C  C-G-C  CC   14
```

Potential Consensus L1-16-1(b) (SEQ ID NOS 679-689, respectively in order of appearance)

```
    GAGGC  CACTG  TCTAC  TTGCC  TCCTG  TGCCA  GT   mismatches

16  -----  -----  -----  -----  -----  -C---  --   1

35  --A--  -----  -----  C----  ---A-  --T--  --   4

31  -----  T----  -----  --A--  A----  -C---  --   4

52  -----  -----  -G---  C----  -----  -A--T  --   4

33  -----  ---A-  -G---  C----  -----  -C--T  --   5

58  -----  -----  -G---  C----  -----  -C--T  --   4

6  --CAG  ---A-  -A--T  G----  ----C  CTAAC  CC   15

11  --CAG  ---A-  -A--T  G----  ----C  CCAAC  CC   15

42  --CAA  --AG-  -T--T  C----  ----C  CT---  GT   13

44  --AAA  --AG-  -A--T  G----  ----C  CCG-C  CC   15
```

Potential Consensus L1-16-1(c) (SEQ ID NOS 690-700, respectively in order of appearance)

```
    GAGGC  CACTG  TGTAC  CTGCC  TCCTG  TCCCT  GT   mismatches

16  -----  -----  -C---  T----  -----  ----A  00   3

35  --A--  -----  -C---  -----  ---A-  -GT-A  --   6

31  -----  T----  -C---  T-A--  A----  ----A  --   3

52  -----  -----  -----  -----  -----  -A---  --   4

33  -----  ---A-  -----  -----  -----  -----  --   4

58  -----  -----  -----  -----  -----  -----  --   3
```

| | GAGGC | CACTG | TGTAC | CTGCC | TCCTG | TCCCT | GT | mismatches |
|---|---|---|---|---|---|---|---|---|
| 6 | --CAG | ---A- | -A--T | G---- | ----C | CTAAC | CC | 15 |
| 11 | --CAG | ---A- | -A--T | G---- | ----C | C-AAC | CC | 14 |
| 42 | --CAA | --AG- | -T--T | ----- | ----C | CT--A | GT | 13 |
| 44 | --AAA | --AG- | -A--T | G---- | ----C | C-G-C | CC | 14 |

B) HPV 18 Cluster
Region L1-18-1(a) [Starting at Nucleotide 5644] (SEQ ID NOS 701-710, respectively in order of appearance)

| 18 | TATAT | CTTCC | ACCTC | CTTCT | GTGGC | AAGAG | TTGT | mismatches |
|---|---|---|---|---|---|---|---|---|
| 45 | ----- | ----- | ---A- | ----- | ----- | C---- | ---- | 2 |
| 39 | ----- | T-G-- | T--A- | ----- | ----- | G-AG- | ---- | 7 |
| 68 | -G--- | T-G-- | T--C- | -C--A | ----- | G-AG- | ---- | 10 |
| 70 | -G--- | T-G-- | ---C- | ----- | ----- | G-AG- | ---- | 7 |
| 59 | -G--- | --A-- | T-AA-A | ----- | --A-- | T-AG- | ---- | 8 |
| 6 | ----- | G-G-- | T---- | -TAAC | CCT--AT- | C-A-- | ---- | 14 |
| 11 | ----- | G-G-- | T---- | -CAAC | CCT--AT- | C-AG- | ---- | 15 |
| 42 | -T--- | --A-- | T---- | -TC-- | --TT- | C-AG- | -G-- | 11 |
| 44 | ----- | G-G-- | T---- | -CG-C | CCA--AT- | C-A-- | -AA- | 15 |

As seen above, HPV 6, 11 and 44 have a three base insertion in the homologous sequence; each of the inserted nucleotides is counted as a mismatch.

Potential Consensus L1-18-1(b) (SEQ ID NOS 711-721, respectively in order of appearance)

| | TATAT | CTTCC | ACCAC | CTTCT | GTGGC | AAGAG | TTGT | mismatches |
|---|---|---|---|---|---|---|---|---|
| 18 | ----- | ----- | ---T- | ----- | ----- | ----- | ---- | 1 |
| 45 | ----- | ----- | ----- | ----- | ----- | C---- | ---- | 1 |
| 39 | ----- | T-G-- | T---- | ----- | ----- | G-AG- | ---- | 6 |
| 68 | -G--- | T-G-- | T--C- | -C--A | ----- | G-AG- | ---- | 10 |
| 70 | -G--- | T-G-- | ---C- | ----- | ----- | G-AG- | ---- | 7 |
| 59 | -G--- | --A-- | T---- | ----- | --A-- | T-AG- | ---- | 7 |
| 6 | ----- | G-G-- | T--T- | -TAAC | CCT--AT- | C-A-- | ---- | 15 |
| 11 | ----- | G-G-- | T--T- | -CAAC | CCT--AT- | C-AG- | ---- | 16 |
| 42 | -T--- | --A-- | T--T- | -TC-- | --TT- | C-AG- | -G-- | 12 |
| 44 | ----- | G-G-- | T--T- | -CG-C | CCA--AT- | C-A-- | -AA- | 16 |

Potential Consensus L1-18-1(c) (SEQ ID NOS 722-732, respectively in order of appearance)

|    | TATAT | TTGCC | TCCAC | CTTCT | GTGGC | TAAGG | TTGT | mismatches |
|----|-------|-------|-------|-------|-------|-------|------|------------|
| 18 | ----- | C-T-- | A--T- | ----- | ----- | A-GA- | ---- | 1 |
| 45 | ----- | C-T-- | A---- | ----- | ----- | C-GA- | ---- | 1 |
| 39 | ----- | ----- | ----- | ----- | ----- | G---- | ---- | 1 |
| 68 | -G--- | ----- | ---C- | -C--A | ----- | G---- | ---- | 5 |
| 70 | -G--- | ----- | A--C- | ----- | ----- | G---- | ---- | 4 |
| 59 | -G--- | C-A-- | ----- | ----- | --A-- | ----- | ---- | 4 |
| 6  | ----- | G---- | ---T- | -TAAC | CCT--AT- | C---- | ---- | 14 |
| 11 | ----- | G---- | ---T- | -CAAC | CCT--AT- | C---- | ---- | 15 |
| 42 | -T--- | C-A-- | ---T- | -TC-- | --TT- | C---- | -G-- | 11 |
| 44 | ----- | G---- | ---T- | -CG-C | CCA--AT- | C--A- | -AA- | 15 |

Region L1-18-2(a) [Starting at Nucleotide 5790] (SEQ ID NOS 733-742, respectively in order of appearance)

|    |       | CAGGA | TATTC | CTAAG | GTTTC | TGCAT | mismatches |
|----|-------|-------|-------|-------|-------|-------|------------|
| 18 |       | CAGGA | TATTC | CTAAG | GTTTC | TGCAT |            |
| 45 |       | ----C | -G--- | ----- | --A-- | C---- | 4 |
| 39 |       | ----- | C---- | -A--- | --G-- | ----- | 3 |
| 68 |       | ----- | C---- | ----- | --G-- | ----- | 2 |
| 70 |       | ----- | A---- | ----- | --G-- | ----- | 2 |
| 59 |       | ----- | -G--- | ----- | --G-- | ----- | 2 |
| 6  |       | ACT-T | -G-G- | -A--- | --G-- | A-G-- | 10 |
| 11 |       | ACA-T | -G-A- | -A--- | --G-- | --G-- | 9 |
| 42 |       | ACAT- | ---C- | -C--A | --G-- | --GT- | 10 |
| 44 |       | ACACT | -G-G- | ----- | ----- | G-G-- | 9 |

Potential Consensus L1-18-2(b) (SEQ ID NOS 743-753, respectively in order of appearance)

|    | CAGGA | TATTC | CTAAG | GTATC | TGCAT | mismatches |
|----|-------|-------|-------|-------|-------|------------|
| 18 | ----- | ----- | ----- | --T-- | ----- | 1 |
| 45 | ----C | -G--- | ----- | ----- | C---- | 3 |
| 39 | ----- | C---- | -A--- | --G-- | ----- | 3 |
| 68 | ----- | C---- | ----- | --G-- | ----- | 2 |
| 70 | ----- | A---- | ----- | --G-- | ----- | 2 |
| 59 | ----- | -G--- | ----- | --G-- | ----- | 2 |
| 6  | ACT-T | -G-G- | -A--- | --G-- | A-G-- | 10 |
| 11 | ACA-T | -G-A- | -A--- | --G-- | --G-- | 9 |
| 42 | ACAT- | ---C- | -C--A | --G-- | --GT- | 10 |
| 44 | ACACT | -G-G- | ----- | --T-- | G-G-- | 10 |

Region L1-18-3(a) [Starting at Nucleotide 6416] (SEQ ID NOS 754-759, respectively in order of appearance)

|    | CAGTT | ATGTA | TTTTG | GGCTG | TGCCC | CTGC | mismatches |
|----|-------|-------|-------|-------|-------|------|------------|
| 18 | CAGTT | ATGTA | TTTTG | GGCTG | TGCCC | CTGC |            |
| 45 | ---C- | G---- | ----A | --T-- | --TA- | ---- | 6 |
| 39 | ----- | G--C- | --A-A | ----- | --TT- | -C-- | 6 |
| 68 | --AC- | G---- | --A-A | ----- | --TT- | ---- | 7 |
| 70 | ----- | ----- | --A-A | ----- | --TA- | ---- | 4 |
| 59 | ---C- | G---- | --A-T | ----- | --TA- | ---- | 6 |

Potential Consensus L1-18-3(b) (SEQ ID NOS 760-770, respectively in order of appearance)

|    | CAGTT | GTGTA | TTTTA | GGCTG | TGCTC | C | mismatches |
|----|-------|-------|-------|-------|-------|---|------------|
| 18 | ----- | A---- | ----G | ----- | ---C- | - | 3 |
| 45 | ---C- | ----- | ----- | --T-- | --TA- | - | 4 |
| 39 | ----- | ---C- | --A-- | ----- | --T-- | - | 3 |
| 68 | --AC- | ----- | --A-- | ----- | --T-- | - | 4 |
| 70 | ----- | A---- | --A-- | ----- | --T-- | - | 3 |
| 59 | ---C- | ----- | --A-T | ----- | --TA- | - | 5 |
| 6  | --A-- | A--C- | -GG-T | --A-- | ---C- | - | 8 |
| 11 | ---C- | A---- | -GG-G | ----- | ----- | - | 5 |

|    | CAGTT | GTGTA | TTTTA | GGCTG | TGCTC | C | mismatches |
|----|-------|-------|-------|-------|-------|---|------------|
| 42 | ----- | ----T | -AG-T | ----- | -AAA- | - | 7 |
| 44 | --A-- | A---T | -GG-T | ----- | ---A- | - | 7 |

Potential Consensus L1-18-3(c) (SEQ ID NOS 771-781, respectively in order of appearance)

|    | CTGTG | TATTT | TAGGC | TGTGT | ACC | mismatches |
|----|-------|-------|-------|-------|-----|------------|
| 18 | T-A-- | ----- | -G--- | ----C | C-- | 5 |
| 45 | ----- | ----- | ----T | ----- | --- | 1 |
| 39 | T---- | C---A | ----- | ----- | T-- | 4 |
| 68 | ----- | ----A | ----- | ----- | T-- | 2 |
| 70 | T-A-- | ----A | ----- | ----- | T-- | 4 |
| 59 | ----- | ----A | -T--- | ----- | --- | 2 |
| 6  | T-A-- | C--GG | -T--A | ----C | C-- | 9 |
| 11 | --A-- | ---GG | -G--- | ----C | T-- | 6 |
| 42 | T---- | -T-AG | -T--- | ---AA | --- | 7 |
| 44 | T-A-- | -T-GG | -T--- | ----C | --- | 7 |

L1-18-3(b) has a maximum of 3 mismatches out of 26 for HPV 18, 39 and 70

L1-18-3(c) has a maximum of 2 mismatches out of 23 for HPV 45, 68 and 59

C) HPV 51 Cluster

Region L1-51-1(a) [Starting at Nucleotide 5548] (SEQ ID NOS 782-789, respectively in order of appearance)

|    | AAGGT | GTATT | TGCCA | CCTGC | ACCTG | T | mismatches |
|----|-------|-------|-------|-------|-------|---|------------|
| 51 | ----- | ----C | -A--T | --AA- | ----- | - | 5 |
| 66 | GCT-- | TGGCC | AT--T | TA-TA | CT--- | - | 17 |
| 53 | ----- | T---C | ----T | ---A- | C---- | - | 5 |
| 6  | -CA-- | A---G | ----T | ---C- | C---- | - | 7 |
| 11 | -CA-- | A---G | ----T | ---C- | C---- | - | 7 |
| 42 | ----- | T---C | -A--T | ---C- | T---- | - | 6 |
| 44 | C---- | A---G | ----T | ---C- | C---- | - | 6 |

Potential Consensus L1-51-1(b) (SEQ ID NOS 790-798, respectively in order of appearance)

|    | AAGGT | GTATT | TACCA | CCAGC | ACCTG | T | mismatches |
|----|-------|-------|-------|-------|-------|---|------------|
| 51 | ----- | ----- | -G--- | --T-- | ----- | - | 2 |
| 56 | ----- | ----C | ----T | ---A- | ----- | - | 3 |
| 66 | GCT-- | TGGCC | AT--T | TATTA | CT--- | - | 18 |
| 53 | ----- | T---C | -G--T | --TA- | C---- | - | 7 |
| 6  | -CA-- | A---G | -G--T | --TC- | C---- | - | 9 |
| 11 | -CA-- | A---G | -G--T | --TC- | C---- | - | 9 |
| 42 | ----- | T---C | ----T | --TC- | T---- | - | 6 |
| 44 | C---- | A---G | -G--T | --TC- | C---- | - | 8 |

Region L1-51-2(a) [Starting at Nucleotide 5701] (SEQ ID NOS 799-806, respectively in order of appearance)

|    | ATTCC | TAAAG | TATCT | GCATT | TCAAT | A | mismatches |
|----|-------|-------|-------|-------|-------|---|------------|
| 51 |       |       |       |       |       |   |            |
| 56 | ----- | C---- | -TAG- | ----A | ----- | - | 5 |
| 66 | GAA-G | -TTG- | ----C | --C-G | ----- | - | 10 |
| 53 | --C-- | ---G- | -G--- | ----- | ---G- | - | 4 |
| 6  | G-G-- | A--G- | -G--A | -G--A | ----- | - | 8 |
| 11 | G-A-- | A--G- | -G--- | -G--A | ----- | - | 7 |
| 42 | --C-- | C---- | -G--- | -GT-- | A--G- | - | 7 |
| 44 | G-G-- | ---G- | -T--G | -G--- | ----- | - | 6 |

Region L1-51-2(a) Partially Overlaps L1-18-2(a)

Potential Consensus L1-51-2(b) (SEQ ID NOS 807-815, respectively in order of appearance)

|    | ATTCC | CAAAG | TATGT | GCATT | TCAAT | A | mismatches |
|----|-------|-------|-------|-------|-------|---|------------|
| 51 | ----- | T---- | ---C- | ----- | ----- | - | 2 |
| 56 | ----- | ----- | -TA-- | ----A | ----- | - | 3 |
| 66 | GAA-G | TTTG- | ---CC | --C-G | ----- | - | 12 |
| 53 | --C-- | T--G- | -G-C- | ----- | ---G- | - | 6 |
| 6  | G-G-- | A--G- | -G-CA | -G--A | ----- | - | 9 |
| 11 | G-A-- | A--G- | -G-C- | -G--A | ----- | - | 8 |
| 42 | --C-- | ----- | -G-C- | -GT-- | A--G- | - | 7 |
| 44 | G-G-- | T--G- | -T-CG | -G--- | ----- | - | 8 |

Example 11

Transformation of Primer Binding Sequences in Amplicons

Consensus Region L2-18-6(a) from Example 9

```
TTCCC

```
<220> FEATURE:
<223> OTHER INFORMATION: Description of Artificial Sequence: Synthetic
      oligonucleotide

<400> SEQUENCE: 2
tctaaaataa gtgaatatag atggtat                                              27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcaaaagtaa gtgaatttag atggtat                                              27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tctaagataa gtgaatatag gcattat                                              27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tctaaaatta gtgaatatag acattat                                              27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tctaaaatag gtgagtatag acattat                                              27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggaaaaataa accaatatag acacttt                                              27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 8
gggaaaatta accaatatag acacttt                                             27

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tctaaaattt gtgcactgca cactac                                              26

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaaaaatta gtcaatatag gcacttt                                             27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggaaaaatta gtcaatatag gcacttt                                             27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tctaaaatta gtgaatatag acattat                                             27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tctaaaatta gtgagtatag acattat                                             27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tctaagatta gtgaatatag gcattat                                      27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tctaaaatta gtgaatatag acattat                                      27

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctaaaattg agtgagtata gacattat                                     28

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggaaaaatta accaatatag acacttt                                      27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gggaaaatta accaatatag acacttt                                      27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tctaaaattt gtgcactgcg acactac                                      27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
ggaaaaatta gtcaatatag gcacttt                                          27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtaaggtca atcaatttag gcatttt                                          27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tcaaaagtaa gtgaatatag atggtat                                          27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tcaaaaataa gtgaatatag atggtat                                          27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tcaaaagtaa gtgaatttag atggtat                                          27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggaaaaataa accaatatag acacttt                                          27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gggaaaatta accaatatag acacttt                                          27
```

```
<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tctaaaattt gtgcactgcg acactac                                           27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggaaaaataa gtcaatatag gcactttt                                          27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggtaaggtca atcaatttag gcagttt                                           27

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
attaggtgta ttaactgtca aaagccactg tgtcc                                  35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
attaggtgta ttacatgtca aaaccgctg tgtcc                                   35

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
attaggtgta ttaacgtgtc aaagaccgtt gtgtcc                                 36

<210> SEQ ID NO 33
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
attagatgta ttaatttgtc aaacgccatt atgtcc                                    36

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
attaggtgta ttatatgtca aagacctttg tgtcc                                     35

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
attagatgta ttatttgtca aagaccattg tgtcc                                     35

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
attcggtgct acctgtgtca cagaccgctg tgtga                                     35

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
attcgttgtt acctgtgtca caagccgttg tgtga                                     35

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
attcgctgtg ctatatgtca aaagccgtta tcaca                                     35

<210> SEQ ID NO 39
<211> LENGTH: 35
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 39
attagatgct gtaagtgtca caagccatta tcacc                              35

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atacgctgct atttgtgcca caaaccattg tgcca                              35

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
attaggtgta ttatctgtca aaaaccattg tgtcc                              35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
attaggtgta ttaactgtca aaagccactg tgtcc                              35

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
attaggtgta ttacatgtca aaaaccgctg tgtcc                              35

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
attaggtgta ttatcgtgtc aaagaccgct gtgtcc                             36

<210> SEQ ID NO 45
<211> LENGTH: 35
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 45
attagatgta aatttgtca aacgccatta tgtcc                                35

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
attaggtgta aatatgtca aagacctttg tgtcc                                35

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
attagatgta aatttgtca aagaccattg tgtcc                                35

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
attcggtgct acctgtgtca caaacgctgt gtga                                34

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
attcgttgtt acctgtgtca caagccgttg tgtga                               35

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
attcgctgtg ctatatgtca aaagccttta tcaca                               35

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 51
attagatgct gtaagtgtca caagccatta tcacc                              35

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atacgctgct atttgtgcca caaaccattg tacca                              35

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
attaggtgta ttayytgtca aarrccrttg tgtcc                              35

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
attaggtgta ttaaytgtca aarrccrctg tgtcc                              35

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
attaggtgta ttayatgtca aarrccrctg tgtcc                              35

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
attaggtgta taaygtgtca aarrccrttg tgtcc                              35

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
```
attagatgta taayytgtca aacrccrtta tgtcc        35

<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
attaggtgta ttayatgtca aarrcctttg tgtcc        35

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
attagatgta ttayytgtca aarrccrttg tgtcc        35

<210> SEQ ID NO 60
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
attcggtgct accygtgtca carrccrctg tgtga        35

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
attcgttgtt accygtgtca carrccrttg tgtga        35

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
attcgctgtg ctayatgtca aarrccttta tcaca        35

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
attagatgct gtaagtgtca carrccrtta tcacc        35

<210> SEQ ID NO 64
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atacgctgct attygtgcca carrccrttg tgcca                              35

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cgaccctaca agctacctga tcttgca                                       27

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cgaccctaca agctaccaga ttttgca                                       27

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cggccataca aattgccaga ccttgca                                       27

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cggccataca aattgccaga ccttgca                                       27

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cggccataca aattgcctga ccttgca                                       27

```
<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cgaccataca aactgcctga tttagca                                          27

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cgaccctaca aactacctga ttttgca                                          27

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cgaccctaca agctacctga tcttgca                                          27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cgaccctaca agctaccaga ttttgca                                          27

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cggccataca aattgccaga ccttgca                                          27

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cggccataca aattgccaga ccttgca                                          27

<210> SEQ ID NO 76
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cggccataca aattgcctga ccttgca                                        27

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cgaccataca aactgcctga tttagca                                        27

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gcaacgacca tagaccagtt tgca                                           24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcaacatcta tagaccagtt tgca                                           24

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gagccacgca cattatacca ttttgca                                        27

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcacggacta tatttgagtt tgca                                           24

<210> SEQ ID NO 82
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 82
gcacaaagta tagaccagtt tgca                                              24

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cggccataca aattgccaga ccttgca                                           27

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cgaccctaca agctacctga tcttgca                                           27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cgaccctaca agctaccaga ttttgca                                           27

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cggccataca aattgccaga ccttgca                                           27

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cggccataca aattgccaga ccttgca                                           27

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 88
cggccataca aattgcctga ccttgca         27

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cgaccataca aactgcctga tttagca         27

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcaacgacca tagaccagtt tgca         24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gcaacatcta tagaccagtt tgca         24

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cagccacgca cattatacca ccttgca         27

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gcacggacta tatttgagtt tgca         24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 94
gcaacaagta tagaccagtt tgca                                          24

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
acagaggtat ttgaatttgc                                               20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
acagaggtat atcaatttgc                                               20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
accgaggtat atgaatttgc                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
acagaggtat atgaatttgc                                               20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
acagaggtat atgaatttgc                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
```
agagaggtat ttgaatttgc                                          20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gcagagaatt attcatatgc                                          20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcagagatat atgcatatgc                                          20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcagaggtgc tcgcgtacca                                          20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
acggaagtat tatcgtttgc                                          20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaatctggac gttcagttgc                                          20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
acagaggtat atgaatttgc                                          20

```
<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
acagaggtat ttgaatttgc                                                   20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
acagaggtat atcaatttgc                                                   20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
accgaggtat atgaatttgc                                                   20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
acagaggtat atgaatttgc                                                   20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
acagaggtat atgaatttgc                                                   20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
agagaggtat ttgaatttgc                                                   20

<210> SEQ ID NO 113
```

<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
gcagagaatt attcatatgc					20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
gcagagatat atgcatatgc					20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
gcagaggtgc tcgcgtacca					20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
acggaagtat tatcgtttgc					20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
aaatctggac gttcagttgc					20

<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
gagaattaag acattattca gactctgtgt atg					33

<210> SEQ ID NO 119
<211> LENGTH: 33
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 119
gagaattaag atattattca aactctgtat atg                              33

<210> SEQ ID NO 120
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gggagctacg atattactcg gactcggtgt atg                              33

<210> SEQ ID NO 121
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gggaactacg atattactca gaatcggtgt atg                              33

<210> SEQ ID NO 122
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gggaactacg gcattattcg aactcggtgt atg                              33

<210> SEQ ID NO 123
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gagaattaag atattattga gactccgtgt atg                              33

<210> SEQ ID NO 124
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gagaattaag atattattca gactctgtgt atg                              33

<210> SEQ ID NO 125
<211> LENGTH: 33
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 125
gagaattaag acattattca gactctgtgt atg                                    33

<210> SEQ ID NO 126
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gagaattaag atattattca aactctgtat atg                                    33

<210> SEQ ID NO 127
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gagaattaag atattattga gactccgtgt atg                                    33

<210> SEQ ID NO 128
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
accaatatag acactttgat tatgctggat atg                                    33

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
accaatatga cactttaatt atgctgcata tg                                     32

<210> SEQ ID NO 130
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gtgcactgcg acactacgaa agatcagcat ttt                                    33

<210> SEQ ID NO 131
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 131
gtcaatatag gcactttgac tacgcagcat atg                              33

<210> SEQ ID NO 132
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
atcaatttag gcattttaac tacgcgggat atg                              33

<210> SEQ ID NO 133
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gggaactacg gtattactcg gactcggtgt atg                              33

<210> SEQ ID NO 134
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gggagctacg atattactcg gactcggtgt atg                              33

<210> SEQ ID NO 135
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gggaactacg atattactca gaatcggtgt atg                              33

<210> SEQ ID NO 136
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gggaactacg gcattactcg aactccgtgt atg                              33

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
```
accaatatag acactttgat tatgctggat atg    33

<210> SEQ ID NO 138
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
accaatatag acactttaat tatgctgcat atg    33

<210> SEQ ID NO 139
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gtgcactgcg acactacgaa agatcagcat ttt    33

<210> SEQ ID NO 140
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gtcaatatag gcactttgac tacgcagcat atg    33

<210> SEQ ID NO 141
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
atcaatttag gcattttaac tacgcgggat atg    33

<210> SEQ ID NO 142
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
grgaaytacg atattaytcr ractctgtgt atg    33

<210> SEQ ID NO 143
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
grgaaytaag acattaytcr ractctgtgt atg    33

<210> SEQ ID NO 144
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
grgaaytaag atattaytcr ractctgtat atg                                33

<210> SEQ ID NO 145
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
grgagytacg atattaytcr ractcggtgt atg                                33

<210> SEQ ID NO 146
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
grgaaytacg atattaytcr raatcggtgt atg                                33

<210> SEQ ID NO 147
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
grgaaytacg gcattaytcr ractcggtgt atg                                33

<210> SEQ ID NO 148
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
grgaaytaag atattaytgr ractccgtgt atg                                33

<210> SEQ ID NO 149
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
accaayatag acacttygat tatgctggat atg                                33

```
<210> SEQ ID NO 150
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
accaayatag acacttyaat tatgctgcat atg                                  33

<210> SEQ ID NO 151
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gtgcaytgcg acactaygar rgatcagcat ttt                                  33

<210> SEQ ID NO 152
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gtcaayatag gcacttygac tacgcagcat atg                                  33

<210> SEQ ID NO 153
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
atcaayttag gcatttyaac tacgcgggat atg                                  33

<210> SEQ ID NO 154
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gttatacaat ttattaataa ggtgc                                           25

<210> SEQ ID NO 155
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gttgtataat tttttaataa ggtgc                                           25

<210> SEQ ID NO 156
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gttatataat ttattaataa ggtgc                                              25

<210> SEQ ID NO 157
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gttatatgat ttatcaataa ggtgc                                              25

<210> SEQ ID NO 158
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gttatataat ttatcaataa ggtgc                                              25

<210> SEQ ID NO 159
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gttacatgag cttctagtaa cgcgt                                              25

<210> SEQ ID NO 160
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
catcttagac gttctaattc ggtgc                                              25

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tattttaaaa gttttaattc gttgt                                              25

<210> SEQ ID NO 162
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 162
tttagaagaa taacaaatta gatgt                                           25

<210> SEQ ID NO 163
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
agtgtttgat ttgtgcatta gatgc                                           25

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
aattctggac gttctgatac gctgt                                           25

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gttatatgat ttattaataa ggtgc                                           25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gttatacaat ttattaataa ggtgc                                           25

<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gttgtataat ttttaataa ggtgc                                            25

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 168
gttatatatt tattaataag gtgc                                          24

<210> SEQ ID NO 169
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gttatatgat ttatcaataa ggtgc                                         25

<210> SEQ ID NO 170
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gttatataat ttatcaataa ggtgc                                         25

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gttacatgag cttctagtaa cgcgt                                         25

<210> SEQ ID NO 172
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
catcttagac gttctaattc ggtgc                                         25

<210> SEQ ID NO 173
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tattttagaa gttttaattc gttgt                                         25

<210> SEQ ID NO 174
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 174
tttagaagaa taacaaatta gatgt                                              25

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
agtgtttgat ttgtgcatta gatgc                                              25

<210> SEQ ID NO 176
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
aattctggac gttctgatac gctgt                                              25

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gttacatgag cttctagtaa cgcgt                                              25

<210> SEQ ID NO 178
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ccatatgcag tatgcaaaca atgttta                                            27

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ccttatgcag tgtgcagagt atgttta                                            27

<210> SEQ ID NO 180
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
```
ccatatgcag tatgtagggt atgttta                                              27

<210> SEQ ID NO 181
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ccgtatggag tgtgcaaatt ctgtttg                                              27

<210> SEQ ID NO 182
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ccatatgcag cctgcgcgtg ctgccta                                              27

<210> SEQ ID NO 183
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ccctttgcag cgtgtgcctg ttgctta                                              27

<210> SEQ ID NO 184
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ccatatgctg catgtgcatt ttgttta                                              27

<210> SEQ ID NO 185
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ccgtttgctg catgcttggc ctgtcta                                              27

<210> SEQ ID NO 186
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ccatttgcag ccgtgccatt tgttta                                               26

```
<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ccatatgcag tatgcagact atgttta                                              27

<210> SEQ ID NO 188
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ccatatgcag tatgcaaaca atgttta                                              27

<210> SEQ ID NO 189
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ccttatgcag tgtgcagagt atgttta                                              27

<210> SEQ ID NO 190
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ccatatgcag tatgtagggt atgttta                                              27

<210> SEQ ID NO 191
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ccgtatggag tgtgcaaatt ctgttta                                              27

<210> SEQ ID NO 192
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ccatatgcag cctgcgcgtg ctgccta                                              27

<210> SEQ ID NO 193
```

<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ccctttgcag cgtgtgcctg ttgctta                                       27

<210> SEQ ID NO 194
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ccatatgctg catgtgcatt ttgttta                                       27

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ccgtttgctg catgcttggc ctgtcta                                       27

<210> SEQ ID NO 196
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ccatttgcag cctgtgccat ttgttta                                       27

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cttatatgat ttatcgataa cgtg                                          24

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gttatgtgat ttattaataa cgtg                                          24

<210> SEQ ID NO 199
<211> LENGTH: 24
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 199
gttatctgat ttattaataa cgtg                                          24

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gttatctgat ttatcaataa cgtg                                          24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
catcttagac gttccaattc cgtg                                          24

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tattttaaaa gtttcaattc cttg                                          24

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tttagaagaa caacaaatta catg                                          24

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
agtgtttgat ttgtgcatta catg                                          24

<210> SEQ ID NO 205
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 205
aattctggac gttccgatac cctg                                              24

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gttatatgat ttattgataa ggtg                                              24

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cttatatgat ttatcgataa ggtg                                              24

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gttatgtgat ttattaataa ggtg                                              24

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gttatctgat ttattaataa ggtg                                              24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gttatctgat ttatcaataa ggtg                                              24

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 211
caactagacg ttctaattcg gtg                                              23

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tattttaaaa gttttaattc gttg                                             24

<210> SEQ ID NO 213
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tttagaagaa caacaaatta ggatg                                            25

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
agtgtttgat ttgtgcatta gatg                                             24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
aattctggac gttctgatac gctg                                             24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gttatatgat ttattaataa ggtg                                             24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
```

```
cttatatgat ttatcgataa ggtg                                          24
```

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218

```
gttatgtgat ttattaataa ggtg                                          24
```

<210> SEQ ID NO 219
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219

```
gttatctgat ttatttaata aggtg                                         25
```

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220

```
aatagcggga cgttggacgg gg                                            22
```

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221

```
aatagcacat ggttggaccg gg                                            22
```

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222

```
tatagcatat gcatggaccg gg                                            22
```

<210> SEQ ID NO 223
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223

```
aatttcacat atgtggaccg gg                                            22
```

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
aatagcggat cgttggaccg gg                                            22

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aatagcggga cgttggacgg gg                                            22

<210> SEQ ID NO 226
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
aatagcacat ggttggaccg gg                                            22

<210> SEQ ID NO 227
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tatagcatat gcatggaccg gg                                            22

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
aatttcacat atgtggaccg gg                                            22

<210> SEQ ID NO 229
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gctaaattgt acgtggaagg gt                                            22

```
<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
actaaataac cagtggaagg gt                                             22

<210> SEQ ID NO 231
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tatattgtgt cagtggacgg gt                                             22

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
aatacatagc gtgtggacag gg                                             22

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
attacaagat acctggaagg gt                                             22

<210> SEQ ID NO 234
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tctaaaataa gtgagtatag acattat                                        27

<210> SEQ ID NO 235
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tcaaaagtaa gtgaatatag atggtat                                        27

<210> SEQ ID NO 236
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
cgaccctaca aactacctga ttttgca                                            27

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
catacaaatt gccagacctt gca                                                23

<210> SEQ ID NO 238
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ccatatgcag tatgcagact atgttta                                            27

<210> SEQ ID NO 239
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ggacacaayg gyytttgaca rrtaatacac ctaat                                   35

<210> SEQ ID NO 240
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
catacacagt gtctgaataa tatcttaa                                           28

<210> SEQ ID NO 241
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
catacaccga gtccgagtaa taccgtag                                           28

<210> SEQ ID NO 242
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 242
cccggtccaa cgatccgcta tt                                              22

<210> SEQ ID NO 243
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
caactgatct ctactgttat gagcaatt                                        28

<210> SEQ ID NO 244
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
caactgacct atactgttat gagcaatt                                        28

<210> SEQ ID NO 245
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
caactgacct ccactgttat gagcaatt                                        28

<210> SEQ ID NO 246
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
caactgacct acactgctat gagcaatt                                        28

<210> SEQ ID NO 247
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
caactgacct atactgctat gagcaatt                                        28

<210> SEQ ID NO 248
<211> LENGTH: 28
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 248
caactgacct attctgctat gagcaatt                                        28

<210> SEQ ID NO 249
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ctgtagggtt acattgctat gagcaatt                                        28

<210> SEQ ID NO 250
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ctgtagggtt acattgctat gagcaatt                                        28

<210> SEQ ID NO 251
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ccattgacct gtattgctat gaacaatt                                        28

<210> SEQ ID NO 252
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ctgtaggcct acattgcaat gagcaatt                                        28

<210> SEQ ID NO 253
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
caactgacct ctactgctat gagcaatt                                        28

<210> SEQ ID NO 254
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 254
caactgatct ctactgttat gagcaatt                                              28

<210> SEQ ID NO 255
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
caactgacct atactgttat gagcaatt                                              28

<210> SEQ ID NO 256
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
caactgacct ccactgttat gagcaatt                                              28

<210> SEQ ID NO 257
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
caactgacct acactgctat gagcaatt                                              28

<210> SEQ ID NO 258
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
caactgacct atactgctat gagcaatt                                              28

<210> SEQ ID NO 259
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
caactgacct attctgctat gagcaatt                                              28

<210> SEQ ID NO 260
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
```

```
ctgtagggtt acattgctat gagcaatt                                          28
```

<210> SEQ ID NO 261
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261

```
ctgtagggtt acattgctat gagcaatt                                          28
```

<210> SEQ ID NO 262
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262

```
ccattgacct gtattgctat gaacaatt                                          28
```

<210> SEQ ID NO 263
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263

```
ctgtaggcct acattgcaat gagcaatt                                          28
```

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264

```
gacagctcag aggaggagga                                                   20
```

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265

```
gacagctcag aggaggagga                                                   20
```

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266

```
gacagctcag atgaggagga                                                   20
```

-continued

```
<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gacagctcag atgaggagga                                               20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gacagctcag atgaggatga                                               20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gacagctcag acgaggatga                                               20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gacagctcag aagatgaggt                                               20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gacagctcag aagatgaggt                                               20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gacagctcag atgaagatga                                               20

<210> SEQ ID NO 273
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gacagctcag aagaggatga                                                    20

<210> SEQ ID NO 274
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gttgaccttc tatgtcacga gcaatt                                             26

<210> SEQ ID NO 275
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gttgaccttg tatgtcacga gcaatt                                             26

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gttgacctgt tgtgttacga gcaatt                                             26

<210> SEQ ID NO 277
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gttgaccttg tgtgctacga gcaatt                                             26

<210> SEQ ID NO 278
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gtcgaccttg tatgtcacga gcaatt                                             26

<210> SEQ ID NO 279
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 279
gtcgaccttg tatgtcacga gcaatt                                              26

<210> SEQ ID NO 280
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
gtagggttac attgctatga gcaatt                                              26

<210> SEQ ID NO 281
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
gtagggttac attgctatga gcaatt                                              26

<210> SEQ ID NO 282
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
attgacctgt attgctatga acaatt                                              26

<210> SEQ ID NO 283
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
gtagggttac attgcaatga gcaatt                                              26

<210> SEQ ID NO 284
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gttgaccttc tatgttacga gcaatt                                              26

<210> SEQ ID NO 285
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 285
gttgaccttc tatgtcacga gcaatt                                              26

<210> SEQ ID NO 286
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gttgaccttc tatgtcacga gcaatt                                              26

<210> SEQ ID NO 287
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
gttgacctgt tgtgttacga gcaatt                                              26

<210> SEQ ID NO 288
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gttgaccttc tgtgctacga gcaatt                                              26

<210> SEQ ID NO 289
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gtcgaccttc tatgtcacga gcaatt                                              26

<210> SEQ ID NO 290
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gtcgaccttc tatgtcacga gcaatt                                              26

<210> SEQ ID NO 291
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 291
gtagggttac attgctatga gcaatt                                          26

<210> SEQ ID NO 292
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gtagggttac attgctatga gcaatt                                          26

<210> SEQ ID NO 293
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
attgacctgt attgctatga acaatt                                          26

<210> SEQ ID NO 294
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
gtagggttac attgcaatga gcaatt                                          26

<210> SEQ ID NO 295
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tcagaggaag aaaacgatga aatagatgga gtta                                 34

<210> SEQ ID NO 296
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
tcagaggagg aaaacgatga accagatgga gtta                                 34

<210> SEQ ID NO 297
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
```

```
tcagaggatg aaatagatga acccgaccat gcag                               34
```

<210> SEQ ID NO 298
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298

```
tcagacgatg aaatagatga acccgaccat gcag                               34
```

<210> SEQ ID NO 299
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299

```
tcagacaatg aaacagatga acccgaccat gtag                               34
```

<210> SEQ ID NO 300
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300

```
tccgagaatg aaaaagatga accagatgga gtta                               34
```

<210> SEQ ID NO 301
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301

```
tcagaagaag aaatggacga agtggatgga gtta                               34
```

<210> SEQ ID NO 302
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302

```
tcagaagaag aaatggacaa ggtggataga gtta                               34
```

<210> SEQ ID NO 303
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303

```
tcagaagaag aaatggatga actagctacg gtta                               34
```

<210> SEQ ID NO 304
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tcagatgaag atgaccaagc caaacaggac atac                                34

<210> SEQ ID NO 305
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
tcagaggaag aaaacgatga aacagatgga gtta                                34

<210> SEQ ID NO 306
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
tcagaggaag aaaacgatga aatagatgga gtta                                34

<210> SEQ ID NO 307
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
tcagaggagg aaaacgatga accagatgga gtta                                34

<210> SEQ ID NO 308
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tcagaggatg aaatagatga acccgaccat gcag                                34

<210> SEQ ID NO 309
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tcagacgatg aaatagatga acccgaccat gcag                                34

<210> SEQ ID NO 310
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tcagacaatg aaacagatga acccgaccat gtag                              34

<210> SEQ ID NO 311
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
tccgagaatg aaaagatga accagatgga gtta                               34

<210> SEQ ID NO 312
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
tcagaagaag aaatggacga agtggatgga gtta                              34

<210> SEQ ID NO 313
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tcagaagaag aaatggacaa ggtggataga gtta                              34

<210> SEQ ID NO 314
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tcagaagaag aaatggatga actagctacg gtta                              34

<210> SEQ ID NO 315
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tcagatgaag atgaccaagc caaacaggac atac                              34

<210> SEQ ID NO 316
<211> LENGTH: 34

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tcagacgatg aaacagatga acccgaccat gcag                               34

<210> SEQ ID NO 317
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tcagaggaag aaaacgatga aatagatgga gtta                               34

<210> SEQ ID NO 318
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tcagaggagg aaaacgatga accagatgga gtta                               34

<210> SEQ ID NO 319
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tcagaggatg aaatagatga acccgaccat gcag                               34

<210> SEQ ID NO 320
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tcagacgatg aaatagatga acccgaccat gcag                               34

<210> SEQ ID NO 321
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tcagacaatg aaacagatga acccgaccat gtag                               34

<210> SEQ ID NO 322
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 322
tccagagaat gaaaaagatg aaccagatgg agtta                              35

<210> SEQ ID NO 323
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
tcagaagaag aaatggacga agtggatgga gtta                               34

<210> SEQ ID NO 324
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tcagaagaag aaatggacaa ggtggataga gtta                               34

<210> SEQ ID NO 325
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tcagaagaag aaatggatga actagctacg gtta                               34

<210> SEQ ID NO 326
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tcagatgaag atgaccaagc caaacaggac atac                               34

<210> SEQ ID NO 327
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gaaattgact tgcaatgcta cgagcaatt                                     29

<210> SEQ ID NO 328
<211> LENGTH: 29
<212> TYPE: DNA
<213> ORGANISM: Artificial Sequence
<220> FEATURE:
<223> OTHER INFORMATION: Description of Artificial Sequence: Synthetic
```

```
                        oligonucleotide

<400> SEQUENCE: 328
gaaattgacc tacagtgcaa tgagcaatt                                          29

<210> SEQ ID NO 329
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gaaattgacc tacaatgcaa tgagcaatt                                          29

<210> SEQ ID NO 330
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gagattgacc tgcaatgcca tgagcaatt                                          29

<210> SEQ ID NO 331
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
cctgtagggt tacattgcta tgagcaatt                                          29

<210> SEQ ID NO 332
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
cctgtagggt tacattgcta tgagcaatt                                          29

<210> SEQ ID NO 333
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
cccattgacc tgtattgcta tgaacaatt                                          29

<210> SEQ ID NO 334
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 334
cctgtaggcc tacattgcaa tgagcaatt                                29

<210> SEQ ID NO 335
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gaaattgact acaatgcaa cgagcaatt                                 29

<210> SEQ ID NO 336
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
gaaattgact tgcaatgcta cgagcaatt                                29

<210> SEQ ID NO 337
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gaaattgacc tacagtgcaa tgagcaatt                                29

<210> SEQ ID NO 338
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gaaattgacc tacaatgcaa tgagcaatt                                29

<210> SEQ ID NO 339
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gagattgacc tgcaatgcca tgagcaatt                                29

<210> SEQ ID NO 340
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
```

```
cctgtagggt tacattgcta tgagcaatt                                    29
```

<210> SEQ ID NO 341
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341

```
cctgtagggt tacattgcta tgagcaatt                                    29
```

<210> SEQ ID NO 342
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342

```
cccattgacc tgtattgcta tgaacaatt                                    29
```

<210> SEQ ID NO 343
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343

```
cctgtaggcc tacattgcaa tgagcaatt                                    29
```

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344

```
gacagctcag aggaggagga tga                                          23
```

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345

```
gacagctcag aggatgagga tga                                          23
```

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346

```
gacagctcag aggatgagga tga                                          23
```

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
aacagctcag aggatgagga tga                                              23

<210> SEQ ID NO 348
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gacagctcag aagatgaggt gga                                              23

<210> SEQ ID NO 349
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gacagctcag aagatgaggt gga                                              23

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gacagctcag atgaagatgt gga                                              23

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gacagctcag aagaggaggt gga                                              23

<210> SEQ ID NO 352
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
agacgggctg gacaggctac gtgttac                                          27

<210> SEQ ID NO 353

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
agacaagcta aacaacatac gtgttac                                              27

<210> SEQ ID NO 354
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
agacaagcta aacaacataa gtgttac                                              27

<210> SEQ ID NO 355
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
agacgggacg aacaacatcc ttgttac                                              27

<210> SEQ ID NO 356
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
agacgagcta gacaagctac gtgttac                                              27

<210> SEQ ID NO 357
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
agacgggctg gacaggctac gtgttac                                              27

<210> SEQ ID NO 358
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
agacaagcta aacaacatac gtgttac                                              27

<210> SEQ ID NO 359
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 359
agacaagcta aacaacataa gtgttac                                           27

<210> SEQ ID NO 360
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
agacgggacg aacaacatcc ttgttac                                           27

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
caacctttaa aacaacatta c                                                 21

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
caacctttaa cacaacatta c                                                 21

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
aaacaggaca tacagcgtta c                                                 21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
caagacgtta cacagcctta c                                                 21

<210> SEQ ID NO 365
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 365
tgctcatagc agtagaggtc agttg                                              25

<210> SEQ ID NO 366
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
aattgctcgt aacatacaag gtcaac                                             26

<210> SEQ ID NO 367
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
aattgctcgt tgcattgtaa gtcaatttc                                          29

<210> SEQ ID NO 368
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
attaggtgta ttayytgtca aarrccrttg tgtcc                                   35

<210> SEQ ID NO 369
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
grgaaytacg atattaytcr ractctgtgt atg                                     33

<210> SEQ ID NO 370
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
attagcggat cgttggaccg gg                                                 22

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tcctcctcct ctgagctgtc                                              20

<210> SEQ ID NO 372
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
taactccatc tgtttcatcg ttttc                                        25

<210> SEQ ID NO 373
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
ctgcatggtc gggttcatct gtttcat                                      27

<210> SEQ ID NO 374
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
caactgacct ctactgctat gagc                                         24

<210> SEQ ID NO 375
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gttgaccttg tatgttacga gcaatt                                       26

<210> SEQ ID NO 376
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gaaattgact tacaatgcaa cgagcaatt                                    29

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377

```
atggctgatc ctgcaggtac                                              20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
atggctgatc ctgcaggtac                                              20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
atggctgatc cagcaggtac                                              20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
atggaggacc ctgaaggtac                                              20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
atggccgatc ctgaaggtac                                              20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
atggatgacc ctgaaggtac                                              20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
atggctgacg attcaggtac                                              20
```

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
atggctgacg attcaggtac                                              20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
atggctgaca atacaggtac                                              20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
atggcggatg atacaggtac                                              20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
atggacgacc ctgaaggtac                                              20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
atggctcgtc ctgcaggtac                                              20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
atggctcgtc aagcaggtac                                              20

-continued

```
<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
atggctcgtc ctgcaggtac                                                 20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
atggaggacc ctgaaggtac                                                 20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
atggccgatc ctgaaggtac                                                 20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
atggatgacc ctgaaggtac                                                 20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
atggctgacg attcaggtac                                                 20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
atggctgacg attcaggtac                                                 20

<210> SEQ ID NO 396
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
atggctgaca atacaggtac                                                    20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
atggctgatg atacaggtac                                                    20

<210> SEQ ID NO 398
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gagacagcac atgcgttgtt tactgcacag ga                                      32

<210> SEQ ID NO 399
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
gagacagcac aagcattgtt tcatgcacag ga                                      32

<210> SEQ ID NO 400
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gagacagcac aggcattgtt tcatgcacag ga                                      32

<210> SEQ ID NO 401
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gaggcagccc gggcattgtt taatgcacag ga                                      32

<210> SEQ ID NO 402
<211> LENGTH: 32
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 402
gaggcagccc gggcattgtt taatatacag ga                                 32

<210> SEQ ID NO 403
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
gaggcagccc gagcgttgtt taatgtacag ga                                 32

<210> SEQ ID NO 404
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gagacagcat atgcattgtt taatgcacag ga                                 32

<210> SEQ ID NO 405
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gagacagcat atgcgttgtt tactgcacag ga                                 32

<210> SEQ ID NO 406
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gagacagcat aagcattgtt tcatgcacag ga                                 32

<210> SEQ ID NO 407
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
gagacagcat aggcattgtt tcatgcacag ga                                 32

<210> SEQ ID NO 408
<211> LENGTH: 32
<212> TYPE: DNA
<213> ORGANISM: Artificial Sequence
<220> FEATURE:
<223> OTHER INFORMATION: Description of Artificial Sequence: Synthetic

```
            oligonucleotide

<400> SEQUENCE: 408
gaggcagcct gggcattgtt taatgcacag ga                                32

<210> SEQ ID NO 409
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
gaggcagcct gggcattgtt taatatacag ga                                32

<210> SEQ ID NO 410
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gaggcagcct gagcgttgtt taatgtacag ga                                32

<210> SEQ ID NO 411
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
ctggaagcat aggcattgtt taacaggcag ga                                32

<210> SEQ ID NO 412
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ctggaagcat aggcattgtt taataggcag ga                                32

<210> SEQ ID NO 413
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ctggaagcat aggccttatt aaataaacag ca                                32

<210> SEQ ID NO 414
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 414
gtacatgcat aagcattgtt aaacgagcag ga        32

<210> SEQ ID NO 415
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
gaggcagcct gggcattgtt taatgtacag ga        32

<210> SEQ ID NO 416
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gagacagcat atgcgttgtt tactgcacag ga        32

<210> SEQ ID NO 417
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
gagacagcat aagcattgtt tcatgcacag ga        32

<210> SEQ ID NO 418
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
gagacagcat aggcattgtt tcatgcacag ga        32

<210> SEQ ID NO 419
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
gaggcagcct gggcattgtt taatgcacag ga        32

<210> SEQ ID NO 420
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420

```
gaggcagcct gggcattgtt taatatacag ga                                         32

<210> SEQ ID NO 421
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
gaggcagcct gagcgttgtt taatgtacag ga                                         32

<210> SEQ ID NO 422
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
ctggaagcat aggcattgtt taacaggcag ga                                         32

<210> SEQ ID NO 423
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
ctggaagcat aggcattgtt taataggcag ga                                         32

<210> SEQ ID NO 424
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
ctggaagcac taggccttat taaataaaca gca                                        33

<210> SEQ ID NO 425
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gtacatgcat aggcattgtt aaacgagcag ga                                         32

<210> SEQ ID NO 426
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
caaagtttag catgttcatg gggaatggt                                             29
```

```
<210> SEQ ID NO 427
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
caatgtttat cgtgttcatg gggtatggt                                    29

<210> SEQ ID NO 428
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
caaagtttag catgttcctg gggcatggt                                    29

<210> SEQ ID NO 429
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
caatgtttaa catgtgacag aggcgtcgt                                    29

<210> SEQ ID NO 430
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
caatgtttaa cttgcgatag aggaataat                                    29

<210> SEQ ID NO 431
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
caatgtttaa cgtgtgacag aggaataat                                    29

<210> SEQ ID NO 432
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
caatggctaa caaatgcatg aggaatggt                                    29

<210> SEQ ID NO 433
```

<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
caatggctta caaatgcatg aggaatggt                                    29

<210> SEQ ID NO 434
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
caatggctaa cctgtgcgtg aggcatggt                                    29

<210> SEQ ID NO 435
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
caatggctta caaatgcatg aggaatggt                                    29

<210> SEQ ID NO 436
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
caaagtttag cgtgttcatg gggaatggt                                    29

<210> SEQ ID NO 437
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
caaagtttag catgttcatg gggaatggt                                    29

<210> SEQ ID NO 438
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
caatgtttat cgtgttcatg gggtatggt                                    29

<210> SEQ ID NO 439
<211> LENGTH: 29
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 439
caaagtttag catgttcctg gggcatggt                                              29

<210> SEQ ID NO 440
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
caatgtttaa catgtgacag aggcgtcgt                                              29

<210> SEQ ID NO 441
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
caatgtttaa cttgcgatag aggaataat                                              29

<210> SEQ ID NO 442
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
caatgtttaa cgtgtgacag aggaataat                                              29

<210> SEQ ID NO 443
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
caatggctaa caaatgcatg gggaatggt                                              29

<210> SEQ ID NO 444
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
caatggctta caaatgcatg gggaatggt                                              29

<210> SEQ ID NO 445
<211> LENGTH: 29
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 445
caatggctaa cctgtgcgtg gggcatggt                                       29

<210> SEQ ID NO 446
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
caatggctta caaatgcatg gggaatggt                                       29

<210> SEQ ID NO 447
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
caatgtttaa cttgtgacag agg                                             23

<210> SEQ ID NO 448
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
caaagtttag catgttcatg ggg                                             23

<210> SEQ ID NO 449
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
caatgtttat cgtgttcatg ggg                                             23

<210> SEQ ID NO 450
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
caaagtttag catgttcctg ggg                                             23

<210> SEQ ID NO 451
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
caatgtttaa catgtgacag agg                                            23

<210> SEQ ID NO 452
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
caatgtttaa cttgcgatag agg                                            23

<210> SEQ ID NO 453
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
caatgtttaa cgtgtgacag agg                                            23

<210> SEQ ID NO 454
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
caatggctaa caaatgcatg ggg                                            23

<210> SEQ ID NO 455
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
caatggctta caaatgcatg ggg                                            23

<210> SEQ ID NO 456
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
caatggctaa cctgtgcgtg ggg                                            23

<210> SEQ ID NO 457
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
caatggctta caaatgcatg ggg				23

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
gaaggtacag acggggaggg				20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
gaaggtacag acggggatgg				20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
gaaggtaccg acggggaggg				20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
gaaggtacag atggggaagg				20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
gaaggtacag atggggacgg				20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
gaaggtacag atggggatgg				20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
tcaggtacag aaaatgaggg                                               20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
tcaggtacag aaaatgaggg                                               20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
acaggtacag aggggggaggg                                              20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
acaggtacag agggaacggg                                               20

<210> SEQ ID NO 468
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
gaggacgaaa atgcaacaga cacagg                                        26

<210> SEQ ID NO 469
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
gaggatgaaa atgcaacaga tacagg                                        26

```
<210> SEQ ID NO 470
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
gaggatgaaa ctgcaacaga tacagg                                       26

<210> SEQ ID NO 471
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
gaggacgaaa atgcaacaga tacagg                                       26

<210> SEQ ID NO 472
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gaggatgaaa acgcaacaga tacagg                                       26

<210> SEQ ID NO 473
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
gaggacgaaa atgcgacaga tacagg                                       26

<210> SEQ ID NO 474
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
gaggatgaaa atgcaacaga tacagg                                       26

<210> SEQ ID NO 475
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gaggacgaaa atgcaacaga cacagg                                       26

<210> SEQ ID NO 476
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gaggatgaaa atgcaacaga tacagg                                          26

<210> SEQ ID NO 477
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gaggatgaaa ctgcaacaga tacagg                                          26

<210> SEQ ID NO 478
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
gaggacgaaa atgcaacaga tacagg                                          26

<210> SEQ ID NO 479
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
gaggatgaaa acgcaacaga tacagg                                          26

<210> SEQ ID NO 480
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
gaggacgaaa atgcgacaga tacagg                                          26

<210> SEQ ID NO 481
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
gaggacgagg aggtggagga cagtgg                                          26

<210> SEQ ID NO 482
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 482
gaggaagagg aggtggagga cagtgg                                            26

<210> SEQ ID NO 483
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
gaggacgaaa atgtagacga tagtgg                                            26

<210> SEQ ID NO 484
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
gaggacgagg cagtggagga agtagg                                            26

<210> SEQ ID NO 485
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
acaggcagag ctagagacag cacagg                                            26

<210> SEQ ID NO 486
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
acaggcagag caagagacag cacagg                                            26

<210> SEQ ID NO 487
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
acaggcagag cgtgagacag cacagg                                            26

<210> SEQ ID NO 488
<211> LENGTH: 26
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 488
acaggcagag cgtgagacag cacagg                                26

<210> SEQ ID NO 489
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
acaggcagag cgcgagacag cacagg                                26

<210> SEQ ID NO 490
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
acaggcagag cgcgagacag cacagg                                26

<210> SEQ ID NO 491
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
acaggcagag cgagagacag cacagg                                26

<210> SEQ ID NO 492
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
acaggcagag ctagagacag cacagg                                26

<210> SEQ ID NO 493
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
acaggcagag caagagacag cacagg                                26

<210> SEQ ID NO 494
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 494
acaggcagag cgtgagacag cacagg                                        26

<210> SEQ ID NO 495
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
acaggcagag cgtgagacag cacagg                                        26

<210> SEQ ID NO 496
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
acaggcagag cgcgagacag cacagg                                        26

<210> SEQ ID NO 497
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
acaggcagag cgcgagacag cacagg                                        26

<210> SEQ ID NO 498
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
acacaattca ctagaagcac agg                                           23

<210> SEQ ID NO 499
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
acaaaattct gtagaagcac agg                                           23

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
```

```
acatacaaag caagtagcac agg                                              23

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
acacaattcc atagaagcac agg                                              23

<210> SEQ ID NO 502
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
gcaggaggtc cacaatgatg cac                                              23

<210> SEQ ID NO 503
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gcaggaagtt cagaatgatg cac                                              23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
gcaagaggct caaagggatg cac                                              23

<210> SEQ ID NO 505
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
gcaacaggct caaagggatg cac                                              23

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
gcaagaggct caaagggatg cac                                              23
```

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
gcaggaagct caaagggatg cac                                              23

<210> SEQ ID NO 508
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
gcaggaagtc cagaatgatg cac                                              23

<210> SEQ ID NO 509
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
gcaggagtgc cacaatgatg cac                                              23

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
gcaggaagtt cagaatgatg cac                                              23

<210> SEQ ID NO 511
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
gcaagaggcc caaagggatg cac                                              23

<210> SEQ ID NO 512
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
gcaacaggcc caaagggatg cac                                              23

<210> SEQ ID NO 513

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
gcaacaggcc caaagggatg cac                                             23

<210> SEQ ID NO 514
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gcaggaagcc caaagggatg cac                                             23

<210> SEQ ID NO 515
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
gcaggaggcg gacacccatt atg                                             23

<210> SEQ ID NO 516
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
gcaggaggcg gatgctcatt atg                                             23

<210> SEQ ID NO 517
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
acaacaagca catgcagatc agg                                             23

<210> SEQ ID NO 518
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
gcaggaggcg gatgctcatt atg                                             23

<210> SEQ ID NO 519
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 519
gcaagaggcc caaagggatg cac                                           23

<210> SEQ ID NO 520
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
gcaggaggtc cacaatgatg cac                                           23

<210> SEQ ID NO 521
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
gcaggaagtt cagaatgatg cac                                           23

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
gcaagaggcc caaagggatg cac                                           23

<210> SEQ ID NO 523
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gcaacaggcc caaagggatg cac                                           23

<210> SEQ ID NO 524
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
gcaagaggcc caaagggatg cac                                           23

<210> SEQ ID NO 525
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 525
gcaggaagcc caaagggatg cac                                              23

<210> SEQ ID NO 526
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gcaggaggcg gacacccatt atg                                              23

<210> SEQ ID NO 527
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
gcaggaggcg gatgctcatt atg                                              23

<210> SEQ ID NO 528
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
acaacaagca catgcagatc agg                                              23

<210> SEQ ID NO 529
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
gcaggaggcg gatgctcatt atg                                              23

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
gaaggtacag acggggaggg                                                  20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 531
gaaggtacag aggatgaggg                                               20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gaaggtacag atggggaggg                                               20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gaaggtacag atggggaggg                                               20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
gaaggtacag atgatgaggg                                               20

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
gaaggtacag atggtgaggg g                                             21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
gaaggtacag aggatgaggg g                                             21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
```

```
gaaggtacag atggggaggg g                                              21
```

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538

```
gaaggtacag atggggaggg g                                              21
```

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539

```
gaaggtacag atgatgaggg g                                              21
```

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540

```
tcaggtacag aaaatgaggg g                                              21
```

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541

```
tcaggtacag aaaatgaggg g                                              21
```

<210> SEQ ID NO 542
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542

```
acaggtacag aggagggg                                                  18
```

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543

```
acaggtacag agggaacggg g                                              21
```

<210> SEQ ID NO 544
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
gaagcaatag tagaaaaaaa aacagga                                        27

<210> SEQ ID NO 545
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
gaggcaattg tagaaaaaaa aacagga                                        27

<210> SEQ ID NO 546
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
gaagcaattg tagaaagaaa aacgggg                                        27

<210> SEQ ID NO 547
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
gaggcaatag taaaaaaacg tacaggg                                        27

<210> SEQ ID NO 548
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gaagcaattg tagaaaaaaa aacagga                                        27

<210> SEQ ID NO 549
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
gaagcaatag tagaaaaaaa aacagga                                        27

-continued

```
<210> SEQ ID NO 550
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
gaggcaattg tagaaaaaaa aacagga                                           27

<210> SEQ ID NO 551
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
gaagcaattg tagaaagaaa aacgggg                                           27

<210> SEQ ID NO 552
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
gaggcaatag taaaaaaacg tacaggg                                           27

<210> SEQ ID NO 553
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
gaagctatag tgcaacaccc aacaggt                                           27

<210> SEQ ID NO 554
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
gaagccatag tagagcacac tacaggt                                           27

<210> SEQ ID NO 555
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
gaagctatag tagacaaaac aacagaa                                           27

<210> SEQ ID NO 556
<211> LENGTH: 27
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
gaggctatag tggagaacac aaccggg                                         27

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
gataatgttt cggatgatga                                                 20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
gataaaatat cagatgatga                                                 20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gatacaatat cagatgatga                                                 20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
gatgtaatat ctgaagatga                                                 20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
gataaagttt cagatgatga                                                 20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
gataatgttt cggatgatga                                                      20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
gataaaatat cagatgatga                                                      20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
gatacaatat cagatgatga                                                      20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
gatgtaatat ctgaagatga                                                      20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
acacaaatat cagacgatga                                                      20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
acacaaatat cagaagatga                                                      20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 568
aatgctattt cagatgatga                                                    20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
caacaaatat cagaggatga                                                    20

<210> SEQ ID NO 570
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
ttatatgcac atatacaatg tttaacatgt                                          30

<210> SEQ ID NO 571
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
atgtactacc atatacaatg tttaacatgt                                          30

<210> SEQ ID NO 572
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
atgtattatc atatgcaatg tttaacatgt                                          30

<210> SEQ ID NO 573
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
gtgtactatc atatgcaatg tttaacatgt                                          30

<210> SEQ ID NO 574
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 574
atatattacc atatgcaatg tttaacatgt                                30

<210> SEQ ID NO 575
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
ttatatgccc atatacaatg gctaacaaat                                30

<210> SEQ ID NO 576
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
ttatatgccc atatacaatg gcttacaaat                                30

<210> SEQ ID NO 577
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
ttatataccc atatacaatg gctaacctgt                                30

<210> SEQ ID NO 578
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
ccatatagcc acatacaatg gcttacaaat                                30

<210> SEQ ID NO 579
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
atgtactatc atatgcaatg tttatcatgt                                30

<210> SEQ ID NO 580
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
```

```
atgtactacc atatacaatg tttatcatgt                                    30
```

<210> SEQ ID NO 581
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581

```
atgtattatc atatgcaatg ttaaacatgt                                    30
```

<210> SEQ ID NO 582
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582

```
gtgtactatc atatgcaatg tttaacatgt                                    30
```

<210> SEQ ID NO 583
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583

```
atatattacc atatgcaatg tttaacatgt                                    30
```

<210> SEQ ID NO 584
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584

```
ttatatgccc atatacaatg gctaacaaat                                    30
```

<210> SEQ ID NO 585
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585

```
ttatatgccc atatacaatg gcttacaaat                                    30
```

<210> SEQ ID NO 586
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586

```
ttatataccc atatacaatg gctaacctgt                                    30
```

<210> SEQ ID NO 587
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
ccatatagcc acatacaatg gcttacaaat                                        30

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
tatggcwrtw ctgaagtgga a                                                 21

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
tatggcaata ctgaagtgga a                                                 21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
tatggcatta ctgaagtgga a                                                 21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
tatggcaata ctgaagtgga a                                                 21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
tatggcaata gtgaagtgga a                                                 21

<210> SEQ ID NO 593

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
tatggcaata ctgaagtgga a                                            21

<210> SEQ ID NO 594
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
tatggcaata ctgaagtgga a                                            21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
tatggctgtt ctgaagtgga a                                            21

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
tatggctgtt ctgaagtgga a                                            21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
tatggcaata tggaagtgga a                                            21

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, g, or t

<400> SEQUENCE: 598
tattcanata tggaagtgga a                                            21
```

<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
tatggcaata tggaagtgga a                                              21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
tatggctatt ctgaagtgga a                                              21

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
tatggcaata cacaagtgga a                                              21

<210> SEQ ID NO 602
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
tatggcaata cattggaa                                                  18

<210> SEQ ID NO 603
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
tatggcaata cattggaa                                                  18

<210> SEQ ID NO 604
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
tatggcaata ctttggaa                                                  18

<210> SEQ ID NO 605

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
tatggctatt ctgaagtgga a                                              21

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
tatggctatt ctgaagtgga a                                              21

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
tatggctatt ctgaagtgga a                                              21

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
tatggcaata ctgaagtgga a                                              21

<210> SEQ ID NO 609
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
caactgacct ctactgctat gagca                                          25

<210> SEQ ID NO 610
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
aagaaaacga tgaaacagat ggagtta                                        27

<210> SEQ ID NO 611
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 611
atgaaacaga tgaacccgac catg                                              24

<210> SEQ ID NO 612
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
gaaattgact tacaatgcaa cgagcaat                                          28

<210> SEQ ID NO 613
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
gagacagcat atgcattgtt taatgc                                            26

<210> SEQ ID NO 614
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
gaggcagcct gggcattgtt taat                                              24

<210> SEQ ID NO 615
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
aggcagagcg agagacagca ca                                                22

<210> SEQ ID NO 616
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
gaagcaattg tagaaaaaaa aacagga                                           27

<210> SEQ ID NO 617
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 617
atggctgatc ctgcaggtac                                                    20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
atggacgacc ctgaaggtac                                                    20

<210> SEQ ID NO 619
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
gaggatgaaa atgcaacaga tacagg                                             26

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
gaaggtacag atggtgaggg g                                                  21

<210> SEQ ID NO 621
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
gcattaaaca atgcatatgc tgtctc                                             26

<210> SEQ ID NO 622
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
attaaacaat gcccaggctg cctc                                               24

<210> SEQ ID NO 623
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 623
tgtgctgtct ctcgctctgc ct                                              22

<210> SEQ ID NO 624
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
tgctgttttt ttttctacaa ttg                                             23

<210> SEQ ID NO 625
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
taccatattt tttttcagat gtctct                                          26

<210> SEQ ID NO 626
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
tcccatattt ttttgcagat gtctct                                          26

<210> SEQ ID NO 627
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
tatcatattt ttttacagat gtctct                                          26

<210> SEQ ID NO 628
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
ttccatattt ttttacagat gtccgt                                          26

<210> SEQ ID NO 629
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
```
ttccatattt ttttacagat gtccgt                                          26

<210> SEQ ID NO 630
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
ttccatattt ttttgcagat gtccgt                                          26

<210> SEQ ID NO 631
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
ttcccttatt tttttcagat gtgggg                                          26

<210> SEQ ID NO 632
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
ttcccttatt ttttacagat gtgggg                                          26

<210> SEQ ID NO 633
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
taccatattt ttttgcagat gtccgt                                          26

<210> SEQ ID NO 634
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
ttctcttgtt ttttgcagat gtgggg                                          26

<210> SEQ ID NO 635
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
ttccatattt ttttacagat gtccgt                                          26

<210> SEQ ID NO 636
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
taccatattt tttttcagat gtctct                                        26

<210> SEQ ID NO 637
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
tcccatattt ttttgcagat gtctct                                        26

<210> SEQ ID NO 638
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
tatcatattt ttttacagat gtctct                                        26

<210> SEQ ID NO 639
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
ttccatattt ttttacagat gtccgt                                        26

<210> SEQ ID NO 640
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
ttccatattt ttttacagat gtccgt                                        26

<210> SEQ ID NO 641
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
ttccatattt ttttgcagat gtccgt                                        26

```
<210> SEQ ID NO 642
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
ttcccttatt tttttcagat gtggcg                                          26

<210> SEQ ID NO 643
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
ttcccttatt ttttacagat gtggcg                                          26

<210> SEQ ID NO 644
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
taccatattt ttttgcagat gtccgt                                          26

<210> SEQ ID NO 645
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
ttctcttgtt ttttgcagat gtggcg                                          26

<210> SEQ ID NO 646
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
ttccctattt ttttgcagat ggc                                             23

<210> SEQ ID NO 647
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
ttccctattt ttttgcagat ggc                                             23

<210> SEQ ID NO 648
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
ttccctattt tttttcagat ggc                                            23

<210> SEQ ID NO 649
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
ttccttattt ttttgcagat ggc                                            23

<210> SEQ ID NO 650
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
ttccctattt ttttacagat ggc                                            23

<210> SEQ ID NO 651
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
ttccctattt ttttacagat ggc                                            23

<210> SEQ ID NO 652
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
taccctattt ttttacagat ggc                                            23

<210> SEQ ID NO 653
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
ttccctattt ttttgcagat ggc                                            23

<210> SEQ ID NO 654
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 654 ttccctatttt tcttgcagat ggc                                             23

<210> SEQ ID NO 655
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655 ttccctatttt ttttacagat ggc                                             23

<210> SEQ ID NO 656
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656 ttccctatttt ttttgcagat ggc                                             23

<210> SEQ ID NO 657
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657 ttccctatttt ttttgcagat ggc                                             23

<210> SEQ ID NO 658
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658 ttccctatttt tttttcagat ggc                                             23

<210> SEQ ID NO 659
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659 ttccttatttt ttttacagat ggc                                             23

<210> SEQ ID NO 660
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                        oligonucleotide

<400> SEQUENCE: 660 ttccctatttt ttttacagat ggc                                              23

<210> SEQ ID NO 661
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661 ttccctatttt ttttacagat ggc                                              23

<210> SEQ ID NO 662
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662 taccctatttt ttttacagat ggc                                              23

<210> SEQ ID NO 663
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663 ttccctatttt ttttgcagat ggc                                              23

<210> SEQ ID NO 664
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664 ttccctatttt tcttgcagat ggc                                              23

<210> SEQ ID NO 665
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
ttcccttatt tttttcagat gtg                                               23

<210> SEQ ID NO 666
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 666
ttcccttatt ttttacagat gtg                                              23

<210> SEQ ID NO 667
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
taccatattt ttttgcagat gtc                                              23

<210> SEQ ID NO 668
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
tttccttgtt ttttgcagat gtg                                              23

<210> SEQ ID NO 669
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
gaggccactg tctacttgcc tcctgtccca gt                                    32

<210> SEQ ID NO 670
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
gaagccactg tctacctgcc tccagtgtca gt                                    32

<210> SEQ ID NO 671
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
gaggctactg tctacttacc acctgtccca gt                                    32

<210> SEQ ID NO 672
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
```

```
gaggccactg tgtacctgcc tcctgtacct gt                                    32

<210> SEQ ID NO 673
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
gaggccacag tgtacctgcc tcctgtccct gt                                    32

<210> SEQ ID NO 674
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
gaggccactg tgtacctgcc tcctgtccct gt                                    32

<210> SEQ ID NO 675
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
gacagcacag tatatgtgcc tcctcctaac cc                                    32

<210> SEQ ID NO 676
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
gacagcacag tatatgtgcc tcctcccaac cc                                    32

<210> SEQ ID NO 677
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
gacaacaagg tttatctgcc tcctcctcca gt                                    32

<210> SEQ ID NO 678
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
gaaaacaagg tatatgtgcc tcctcccgcc cc                                    32
```

<210> SEQ ID NO 679
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
gaggccactg tctacttgcc tcctgtgcca gt                              32

<210> SEQ ID NO 680
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
gaggccactg tctacttgcc tcctgtccca gt                              32

<210> SEQ ID NO 681
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
gaagccactg tctacctgcc tccagtgtca gt                              32

<210> SEQ ID NO 682
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
gaggctactg tctacttacc acctgtccca gt                              32

<210> SEQ ID NO 683
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
gaggccactg tgtacctgcc tcctgtacct gt                              32

<210> SEQ ID NO 684
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
gaggccaagt gtacctgcct cctgtccctg t                               31

<210> SEQ ID NO 685

```
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
gaggccactg tgtacctgcc tcctgtccct gt                                    32

<210> SEQ ID NO 686
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
gacagcacag tatatgtgcc tcctcctaac cc                                    32

<210> SEQ ID NO 687
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
gacagcacag tatatgtgcc tcctcccaac cc                                    32

<210> SEQ ID NO 688
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
gacaacaagg tttatctgcc tcctcctcca gt                                    32

<210> SEQ ID NO 689
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
gaaaacaagg tatatgtgcc tcctcccgcc cc                                    32

<210> SEQ ID NO 690
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
gaggccactg tgtacctgcc tcctgtccct gt                                    32

<210> SEQ ID NO 691
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 691
gaggccactg tctacttgcc tcctgtccca gt                                    32

<210> SEQ ID NO 692
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
gaagccactg tctacctgcc tccagtgtca gt                                    32

<210> SEQ ID NO 693
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
gaggctactg tctacttacc acctgtccca gt                                    32

<210> SEQ ID NO 694
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
gaggccactg tgtacctgcc tcctgtacct gt                                    32

<210> SEQ ID NO 695
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
gaggccacag tgtacctgcc tcctgtccct gt                                    32

<210> SEQ ID NO 696
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
gaggccactg tgtacctgcc tcctgtccct gt                                    32

<210> SEQ ID NO 697
<211> LENGTH: 32
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 697
gacagcacag tatatgtgcc tcctcctaac cc                                    32

<210> SEQ ID NO 698
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
gacagcacag tatatgtgcc tcctcccaac cc                                    32

<210> SEQ ID NO 699
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
gacaacaagg tttatctgcc tcctcctcca gt                                    32

<210> SEQ ID NO 700
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
gaaaacaagg tatatgtgcc tcctcccgcc cc                                    32

<210> SEQ ID NO 701
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
tatatcttcc acctccttct gtggcaagag ttgt                                  34

<210> SEQ ID NO 702
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
tatatcttcc accaccttct gtggccagag ttgt                                  34

<210> SEQ ID NO 703
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 703
tatatttgcc tccaccttct gtggcgaagg ttgt                                34

<210> SEQ ID NO 704
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
tgtatttgcc tcccccctca gtggcgaagg ttgt                                34

<210> SEQ ID NO 705
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
tgtatttgcc accccttct gtggcgaagg ttgt                                 34

<210> SEQ ID NO 706
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
tgtatctacc tccaccttct gtagctaagg ttgt                                34

<210> SEQ ID NO 707
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
tatatgtgcc tccacctaac cctgtatcca aagttgt                             37

<210> SEQ ID NO 708
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
tatatgtgcc tccacccaac cctgtatcca aggttgt                             37

<210> SEQ ID NO 709
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
```

```
tttatctacc tccacctcct gtttccaagg tggt                                    34
```

<210> SEQ ID NO 710
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710

```
tatatgtgcc tccacccgcc ccagtatcca aagtaat                                 37
```

<210> SEQ ID NO 711
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711

```
tatatcttcc accaccttct gtggcaagag ttgt                                    34
```

<210> SEQ ID NO 712
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712

```
tatatcttcc acctccttct gtggcaagag ttgt                                    34
```

<210> SEQ ID NO 713
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713

```
tatatcttcc accaccttct gtggccagag ttgt                                    34
```

<210> SEQ ID NO 714
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714

```
tatatttgcc tccaccttct gtggcgaagg ttgt                                    34
```

<210> SEQ ID NO 715
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715

```
tgtatttgcc tcccccctta gtggcgaagg ttgt                                    34
```

<210> SEQ ID NO 716
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
tgtatttgcc accccttct gtggcgaagg ttgt                    34

<210> SEQ ID NO 717
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
tgtatctacc tccaccttct gtagctaagg ttgt                   34

<210> SEQ ID NO 718
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
tatatgtgcc tcctcctaac cctgtatcca aagttgt                37

<210> SEQ ID NO 719
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
tatatgtgcc tcctcccaac cctgtatcca aggttgt                37

<210> SEQ ID NO 720
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
tttatctacc tcctcctcct gtttccaagg tggt                   34

<210> SEQ ID NO 721
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
tatatgtgcc tcctcccgcc ccagtatcca aagtaat                37

```
<210> SEQ ID NO 722
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
tatatttgcc tccaccttct gtggctaagg ttgt                                  34

<210> SEQ ID NO 723
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
tatatcttcc acctccttct gtggcaagag ttgt                                  34

<210> SEQ ID NO 724
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
tatatcttcc accaccttct gtggccagag ttgt                                  34

<210> SEQ ID NO 725
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
tatatttgcc tccaccttct gtggcgaagg ttgt                                  34

<210> SEQ ID NO 726
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
tgtatttgcc tcccccctca gtggcgaagg ttgt                                  34

<210> SEQ ID NO 727
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
tgtatttgcc accccttct gtggcgaagg ttgt                                   34

<210> SEQ ID NO 728
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
tgtatctacc tccaccttct gtaggctaag gttgt                              35

<210> SEQ ID NO 729
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
tatatgtgcc tcctcctaac cctgtatcca aggttgt                            37

<210> SEQ ID NO 730
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
tatatgtgcc tcctcccaac cctgtatcca aggttgt                            37

<210> SEQ ID NO 731
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
tttatctacc tcctcctcct gtttccaagg tggt                               34

<210> SEQ ID NO 732
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
tatatgtgcc tcctcccgcc ccagtatcca aagtaat                            37

<210> SEQ ID NO 733
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
caggatattc ctaaggtttc tgcat                                         25

<210> SEQ ID NO 734
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 734
caggctgttc ctaaggtatc cgcat                                               25

<210> SEQ ID NO 735
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
caggacattc caaaggtgtc tgcat                                               25

<210> SEQ ID NO 736
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
caggacattc ctaaggtgtc tgcat                                               25

<210> SEQ ID NO 737
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
caggaaattc ctaaggtgtc tgcat                                               25

<210> SEQ ID NO 738
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
caggatgttc ctaaggtgtc tgcat                                               25

<210> SEQ ID NO 739
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
actgttgtgc caaaggtgtc aggat                                               25

<210> SEQ ID NO 740
<211> LENGTH: 25
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 740
acagttgtac caaaggtgtc tggat					25

<210> SEQ ID NO 741
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
acatatatcc ccaaagtgtc tggtt					25

<210> SEQ ID NO 742
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
acacttgtgc ctaaggtttc gggat					25

<210> SEQ ID NO 743
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
caggatattc ctaaggtatc tgcat					25

<210> SEQ ID NO 744
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
caggatattc ctaaggtttc tgcat					25

<210> SEQ ID NO 745
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
caggctgttc ctaaggtatc cgcat					25

<210> SEQ ID NO 746
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 746
caggacattc caaaggtgtc tgcat                                              25

<210> SEQ ID NO 747
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
caggacattc ctaaggtgtc tgcat                                              25

<210> SEQ ID NO 748
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
caggaaattc ctaaggtgtc tgcat                                              25

<210> SEQ ID NO 749
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
caggaagttc ctaaggtgtc tgcat                                              25

<210> SEQ ID NO 750
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
actgtagtgc caaaggtgtc aggat                                              25

<210> SEQ ID NO 751
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
acagtagtac caaaggtgtc tggat                                              25

<210> SEQ ID NO 752
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
```

-continued acatatatcc ccaaagtgtc tggtt                                         25

<210> SEQ ID NO 753
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
acacttgtgc ctaaggtttc gggat                                         25

<210> SEQ ID NO 754
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
cagttatgta ttttgggctg tgcccctgc                                     29

<210> SEQ ID NO 755
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
cagctgtgta ttttaggttg tgtacctgc                                     29

<210> SEQ ID NO 756
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
cagttgtgca ttataggctg tgttcccgc                                     29

<210> SEQ ID NO 757
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
caactgtgta ttataggctg tgttcctgc                                     29

<210> SEQ ID NO 758
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
cagttatgta ttataggctg tgtacctgc                                     29

<210> SEQ ID NO 759
<211> LENGTH: 29
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 759
cagctgtgta ttattggctg tgtacctgc                                          29

<210> SEQ ID NO 760
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 760
cagttgtgta ttttaggctg tgctcc                                             26

<210> SEQ ID NO 761
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 761
cagttatgta ttttgggctg tgcccc                                             26

<210> SEQ ID NO 762
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 762
cagctgtgta ttttaggttg tgtacc                                             26

<210> SEQ ID NO 763
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 763
cagttgtgca ttataggctg tgttcc                                             26

<210> SEQ ID NO 764
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 764
caactgtgta ttataggctg tgttcc                                             26

<210> SEQ ID NO 765

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
cagttatgta ttataggctg tgttcc                                              26

<210> SEQ ID NO 766
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
cagctgtgta ttattggctg tgtacc                                              26

<210> SEQ ID NO 767
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
caattatgca tggttggatg tgcccc                                              26

<210> SEQ ID NO 768
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
cagctatgta tggtgggctg tgctcc                                              26

<210> SEQ ID NO 769
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
cagttgtgtt tagttggctg taaacc                                              26

<210> SEQ ID NO 770
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
caattatgtt tggttggctg tgcacc                                              26

<210> SEQ ID NO 771
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 771
ctgtgtattt taggctgtgt acc                                          23

<210> SEQ ID NO 772
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
ttatgtattt tgggctgtgc ccc                                          23

<210> SEQ ID NO 773
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
ctgtgtattt taggttgtgt acc                                          23

<210> SEQ ID NO 774
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
ttgtgcatta taggctgtgt tcc                                          23

<210> SEQ ID NO 775
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
ctgtgtatta taggctgtgt tcc                                          23

<210> SEQ ID NO 776
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
ttatgtatta taggctgtgt tcc                                          23

<210> SEQ ID NO 777
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 777
ctgtgtatta ttggctgtgt acc                                              23

<210> SEQ ID NO 778
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
ttatgcatgg ttggatgtgc ccc                                              23

<210> SEQ ID NO 779
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
ctatgtatgg tgggctgtgc tcc                                              23

<210> SEQ ID NO 780
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
ttgtgtttag ttggctgtaa acc                                              23

<210> SEQ ID NO 781
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
ttatgtttgg ttggctgtgc acc                                              23

<210> SEQ ID NO 782
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
aaggtgtatt tgccacctgc acctgt                                           26

<210> SEQ ID NO 783
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783
aaggtgtatc tacctccaac acctgt 26

<210> SEQ ID NO 784
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
gctgttggcc atccttatta ctctgt 26

<210> SEQ ID NO 785
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
aaggtttatc tgcctcctac ccctgt 26

<210> SEQ ID NO 786
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
acagtatatg tgcctcctcc ccctgt 26

<210> SEQ ID NO 787
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
acagtatatg tgcctcctcc ccctgt 26

<210> SEQ ID NO 788
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
aaggtttatc tacctcctcc tcctgt 26

<210> SEQ ID NO 789
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
caggtatatg tgcctcctcc ccctgt                     26

<210> SEQ ID NO 790
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
aaggtgtatt taccaccagc acctgt                     26

<210> SEQ ID NO 791
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
aaggtgtatt tgcacctgca cctgt                      25

<210> SEQ ID NO 792
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
aaggtgtatc tacctccaac acctgt                     26

<210> SEQ ID NO 793
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
gctgttggcc atccttatta ctctgt                     26

<210> SEQ ID NO 794
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
aaggtttatc tgcctcctac ccctgt                     26

<210> SEQ ID NO 795
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795
acagtatatg tgcctcctcc ccctgt                     26

<210> SEQ ID NO 796
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
acagtatatg tgcctcctcc ccctgt                                          26

<210> SEQ ID NO 797
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
aaggtttatc tacctcctcc tcctgt                                          26

<210> SEQ ID NO 798
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
caggtatatg tgcctcctcc ccctgt                                          26

<210> SEQ ID NO 799
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
attcctaaag tatctgcatt tcaata                                          26

<210> SEQ ID NO 800
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
attcccaaag ttagtgcata tcaata                                          26

<210> SEQ ID NO 801
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
gaacgtttgg tatccgcctg tcaata                                          26

```
<210> SEQ ID NO 802
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
atccctaagg tgtctgcatt tcagta                                              26

<210> SEQ ID NO 803
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
gtgccaaagg tgtcaggata tcaata                                              26

<210> SEQ ID NO 804
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
gtaccaaagg tgtctggata tcaata                                              26

<210> SEQ ID NO 805
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
atccccaaag tgtctggttt acagta                                              26

<210> SEQ ID NO 806
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
gtgcctaagg tttcgggatt tcaata                                              26

<210> SEQ ID NO 807
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
attcccaaag tatgtgcatt tcaata                                              26

<210> SEQ ID NO 808
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
attcctaaag tatctgcatt tcaata                                              26

<210> SEQ ID NO 809
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
attcccaaag ttagtgcata tcaata                                              26

<210> SEQ ID NO 810
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
gaacgtttgg tatccgcctg tcaata                                              26

<210> SEQ ID NO 811
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
atccctaagg tgtctgcatt tcagta                                              26

<210> SEQ ID NO 812
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
gtgccaaagg tgtcaggata tcaata                                              26

<210> SEQ ID NO 813
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
gtaccaaagg tgtctggata tcaata                                              26

<210> SEQ ID NO 814
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 814
atccccaaag tgtctggttt acagta                                              26

<210> SEQ ID NO 815
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
gtgcctaagg tttcgggatt tcaata                                              26

<210> SEQ ID NO 816
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
ttccctattt ttttgcagat ggc                                                 23

<210> SEQ ID NO 817
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 817
ntcccnattn ttntgcagat ggc                                                 23

<210> SEQ ID NO 818
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
```

<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 818
ntcccnattn ttntgcagat ggc        23

<210> SEQ ID NO 819
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 819
ntcccnattn ttntgcagat ggc        23

<210> SEQ ID NO 820
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 820
ntcccnattn ttnttcagat ggc        23

<210> SEQ ID NO 821
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 821
ntcccnattn ttntgcagat ggc                                             23

<210> SEQ ID NO 822
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 822
ntcccnattn ttntacagat ggc                                             23

<210> SEQ ID NO 823
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 823
ntcccnattn ttntacagat ggc                                             23

<210> SEQ ID NO 824
<211> LENGTH: 23
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 824
nacccnattn ttntacagat ggc                                              23

<210> SEQ ID NO 825
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 825
ntcccnattn ttntgcagat ggc                                              23

<210> SEQ ID NO 826
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine
```

-continued

```
<400> SEQUENCE: 826
ntcccnattn tcntgcagat ggc                                              23

<210> SEQ ID NO 827
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 827
ntcccntatn ttnttcagat gtg                                              23

<210> SEQ ID NO 828
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 828
ntcccntatn ttntacagat gtg                                              23

<210> SEQ ID NO 829
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
```

```
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 829
naccanattn ttntgcagat gtg                                              23

<210> SEQ ID NO 830
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: inosine
<220> FEATURE:
<221> NAME/KEY: modified_base
<222> LOCATION: (6)..(6)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine

<400> SEQUENCE: 830
nttccntgtn ttntgcagat gtg                                              23

<210> SEQ ID NO 831
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
gtcccgattg ttgtacagat ggc                                              23

<210> SEQ ID NO 832
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
gtcccgattg ttgtacagat ggc                                              23

<210> SEQ ID NO 833
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
ttccctattt ttttacagat ggc                                              23
```

-continued

```
<210> SEQ ID NO 834
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
ttccctattt ttttacagat ggc                                              23

<210> SEQ ID NO 835
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835
ttccctattt tttttcagat ggc                                              23

<210> SEQ ID NO 836
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
ttccttattt ttttacagat ggc                                              23

<210> SEQ ID NO 837
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 837
ttccctattt ttttacagat ggc                                              23

<210> SEQ ID NO 838
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
ttccctattt ttttacagat ggc                                              23

<210> SEQ ID NO 839
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
taccctattt ttttacagat ggc                                              23

<210> SEQ ID NO 840
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
ttccctattt ttttacagat ggc                                              23

<210> SEQ ID NO 841
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
ttccctattt tcttacagat ggc                                              23

<210> SEQ ID NO 842
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
ttcccttatt tttttcagat gtg                                              23

<210> SEQ ID NO 843
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
ttcccttatt ttttacagat gtg                                              23

<210> SEQ ID NO 844
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
taccatattt ttttgcagat gtc                                              23

<210> SEQ ID NO 845
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
tttccttgtt ttttgcagat gtg                                              23

<210> SEQ ID NO 846
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 846
tcatcctcct cctctgagct gt                                              22

<210> SEQ ID NO 847
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
tcatcctcct cctctgagct gtc                                             23

<210> SEQ ID NO 848
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
gttatctgat ttatcaataa ggtg                                            24
```

The invention claimed is:

1. A process for detecting the presence of HPV types 16, 18, 31, 33, 35, 39, 45, 51, 52, 56, 58, 59 or 68 in a sample, said process comprising the steps of:
   A) providing:
   (i) said sample suspected of containing any of said HPV types;
   (ii) a set of nucleic acid constructs comprising:
   a) at least one (1) first nucleic acid construct comprising a nucleic acid sequence, wherein the lowest number of matches of said sequence with a homologous sequence in HPV 16, 33, 52 or 58 is equal to an integer (n), and the highest number of matches with a homologous sequence in HPV 6 or HPV 11 is equal to or less than an integer (n−1);
   b) at least one (1) second nucleic acid construct comprising a sequence, wherein the lowest number of matches of said sequence with a homologous sequence in HPV 31 or 35 is equal to an integer (p), and the highest number of matches with a homologous sequence in HPV 6 or HPV 11 is equal to or less than an integer (p−1);
   c) at least one (1) third nucleic acid construct comprising a sequence, wherein the lowest number of matches of said sequence with a homologous sequence in HPV 18, 45 or 59 is equal to an integer (q), and the highest number of matches with a homologous sequence in HPV 6 or HPV 11 is equal to or less than an integer (q−1);
   d) at least one (1) fourth nucleic acid construct comprising a sequence, wherein the lowest number of matches of said sequence with a homologous sequence in HPV 39 or 68 is equal to an integer (s), and the highest number of matches with a homologous sequence in HPV 6 or HPV 11 is equal to or less than an integer (s−1); and
   e) at least one (1) fifth nucleic acid construct comprising a sequence, wherein the lowest number of matches of said sequence with a homologous sequence in HPV 51 or 56 is equal to an integer (t), and the highest number of matches with a homologous sequence in HPV 6 or HPV 11 is equal to or less than an integer (t−1);
   B) contacting said set of nucleic acid constructs (ii) with said sample (i) under conditions suitable for hybridization of said constructs (ii) to complementary sequences of HPV 16, 18, 31, 33, 35, 39, 45, 51, 52, 56, 58, 59 or 68 nucleic acids, if present in said sample; and
   C) detecting said hybridization.

2. The process of claim 1 wherein said set of constructs (ii) comprise ribonucleotides and wherein said detecting step C) is carried out by detecting the presence of RNA/DNA hybrids.

3. The process of claim 1, wherein said nucleic acid constructs are labeled.

4. The process of claim 1, wherein nucleic acids in said sample (i) have been subjected to a nucleic acid amplification procedure.

5. The process of claim 1, wherein nucleic acids in said sample have not been amplified.

6. The process of claim 1 wherein said contacting step B) is carried out in situ.

7. The process of claim 1, wherein nucleic acids in said sample have been isolated or purified.

8. The process of claim 1, wherein said contacting step B) and said detecting step C) take place during an amplification procedure.

9. The process of claim 3, wherein said label comprises biotin, iminobiotin, an electron dense component, a magnetic component, a hormone component, a metal-containing component, a fluorescent component, a chromogenic component, a chemiluminescent component, an antigen, a hapten, an antibody component or a chelating component, a radioisotope, a phosphorescent component, an intercalating component, an energy transfer component, or any combination of the above.

10. The process of claim 4 wherein said amplification procedure has been carried out using at least two set of primers wherein at least one primer of a first set binds to one strand of an HPV nucleic acid and at least one primer of a second set binds to the complementary strand of said HPV nucleic acid.

11. The process of claim 8 wherein said amplification procedure is carried out using at least two set of primers wherein at least one primer of a first set of primers binds to one strand of an HPV nucleic acid and at least one primer of a second set of primers binds to the complementary strand of said HPV nucleic acid.

12. The process of claim 10 or 11 wherein said first set of primers comprises one or more consensus primers and said second set of primers comprises one or more consensus primers, wherein said consensus primers are capable of binding to HPV 16, 18, 31, 33, 35, 39, 45, 51, 52, 56, 58, 59 or 68.

13. The process of claim 10 or 11, wherein said first set of primers comprise one or more consensus primers wherein said consensus primers are capable of binding to HPV 16, 18, 31, 33, 35, 39, 45, 51, 52, 56, 58, 59 or 68 and wherein said second set of primers comprise:
   a) at least one (1) first nucleic acid construct comprising a nucleic acid sequence, wherein the lowest number of matches of said sequence with a homologous sequence in HPV 16, 33, 52 or 58 is equal to an integer (N), and the highest number of matches with a homologous sequence in HPV 6 or HPV 11 is equal to or less than an integer (N–1);
   b) at least one (1) second nucleic acid construct comprising a sequence, wherein the lowest number of matches of said sequence with a homologous sequence in HPV 31 or 35 is equal to an integer (P), and the highest number of matches with a homologous sequence in HPV 6 or HPV 11 is equal to or less than an integer (P–1);
   c) at least one (1) third nucleic acid construct comprising a sequence, wherein the lowest number of matches of said sequence with a homologous sequence in HPV 18, 45 or 59 is equal to an integer (Q), and the highest number of matches with a homologous sequence in HPV 6 or HPV 11 is equal to or less than an integer (Q–1);
   d) at least one (1) fourth nucleic acid construct comprising a sequence, wherein the lowest number of matches of said sequence with a homologous sequence in HPV 39 or 68 is equal to an integer (S), and the highest number of matches with a homologous sequence in HPV 6 or HPV 11 is equal to or less than an integer (S–1); and
   e) at least one (1) fifth nucleic acid construct comprising a sequence, wherein the lowest number of matches of said sequence with a homologous sequence in HPV 51 or 56 is equal to an integer (T), and the highest number of matches with a homologous sequence in HPV 6 or HPV 11 is equal to or less than an integer (T–1).

14. The process of claim 10 or 11, wherein said first set of primers comprise:
   a) at least one (1) first nucleic acid construct comprising a nucleic acid sequence, wherein the lowest number of matches of said sequence with a homologous sequence in HPV 16, 33, 52 or 58 is equal to an integer ($N_F$), and the highest number of matches with a homologous sequence in HPV 6 or HPV 11 is equal to or less than an integer ($N_F$–1);
   b) at least one (1) second nucleic acid construct comprising a sequence, wherein the lowest number of matches of said sequence with a homologous sequence in HPV 31 or 35 is equal to an integer ($P_F$), and the highest number of matches with a homologous sequence in HPV 6 or HPV 11 is equal to or less than an integer ($P_F$–1);
   c) at least one (1) third nucleic acid construct comprising a sequence, wherein the lowest number of matches of said sequence with a homologous sequence in HPV 18, 45 or 59 is equal to an integer ($Q_F$), and the highest number of matches with a homologous sequence in HPV 6 or HPV 11 is equal to or less than an integer ($Q_F$–1);
   d) at least one (1) fourth nucleic acid construct comprising a sequence, wherein the lowest number of matches of said sequence with a homologous sequence in HPV 39 or 68 is equal to an integer ($S_F$), and the highest number of matches with homologous sequence in HPV 6 or HPV 11 is equal to or less than an integer ($S_F$–1); and
   e) at least one (1) fifth nucleic acid construct comprising a sequence, wherein the lowest number of matches of said sequence with a homologous sequence in HPV 51 or 56 is equal to an integer ($T_F$), and the highest number of matches with a homologous sequence in HPV 6 or HPV 11 is equal to or less than an integer ($T_F$–1)
and said second set of primers comprise:
   a) at least one (1) first nucleic acid construct comprising a nucleic acid sequence, wherein the lowest number of matches of said sequence with a homologous sequence in HPV 16, 33, 52 or 58 is equal to an integer ($N_R$), and the highest number of matches with a homologous sequence in HPV 6 or HPV 11 is equal to or less than an integer ($N_R$1);
   b) at least one (1) second nucleic acid construct comprising a sequence, wherein the lowest number of matches of said sequence with a homologous sequence in HPV 31 or 35 is equal to an integer ($P_R$), and the highest number of matches with a homologous sequence in HPV 6 or HPV 11 is equal to or less than an integer ($P_R$–1);
   c) at least one (1) third nucleic acid construct comprising a sequence, wherein the lowest number of matches of said sequence with a homologous sequence in HPV 18, 45 or 59 is equal to an integer ($Q_R$), and the highest number of matches with a homologous sequence in HPV 6 or HPV 11 is equal to or less than an integer ($Q_R$–1);
   d) at least one (1) fourth nucleic acid construct comprising a sequence, wherein the lowest number of matches of said sequence with a homologous sequence in HPV 39 or 68 is equal to an integer ($S_R$), and the highest number of matches with a homologous sequence in HPV 6 or HPV 11 is equal to or less than an integer ($S_R$–1); and
   e) at least one (1) fifth nucleic acid construct comprising a sequence, wherein the lowest number of matches of said sequence with a homologous sequence in HPV 51 or 56 is equal to an integer ($T_R$), and the highest number of matches with a homologous sequence in HPV 6 or HPV 11 is equal to or less than an integer ($T_R$–1).

15. The process of claim 1, wherein a set of suppressor nucleic acid constructs are also provided wherein said suppressor nucleic acid constructs comprise
   a) at least one (1) first suppressor nucleic acid construct comprising a sequence, wherein the lowest number of matches of said sequence with a homologous sequence in HPV 6 or HPV 11 is equal to an integer (g), and the highest number of matches of said sequence with a homologous sequence in HPV 16, 33, 52 or 58 is equal to or less than an integer (g–1);
   b) at least one (1) second suppressor nucleic acid construct comprising a sequence, wherein the lowest number of matches of said sequence with a homologous sequence in HPV 6 or HPV 11 is equal to an integer (h), and the highest number of matches of said sequence with a homologous sequence in HPV 31 or 35 is equal to or less than an integer (h−1);
c) at least one (1) third suppressor nucleic acid construct comprising a sequence, wherein the lowest number of matches of said sequence with a homologous sequence in HPV 6 or HPV 11 is equal to an integer (j), and the highest number of matches of said sequence with a homologous sequence in HPV 18, 45 or 59 is equal to or less than an integer (j−1);
d) at least one (1) fourth suppressor nucleic acid construct comprising a sequence, wherein the lowest number of matches of said sequence with a homologous sequence in HPV 6 or HPV 11 is equal to an integer (k), and the highest number of matches of said sequence with a homologous sequence in HPV 39 or 68 is equal to or less than an integer (k−1); and
e) at least one (1) fifth suppressor nucleic acid construct comprising a sequence, wherein the lowest number of matches of said sequence with the homologous sequence in HPV 6 or HPV 11 is equal to an integer (m) and the highest number of matches of said sequence with a homologous sequence in HPV 51 or 56 is equal to or less than an integer (m−1); and wherein said suppressor nucleic acid constructs comprise sequences that are homologous to all or a portion of one or more of the sequences of the nucleic acid constructs (ii).

16. The process of claim 10 or 11, wherein a set of suppressor nucleic acid constructs are also present during said amplification, wherein said suppressor nucleic acid constructs comprise:
a) at least one (1) first suppressor nucleic acid construct comprising a sequence, wherein the lowest number of matches of said sequence with a homologous sequence in HPV 6 or HPV 11 is equal to an integer (g), and the highest number of matches of said sequence with a homologous sequence in HPV 16, 33, 52 or 58 is equal to or less than an integer (g−1);
b) at least one (1) second suppressor nucleic acid construct comprising a sequence, wherein the lowest number of matches of said sequence with a homologous sequence in HPV 6 or HPV 11 is equal to an integer (h), and the highest number of matches of said sequence with a homologous sequence in HPV 31 or 35 is equal to or less than an integer (h−1);
c) at least one (1) third suppressor nucleic acid construct comprising a sequence, wherein the lowest number of matches of said sequence with a homologous sequence in HPV 6 or HPV 11 is equal to an integer (j), and the highest number of matches of said sequence with a homologous sequence in HPV 18, 45 or 59 is equal to or less than an integer (j−1);
d) at least one (1) fourth suppressor nucleic acid construct comprising a sequence, wherein the lowest number of matches of said sequence with a homologous sequence in HPV 6 or HPV 11 is equal to an integer (k), and the highest number of matches of said sequence with a homologous sequence in HPV 39 or 68 is equal to or less than an integer (k−1); and
e) at least one (1) fifth suppressor nucleic acid construct comprising a sequence, wherein the lowest number of matches of said sequence with the homologous sequence in HPV 6 or HPV 11 is equal to an integer (m) and the highest number of matches of said sequence with a homologous sequence in HPV 51 or 56 is equal to or less than an integer (m−1); and wherein said suppressor nucleic acid constructs comprise sequences that are homologous to all or a portion of one or more said primers.

17. The process of claim 4 or 7 wherein said amplification procedure comprises the polymerase chain reaction, the ligase chain reaction, the GAP-LCR method, the 3SR reaction, the NASBA reaction, the Transcription Mediated Amplification reaction, the Strand Displacement Amplification reaction, or the isothermal hairpin amplification reaction.

18. A process for detecting the presence of HPV 16, 18, 31, 33, 35, 39, 45, 51, 52, 56, 58, 59 or 68 in a sample, said process comprising the steps of:
A) providing:
i) said sample suspected of containing any of said HPV types;
ii) a first set of nucleic acid constructs comprising:
a) at least one (1) first nucleic acid construct comprising a nucleic acid sequence, wherein the lowest number of matches of said sequence with a homologous sequence in HPV 16, 33, 52 or 58 is equal to an integer (n), and the highest number of matches with a homologous sequence in HPV 6 or HPV 11 is equal to or less than an integer (n−1);
b) at least one (1) second nucleic acid construct comprising a sequence, wherein the lowest number of matches of said sequence with a homologous sequence in HPV 31 or 35 is equal to an integer (p), and the highest number of matches with a homologous sequence in HPV 6 or HPV 11 is equal to or less than an integer (p−1);
c) at least one (1) third nucleic acid construct comprising a sequence, wherein the lowest number of matches of said sequence with a homologous sequence in HPV 18, 45 or 59 is equal to an integer (q), and the highest number of matches with a homologous sequence in HPV 6 or HPV 11 is equal to or less than an integer (q−1);
d) at least one (1) fourth nucleic acid construct comprising a sequence, wherein the lowest number of matches of said sequence with a homologous sequence in HPV 39 or 68 is equal to an integer (s), and the highest number of matches with a homologous sequence in HPV 6 or HPV 11 is equal to or less than an integer (s−1); and
e) at least one (1) fifth nucleic acid construct comprising a sequence, wherein the lowest number of matches of said sequence with a homologous sequence in HPV 51 or 56 is equal to an integer (t), and the highest number of matches with a homologous sequence in HPV 6 or HPV 11 is equal to or less than an integer (t−1);
iii) a second set of nucleic acid constructs comprising:
a) at least one (1) first suppressor nucleic acid construct comprising a sequence, wherein the lowest number of matches of said sequence with a homologous sequence in HPV 6 or HPV 11 is equal to an integer (g), and the highest number of matches of said sequence with a homologous sequence in HPV 16, 33, 52 or 58 is equal to or less than an integer (g−1);
b) at least one (1) second suppressor nucleic acid construct comprising a sequence, wherein the lowest number of matches of said sequence with a homologous sequence in HPV 6 or HPV 11 is equal to an integer (h), and the highest number of matches of said sequence with a homologous sequence in HPV 31 or 35 is equal to or less than an integer (h−1);

c) at least one (1) third suppressor nucleic acid construct comprising a sequence, wherein the lowest number of matches of said sequence with a homologous sequence in HPV 6 or HPV 11 is equal to an integer (j), and the highest number of matches of said sequence with a homologous sequence in HPV 18, 45 or 59 is equal to or less than an integer (j−1);

d) at least one (1) fourth suppressor nucleic acid construct comprising a sequence, wherein the lowest number of matches of said sequence with a homologous sequence in HPV 6 or HPV 11 is equal to an integer (k), and the highest number of matches of said sequence with a homologous sequence in HPV 39 or 68 is equal to or less than an integer (k−1); and e) at least one (1) fifth suppressor nucleic acid construct comprising a sequence, wherein the lowest number of matches of said sequence with the homologous sequence in HPV 6 or HPV 11 is equal to an integer (m) and the highest number of matches of said sequence with a homologous sequence in HPV 51 or 56 is equal to or less than an integer (m−1); and wherein said suppressor nucleic acid constructs comprise sequences that are homologous to all or a portion of one or more of the sequences of the nucleic acid constructs (ii);

B) contacting said sets of nucleic acid constructs (ii) and (iii) with said sample (i) under conditions suitable for hybridization of said constructs (ii) to complementary sequences of HPV 16, 18, 31, 33, 35, 39, 45, 51, 52, 56, 58, 59 or 68, if present in said sample; and C) detecting said hybridization.

19. The process of claim 18 wherein said first set of constructs (ii) comprise ribonucleotides and said second set of constructs (iii) lack ribonucleotides and wherein said detecting step C) is carried out by detecting the presence of RNA/DNA hybrids.

20. The process of claim 18, wherein said first set of nucleic acid constructs (ii) are labeled.

21. The process of claim 18, wherein said nucleic acids in said sample (i) have been subjected to a nucleic acid amplification procedure.

22. The process of claim 18, wherein nucleic acids in said sample (i) have not been amplified.

23. The process of claim 18, wherein said contacting step B) is carried out in situ.

24. The process of claim 18, wherein nucleic acids in said sample (i) have been isolated or purified.

25. The process of claim 18, wherein said contacting step B) and said detecting step C) are carried out during an amplification procedure.

26. The process of claim 20, wherein said label is selected from biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

27. The process of claim 21 wherein said amplification procedure has been carried out using at least two set of primers wherein at least one primer of a first set of primers binds to one strand of an HPV nucleic acid and at least one strand of a second set of primers binds to the complementary strand of said HPV nucleic acid.

28. The process of claim 25 wherein said amplification procedure is carried out using at least two set of primers wherein at least one primer of a first set of primers binds to one strand of an HPV nucleic acid and at least one primer of a second set of primers binds to the complementary strand of said HPV nucleic acid.

29. The process of claim 27 or 28 wherein said first set of primers comprises one or more consensus primers and said second set of primers comprises one or more consensus primers, wherein said consensus primers are capable of binding to HPV 16, 18, 31, 33, 35, 39, 45, 51, 52, 56, 58, 59 or 68.

30. The process of claim 27 or 28, wherein said first set of primers comprise one or more consensus primers wherein said consensus primers are capable of binding to HPV 16, 18, 31, 33, 35, 39, 45, 51, 52, 56, 58, 59 or 68 and wherein said second set of primers comprise:

a) at least one (1) first nucleic acid construct comprising a nucleic acid sequence, wherein the lowest number of matches of said sequence with a homologous sequence in HPV 16, 33, 52 or 58 is equal to an integer (N), and the highest number of matches with a homologous sequence in HPV 6 or HPV 11 is equal to or less than an integer (N−1);

b) at least one (1) second nucleic acid construct comprising a sequence, wherein the lowest number of matches of said sequence with a homologous sequence in HPV 31 or 35 is equal to an integer (P), and the highest number of matches with a homologous sequence in HPV 6 or HPV 11 is equal to or less than an integer (P−1);

c) at least one (1) third nucleic acid construct comprising a sequence, wherein the lowest number of matches of said sequence with a homologous sequence in HPV 18, 45 or 59 is equal to an integer (Q), and the highest number of matches with a homologous sequence in HPV 6 or HPV 11 is equal to or less than an integer (Q−1);

d) at least one (1) fourth nucleic acid construct comprising a sequence, wherein the lowest number of matches of said sequence with a homologous sequence in HPV 39 or 68 is equal to an integer (S), and the highest number of matches with a homologous sequence in HPV 6 or HPV 11 is equal to or less than an integer (S−1); and e) at least one (1) fifth nucleic acid construct comprising a sequence, wherein the lowest number of matches of said sequence with a homologous sequence in HPV 51 or 56 is equal to an integer (T), and the highest number of matches with a homologous sequence in HPV 6 or HPV 11 is equal to or less than an integer (T−1).

31. The process of claim 27 or 28, wherein said first set of primers comprise:

a) at least one (1) first nucleic acid construct comprising a nucleic acid sequence, wherein the lowest number of matches of said sequence with a homologous sequence in HPV 16, 33, 52 or 58 is equal to an integer ($N_F$), and the highest number of matches with a homologous sequence in HPV 6 or HPV 11 is equal to or less than an integer ($N_F$−1);

b) at least one (1) second nucleic acid construct comprising a sequence, wherein the lowest number of matches of said sequence with a homologous sequence in HPV 31 or 35 is equal to an integer ($P_F$), and the highest number of matches with a homologous sequence in HPV 6 or HPV 11 is equal to or less than an integer ($P_F$−1);

c) at least one (1) third nucleic acid construct comprising a sequence, wherein the lowest number of matches of said sequence with a homologous sequence in HPV 18, 45 or 59 is equal to an integer ($Q_F$), and the highest number of matches with a homologous sequence in HPV 6 or HPV 11 is equal to or less than an integer ($Q_F-1$);

d) at least one (1) fourth nucleic acid construct comprising a sequence, wherein the lowest number of matches of said sequence with a homologous sequence in HPV 39 or 68 is equal to an integer ($S_F$), and the highest number of matches with a homologous sequence in HPV 6 or HPV 11 is equal to or less than an integer ($S_F-1$); and e) at least one (1) fifth nucleic acid construct comprising a sequence, wherein the lowest number of matches of said sequence with a homologous sequence in HPV 51 or 56 is equal to an integer ($T_F$), and the highest number of matches with a homologous sequence in HPV 6 or HPV 11 is equal to or less than an integer ($T_F-1$) and said second set of primers comprise:

a) at least one (1) first nucleic acid construct comprising a nucleic acid sequence, wherein the lowest number of matches of said sequence with a homologous sequence in HPV 16, 33, 52 or 58 is equal to an integer ($N_R$), and the highest number of matches with a homologous sequence in HPV 6 or HPV 11 is equal to or less than an integer ($N_R1$);

b) at least one (1) second nucleic acid construct comprising a sequence, wherein the lowest number of matches of said sequence with a homologous sequence in HPV 31 or 35 is equal to an integer ($P_R$), and the highest number of matches with a homologous sequence in HPV 6 or HPV 11 is equal to or less than an integer ($P_R-1$);

c) at least one (1) third nucleic acid construct comprising a sequence, wherein the lowest number of matches of said sequence with a homologous sequence in HPV 18, 45 or 59 is equal to an integer ($Q_R$), and the highest number of matches with a homologous sequence in HPV 6 or HPV 11 is equal to or less than an integer ($Q_R-1$);

d) at least one (1) fourth nucleic acid construct comprising a sequence, wherein the lowest number of matches of said sequence with a homologous sequence in HPV 39 or 68 is equal to an integer ($S_R$), and the highest number of matches with a homologous sequence in HPV 6 or HPV 11 is equal to or less than an integer ($S_R-1$); and e) at least one (1) fifth nucleic acid construct comprising a sequence, wherein the lowest number of matches of said sequence with a homologous sequence in HPV 51 or 56 is equal to an integer ($T_R$), and the highest number of matches with a homologous sequence in HPV 6 or HPV 11 is equal to or less than an integer ($T_R-1$).

32. The process of claim 21 or 25 wherein said amplification procedure comprises the polymerase chain reaction, the ligase chain reaction, the GAP-LCR method, the 3SR reaction, the NASBA reaction, the Transcription Mediated Amplification reaction, the Strand Displacement Amplification reaction, or the isothermal hairpin amplification reaction.

33. A method of detecting the presence of HPV 16, 18, 31, 33, 35, 39, 45, 51, 52, 56, 58, 59 or 68 in a sample comprising the steps of:

A) providing:
  i) a sample;
  ii) a first set of nucleic acid constructs comprising sequences complementary to sequences of a strand of HPV nucleic acid wherein said set comprises:
    a) at least one (1) first nucleic acid construct comprising a nucleic acid sequence, wherein the lowest number of matches of said sequence with a homologous sequence in HPV 16, 33, 52 or 58 is equal to an integer (n), and the highest number of matches with a homologous sequence in HPV 6 or HPV 11 is equal to or less than an integer (n−1);
    b) at least one (1) second nucleic acid construct comprising a sequence, wherein the lowest number of matches of said sequence with a homologous sequence in HPV 31 or 35 is equal to an integer (p), and the highest number of matches with a homologous sequence in HPV 6 or HPV 11 is equal to or less than an integer (p−1);
    c) at least one (1) third nucleic acid construct comprising a sequence, wherein the lowest number of matches of said sequence with a homologous sequence in HPV 18, 45 or 59 is equal to an integer (q), and the highest number of matches with a homologous sequence in HPV 6 or HPV 11 is equal to or less than an integer (q−1);
    d) at least one (1) fourth nucleic acid construct comprising a sequence, wherein the lowest number of matches of said sequence with a homologous sequence in HPV 39 or 68 is equal to an integer (s), and the highest number of matches with a homologous sequence in HPV 6 or HPV 11 is equal to or less than an integer, (s−1); and
    e) at least one (1) fifth nucleic acid construct comprising a sequence, wherein the lowest number of matches of said sequence with a homologous sequence in HPV 51 or 56 is equal to an integer (t), and the highest number of matches with a homologous sequence in HPV 6 or HPV 11 is equal to or less than an integer (t−1);
  iii) a second set of nucleic acid constructs comprising sequences substantially identical to sequences of said strand of HPV nucleic acid; and
  iv) reagents appropriate for carrying out extension of said nucleic acid constructs;

B) contacting said first set of nucleic acid constructs with said sample under conditions suitable for hybridization of said nucleic acid constructs to complementary sequences of HPV 16, 18, 31, 33, 35, 39, 45, 51, 52, 56, 58, 59 or 68 if present in the sample;

C) extending one or more of said first set of nucleic acid constructs using the sequences of HPV 16, 18, 31, 33, 35, 39, 45, 51, 52, 56, 58, 59 or 68 as templates;

D) contacting said second set of nucleic acid constructs with said extended first nucleic acid constructs from step (D);

E) extending one or more of said second set of nucleic acid constructs using the extended nucleic acid construct from step (E) as templates;

F) repeating one or more of the preceding steps; and

G) detecting extension products synthesized by using HPV 16, 18, 31, 33, 35, 39, 45, 51, 52, 56, 58, 59 or 68 as templates and thereby determining the presence of HPV 16, 18, 31, 33, 35, 39, 45, 51, 52, 56, 58, 59 or 68 in the sample.

34. The method of claim 33, wherein said second set comprises a set of nucleic acid constructs wherein:

a) at least one (1) first nucleic acid construct comprising a nucleic acid sequence, wherein the lowest number of matches of said sequence with a homologous sequence in HPV 16, 33, 52 or 58 is equal to an integer (N), and the highest number of matches with a homologous sequence in HPV 6 or HPV 11 is equal to or less than an integer (N−1);

b) at least one (1) second nucleic acid construct comprising a sequence, wherein the lowest number of matches of said sequence with a homologous sequence in HPV 31 or 35 is equal to an integer (P), and the highest number of matches with a homologous sequence in HPV 6 or HPV 11 is equal to or less than an integer (P−1);

c) at least one (1) third nucleic acid construct comprising a sequence, wherein the lowest number of matches of said sequence with a homologous sequence in HPV 18, 45 or 59 is equal to an integer (Q), and the highest number of matches with a homologous sequence in HPV 6 or HPV 11 is equal to or less than an integer (Q−1);

d) at least one (1) fourth nucleic acid construct comprising a sequence, wherein the lowest number of matches of said sequence with a homologous sequence in HPV 39 or 68 is equal to an integer (S), and the highest number of matches with a homologous sequence in HPV 6 or HPV 11 is equal to or less than an integer (S−1); and e) at least one (1) fifth nucleic acid construct comprising a sequence, wherein the lowest number of matches of said sequence with a homologous sequence in HPV 51 or 56 is equal to an integer (T), and the highest number of matches with a homologous sequence in HPV 6 or HPV 11 is equal to or less than an integer (T−1).

35. The method of claim 33 wherein said second set comprises HPV consensus primers.

36. The method of claim 33, 34 or 35 wherein said extension step (C) is carried out by a DNA polymerase.

37. The method of claim 36 wherein said DNA polymerase is selected from one or more of the group comprising Taq DNA polymerase, Klenow Fragment, DNA polymerase I, Bst DNA polymerase, Bca DNA polymerase, Tth DNA polymerase, T4 DNA polymerase, Tfl DNA polymerase, Pfx DNA polymerase, Elongase, Herculase, Taq Plus, Deep-vent Polymerase, Vent DNA polymerase, T4 DNA polymerase, T7 DNA polymerase, Bca DNA polymerase, Thermal Ace™ polymerase, or any mutants or modified versions of the foregoing.

38. The method of claim 36 wherein said DNA polymerase is a Reverse Transcriptase.

39. The method of claim 38 wherein said Reverse Transcriptase comprises HIV-1 reverse transcriptase, HIV-2 reverse transcriptase, AMV reverse transcriptase, MMLV reverse transcriptase, RSV reverse transcriptase, ALV reverse transcriptase, MuLV reverse transcriptase, Sensiscript, SuperScript™, Thermo Script™ or Omniscript.

40. The method of claim 39 wherein said Reverse Transcriptase has been modified such that it is RnaseH⁻.

41. The method of claim 33 or 34, wherein said extension step (C) is carried out by ligase.

42. The method of claim 41, wherein said ligase comprises T4 DNA ligase, T4 RNA ligase, *Pyrococcus furiosus* DNA ligase, *Escherichia coli* DNA ligase, Taq DNA ligase, recombinant Human ligase I, recombinant Human ligase II, recombinant Human ligase III or recombinant Human ligase IV.

43. The method of claim 33, 34 or 35 wherein said second set is used for extension prior to said first set.

44. The method of claim 33, 34 or 35 wherein one or more of said nucleic acid constructs comprise sequences for RNA promoters.

45. The method of claim 44 wherein said process comprises a further step of transcription from said RNA promoters.

46. The method of claim 44 wherein said RNA promoters comprise T3, T7 or SP6.

47. The method of claim 33, wherein said reagents (iv) comprise one or more modified nucleotides or nucleotide analogues.

48. The method of claim 47, wherein said modified nucleotides are labeled or unlabeled.

49. The method of claim 47, wherein said nucleotide analogues are labeled or unlabeled.

50. The method of claim 48 or 49, wherein said labeled modified nucleotides or labeled nucleotide analogues comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

51. The method of claim 50, wherein said detections step (G) is carried out by the detection of the presence of extension products labeled by incorporation of said labeled modified nucleotides or labeled nucleotide analogues.

52. The method of claim 33 or 34, wherein said detection step (G) is carried out by hybridization with one or more labeled probes.

53. The method of claim 52, wherein said one or more labeled probes comprise labeled nucleotides or labeled nucleotide analogues.

54. The method of claim 53, wherein said labeled nucleotides or labeled nucleotide analogues comprise biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

55. The method of claim 52, wherein said labeled probe comprises sequences from HPV 16, 18, 31, 33, 35, 39, 45, 51, 52, 56, 58, 59, 68 or any combination thereof.

56. The method of claim 52, wherein said labeled probe comprises a set of probes wherein:

a) at least one (1) first labeled probe comprises a nucleic acid sequence, wherein the lowest number of matches of said sequence with a homologous sequence in HPV 16, 33, 52 or 58 is equal to an integer (PRn), and the highest number of matches with a homologous sequence in HPV 6 or HPV 11 is equal to or less than an integer (PRn−1);

b) at least one (1) second labeled probe comprises a sequence, wherein the lowest number of matches of said sequence with a homologous sequence in HPV 31 or 35 is equal to an integer (PRp), and the highest number of matches with a homologous sequence in HPV 6 or HPV 11 is equal to or less than an integer (PRp−1);

c) at least one (1) third labeled probe comprises a sequence, wherein the lowest number of matches of said sequence with a homologous sequence in HPV 18, 45 or 59 is equal to an integer (PRq), and the highest number of matches with a homologous sequence in HPV 6 or HPV 11 is equal to or less than an integer (PRq−1);

d) at least one (1) fourth labeled probe comprises a sequence, wherein the lowest number of matches of said sequence with a homologous sequence in HPV 39 or 68 is equal to an integer (PRs), and the highest number of matches with a homologous sequence in HPV 6 or HPV 11 is equal to or less than an integer (PRs−1); and e) at least one (1) fifth labeled probe comprises a sequence, wherein the lowest number of matches of said sequence with a homologous sequence in HPV 51 or 56 is equal to an integer (PRt), and the highest number of matches with a homologous sequence in HPV 6 or HPV 11 is equal to or less than an integer (PRt−1).

57. The method of claim 56 wherein at least one of said first labeled probe, said second labeled probe, said third nucleic acid probe, said fourth labeled probe and said fifth labeled probe comprises the same sequence.

58. The method of claim 33, 34 or 35, wherein said detection step (G) is carried out by the presence of an intercalating agent that indicates the synthesis of extension products.

59. The method of claim 33, 34 or 35, wherein said method comprises the polymerase chain reaction, the ligase chain reaction, the GAP-LCR method, the 3SR reaction, the NASBA reaction, the Transcription Mediated Amplification reaction, the Strand Displacement Amplification reaction, or the isothermal hairpin amplification reaction.

60. A method of detecting the presence of HPV 16, 18, 31, 33, 35, 39, 45, 51, 52, 56, 58, 59 or 68 in a sample comprising the steps of:
  A) providing:
    i) a sample;
    ii) a first set of nucleic acid constructs comprising sequences complementary to sequences of a strand of HPV nucleic acid wherein said set comprises:
      a) at least one (1) first nucleic acid construct comprising a nucleic acid sequence, wherein the lowest number of matches of said sequence with a homologous sequence in HPV 16, 33, 52 or 58 is equal to an integer (n), and the highest number of matches with a homologous sequence in HPV 6 or HPV 11 is equal to or less than an integer (n−1);
      b) at least one (1) second nucleic acid construct comprising a sequence, wherein the lowest number of matches of said sequence with a homologous sequence in HPV 31 or 35 is equal to an integer (p), and the highest number of matches with a homologous sequence in HPV 6 or HPV 11 is equal to or less than an integer (p−1);
      c) at least one (1) third nucleic acid construct comprising a sequence, wherein the lowest number of matches of said sequence with a homologous sequence in HPV 18, 45 or 59 is equal to an integer (q), and the highest number of matches with a homologous sequence in HPV 6 or HPV 11 is equal to or less than an integer (q−1);
      d) at least one (1) fourth nucleic acid construct comprising a sequence, wherein the lowest number of matches of said sequence with a homologous sequence in HPV 39 or 68 is equal to an integer (s), and the highest number of matches with a homologous sequence in HPV 6 or HPV 11 is equal to or less than an integer (s−1); and
      e) at least one (1) fifth nucleic acid construct comprising a sequence, wherein the lowest number of matches of said sequence with a homologous sequence in HPV 51 or 56 is equal to an integer (t), and the highest number of matches with a homologous sequence in HPV 6 or HPV 11 is equal to or less than an integer (t−1);
    iii) a second set of nucleic acid constructs comprising sequences substantially identical to sequences of said strand of HPV nucleic acid wherein said second set comprises a set of nucleic acid constructs wherein:
      a) at least one (1) first nucleic acid construct comprises a nucleic acid sequence, wherein the lowest number of matches of said sequence with a homologous sequence in HPV 16, 33, 52 or 58 is equal to an integer (N), and the highest number of matches with a homologous sequence in HPV 6 or HPV 11 is equal to or less than an integer (N−1);
      b) at least one (1) second nucleic acid construct comprises a sequence, wherein the lowest number of matches of said sequence with a homologous sequence in HPV 31 or 35 is equal to an integer (P), and the highest number of matches with a homologous sequence in HPV 6 or HPV 11 is equal to or less than an integer (P−1);
      c) at least one (1) third nucleic acid construct comprises a sequence, wherein the lowest number of matches of said sequence with a homologous sequence in HPV 18, 45 or 59 is equal to an integer (Q), and the highest number of matches with a homologous sequence in HPV 6 or HPV 11 is equal to or less than an integer (Q−1);
      d) at least one (1) fourth nucleic acid construct comprises a sequence, wherein the lowest number of matches of said sequence with a homologous sequence in HPV 39 or 68 is equal to an integer (S), and the highest number of matches with a homologous sequence in HPV 6 or HPV 11 is equal to or less than an integer (S−1); and
      e) at least one (1) fifth nucleic acid construct comprises a sequence, wherein the lowest number of matches of said sequence with a homologous sequence in HPV 51 or 56 is equal to an integer (T), and the highest number of matches with a homologous sequence in HPV 6 or HPV 11 is equal to or less than an integer (T−1); and
    iv) reagents appropriate for carrying out extension of said nucleic acid constructs;
  B) contacting said first set of nucleic acid constructs with said sample under conditions suitable for hybridization of said nucleic acid constructs to complementary sequences of HPV 16, 18, 31, 33, 35, 39, 45, 51, 52, 56, 58, 59 or 68 if present in the sample;
  C) extending one or more of said first set of nucleic acid constructs using the sequences of HPV 16, 18, 31, 33, 35, 39, 45, 51, 52, 56, 58, 59 or 68 as templates;
  D) contacting said second set of nucleic acid constructs with said extended first nucleic acid constructs from step (D);
  E) extending one or more of said second set of nucleic acid constructs using the extended nucleic acid construct from step (E) as templates;
  F) repeating one or more of the preceding steps; and
  G) detecting extension products synthesized by using HPV 16, 18, 31, 33, 35, 39, 45, 51, 52, 56, 58, 59 or 68 as templates and thereby determining the presence of HPV 16, 18, 31, 33, 35, 39, 45, 51, 52, 56, 58, 59 or 68 in the sample.

61. The method of claim 60, wherein said extension step (C) is carried out by a DNA polymerase.

62. The method of claim 61 wherein said DNA polymerase comprises Taq DNA polymerase, Klenow Fragment, DNA polymerase I, Bst DNA polymerase, Bca DNA polymerase, Tth DNA polymerase, T4 DNA polymerase, Tfl DNA polymerase, Pfx DNA polymerase, Elongase, Herculase, Taq Plus, Deep-vent Polymerase, Vent DNA polymerase, T4 DNA polymerase, T7 DNA polymerase, Bca DNA polymerase, Thermal Ace™ polymerase or any mutants or modified versions of the foregoing.

63. The method of claim 61, wherein said DNA polymerase is a Reverse Transcriptase.

64. The method of claim 63, wherein said Reverse Transcriptase comprises HIV-1 reverse transcriptase, HIV-2 reverse transcriptase, AMV reverse transcriptase, MMLV reverse transcriptase, RSV reverse transcriptase, ALV reverse transcriptase, MuLV reverse transcriptase, Sensiscript, SuperScript™, Thermo Script™ or Omniscript.

65. The method of claim 63, wherein said Reverse Transcriptase has been modified such that it is RnaseH⁻.

66. The method of claim 60, wherein said extension step (C) is carried out by ligase.

67. The method of claim 66, wherein said ligase comprises T4 DNA ligase, T4 RNA ligase, *Pyrococcus furiosus* DNA ligase, *Escherichia coli* DNA ligase, Taq DNA ligase, recombinant Human ligase I, recombinant Human ligase II, recombinant Human ligase III or recombinant Human ligase IV.

68. The method of claim 60, wherein one or more of said nucleic acid constructs comprises sequences for RNA promoters.

69. The method of claim 68 wherein said method comprises a further step of transcription from said RNA promoters.

70. The method of claim 68 wherein said RNA promoters comprise T3, T7 or SP6.

71. The method of claim 60, wherein said reagents (iv) comprise one or more modified nucleotides or nucleotide analogues.

72. The method of claim 71, wherein said modified nucleotides are labeled or unlabeled.

73. The method of claim 62, wherein said nucleotide analogues are labeled or unlabeled.

74. The method of claim 63 or 64, wherein said labeled modified nucleotides or labeled nucleotide analogues comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

75. The method of claim 60, wherein said detections step (G) is carried out by the detection of the presence of extension products labeled by incorporation of said labeled modified nucleotides or labeled nucleotide analogues.

76. The method of claim 60, wherein said detection step (G) is carried out by hybridization with one or more labeled probes.

77. The method of claim 76, wherein said one or more labeled probes comprise labeled nucleotides or labeled nucleotide analogues.

78. The method of claim 77, wherein said labeled nucleotides or labeled nucleotide analogues comprise biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination of the foregoing.

79. The method of claim 76, wherein said labeled probe comprises sequences from HPV 16, 18, 31, 33, 35, 39, 45, 51, 52, 56, 58, 59, 68 or any combination thereof.

80. The method of claim 76, wherein said labeled probe comprises a set of probes wherein:
a) at least one (1) first labeled probe comprises a nucleic acid sequence, wherein the lowest number of matches of said sequence with a homologous sequence in HPV 16, 33, 52 or 58 is equal to an integer (PRn), and the highest number of matches with a homologous sequence in HPV 6 or HPV 11 is equal to or less than an integer (PRn−1);
b) at least one (1) second labeled probe comprises a sequence, wherein the lowest number of matches of said sequence with a homologous sequence in HPV 31 or 35 is equal to an integer (PRp), and the highest number of matches with a homologous sequence in HPV 6 or HPV 11 is equal to or less than an integer (PRp−1);
c) at least one (1) third labeled probe comprises a sequence, wherein the lowest number of matches of said sequence with a homologous sequence in HPV 18, 45 or 59 is equal to an integer (PRq), and the highest number of matches with a homologous sequence in HPV 6 or HPV 11 is equal to or less than an integer (PRq−1);
d) at least one (1) fourth labeled probe comprises a sequence, wherein the lowest number of matches of said sequence with a homologous sequence in HPV 39 or 68 is equal to an integer (PRs), and the highest number of matches with a homologous sequence in HPV 6 or HPV 11 is equal to or less than an integer (PRs−1); and
e) at least one (1) fifth labeled probe comprises a sequence, wherein the lowest number of matches of said sequence with a homologous sequence in HPV 51 or 56 is equal to an integer (PRt), and the highest number of matches with a homologous sequence in HPV 6 or HPV 11 is equal to or less than an integer (PRt−1).

81. The method of claim 80 wherein at least one of said first labeled probe, said second labeled probe, said third nucleic acid probe, said fourth labeled probe and said fifth labeled probe comprises the same sequence.

82. The method of claim 60 wherein at least one of said first nucleic acid construct, said second nucleic acid construct, said third nucleic acid probe, said fourth labeled probe and said fifth labeled probe of said first set comprises the same sequence.

83. The method of claim 60 wherein at least one of said first nucleic acid construct, said second nucleic acid construct, said third nucleic acid probe, said fourth labeled probe and said fifth labeled probe of said second set comprises the same sequence.

84. The method of claim 60 wherein one or more of said nucleic acid constructs comprises a label.

85. The method of claim 84 wherein said label comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination of the foregoing.

86. The method of claim 60, wherein said method comprises a nucleic acid amplification process.

87. The method of claim 84, wherein said amplification process comprises the polymerase chain reaction, the ligase chain reaction, the GAP-LCR method, the 3SR reaction, the NASBA reaction, the Transcription Mediated Amplification reaction, the Strand Displacement Amplification reaction, or the isothermal hairpin amplification reaction.

88. A method of detecting the presence of HPV which comprises:
a) providing:
(i) a sample that may contain nucleic acids from one or more HPV types;
(ii) two sets of primers wherein one or more nucleic acid constructs of a first set of primers are complementary to sequences in one strand of HPV 16, 18, 45, 51, 52 and 56 and wherein one or more nucleic acid constructs of a second set of primers are complementary to the other strand of HPV 16, 18, 45, 51, 52 and 56 and wherein the primers of said first and second sets are complementary to more than one of said HPV types; and
(iii) reagents for carrying out a nucleic acid amplification reaction;
b) carrying out an amplification reaction under conditions where: A) sequences from HPV 16, 18, 45, 51, 52 or 56 are amplified; and: B) if present in said sample, sequences from HPV 6 and HPV 11 are not amplified; and c) determining the presence of amplified product and thereby the presence of HPV.

89. The method of claim 88, wherein said amplification reaction comprises the polymerase chain reaction, the ligase chain reaction, the GAP-LCR method, the 3SR reaction, the NASBA reaction, the Transcription Mediated Amplification reaction, the Strand Displacement Amplification reaction, or the isothermal hairpin amplification reaction.

90. The method of claim 88 wherein said primers (i), said reagents (ii) or both said primers (i) and said reagents (ii) comprise a label.

91. The method of claim 90 wherein said label is attached to a nucleotide.

92. The method of claim 90 or 91, wherein said label comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination of the foregoing.

93. The method of claim 90 or 91 wherein said label comprises an intercalating dye.

94. A method of detecting the presence of HPV which comprises:
a) providing:
(i) a sample that may contain nucleic acids from one or more HPV types;
(ii) reagents for carrying out a nucleic acid reaction; and
(iii) two sets of primers wherein a first set of primers is complementary to one strand of an HPV nucleic acid and a second set of primers is complementary to the other strand of said HPV nucleic acid and wherein said first set comprises:
A) at least one (1) first nucleic acid construct comprising a nucleic acid sequence, wherein the lowest number of matches of said sequence with a homologous sequence in HPV 16 or HPV 52 is equal to an integer (n), and the highest number of matches with a homologous sequence in HPV 6 or HPV 11 is equal to or less than an integer (n−1);
B) at least one (1) second nucleic acid construct comprising a sequence, wherein the lowest number of matches of said sequence with a homologous sequence in HPV 18 or HPV 45 or is equal to an integer (q), and the highest number of matches with a homologous sequence in HPV 6 or HPV 11 is equal to or less than an integer (q−1); and
C) at least one (1) third nucleic acid construct comprising a sequence, wherein the lowest number of matches of said sequence with a homologous sequence in HPV 51 or HPV 56 is equal to an integer (t), and the highest number of matches with a homologous sequence in HPV 6 or HPV 11 is equal to or less than an integer (t−1); and said second set comprises one or more nucleic acid constructs complementary to sequences in HPV 16, 18, 45, 51, 52 or 56;
b) carrying out an amplification reaction under conditions where A) sequences from HPV 16, 18, 45, 51, 52 or 56 are amplified and B) sequences from HPV 6 and HPV 11 are not amplified; and
c) determining the presence of amplified product and thereby the presence of HPV.

95. The method of claim 94, wherein said amplification reaction comprises the polymerase chain reaction, the ligase chain reaction, the GAP-LCR method, the 3SR reaction, the NASBA reaction, the Transcription Mediated Amplification reaction, the Strand Displacement Amplification reaction, or the isothermal hairpin amplification reaction.

96. The method of claim 94, wherein said primers (i), said reagents (ii) or both said primers (i) and said reagents (ii) comprise a label.

97. The method of claim 96 wherein said label is attached to a nucleotide.

98. The method of claim 96 or 97, wherein said label comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination of the foregoing.

99. The method of claim 96 or 97 wherein said label comprises an intercalating dye.

100. A process for preparing one or more copies of a target nucleic acid after alteration of primer binding sites, comprising the steps of:
(A) providing:
(i) a target nucleic acid to be copied; and
(ii) at least one first forward primer and at least one second forward primer wherein:
(a) said first forward primer comprises one or more selective degenerate bases;
(b) said first forward primer comprises sequences substantially complementary to a first region of said target nucleic acid;
(c) said second forward primer comprises sequences substantially complementary to a nucleic acid formed by using said first forward primer as a template; and
(d) said second forward primer lacks said one or more degenerate bases in said first forward primer;
(iii) one or more reverse primers wherein said reverse primers comprise sequences substantially identical to a second region of said target nucleic acid; and
(iv) means for template-dependent nucleic acid synthesis;
(B) contacting said target nucleic acid with said first forward primer;
(C) extending said first forward primer by means of a template-dependent polymerase to form a first copy; and
(D) rendering a reverse primer binding sequence available in said first copy;
(E) contacting said first copy with said reverse primer;
(F) extending said reverse primer using said first copy as a template wherein at least one of the nucleotides incorporated into a site opposite a degenerate base in said first forward primer is different from the nucleotide in the target nucleic acid used as a template in step (B) thereby forming an altered forward primer binding sequence in said second copy;
(G) rendering said altered forward primer binding sequence available in said second copy;
(H) contacting said second copy with said second forward primer;
(I) extending said second forward primer using said second copy as a template, thereby producing a third copy; and
(J) optionally continuing a further series of rendering, contacting and extension steps and thereby providing one or more copies of said target nucleic acid with an altered primer binding site.

101. The process of claim 100, wherein said one or more reverse primers comprises at least one first reverse primer and at least one second reverse primer wherein:
    (a) said first reverse primer comprises one or more selective degenerate bases;
    (b) said first reverse primer comprises sequences substantially identical to sequences of a second region of said nucleic acid;
    (c) said second reverse primer comprises sequences substantially complementary to a nucleic acid formed by using said first reverse primer as a template; and
    (d) said second reverse primer lacks said one or more degenerate bases in said first reverse primer.

102. The process of claim 100 or 101, wherein a further series of rendering, contacting and extending steps are carried to provide additional copies of said target nucleic acids with altered primer binding sequences.

103. The process of claim 102, wherein after a series of rendering, contacting and extending steps, the conditions of contacting and extension are changed such that the target nucleic acid provided in said providing step (i) is less efficiently used as a target for extension events by said first forward primer or said first reverse primer, compared to the use of said extension products by said second forward primer or said second reverse primer.

104. The process of claim 100 wherein said second forward primer comprises one or more additional bases at its 3' end compared to said first forward primer.

105. The process of claim 101 wherein said second reverse primer comprises one or more additional bases at its 3' end compared to said first reverse primer.

106. The process of claim 100 or 101 wherein said selective degenerate base in said first forward primer or said first reverse primer comprises Inosine, "K" or a combination of the preceding.

107. The process of claim 106 wherein said second forward primer or said second reverse primer comprises a G in the position occupied by Inosine in said first forward primer or said second forward primer.

108. The process of claim 106 wherein said second forward primer or said second reverse primer comprises an A in the position occupied by "K" in said first forward primer or said second forward primer.

109. The process of claim 100 or 101, wherein said first forward primer, said second forward primer, said first reverse primer, said second reverse primer or any combination thereof additionally comprise one or more degenerate bases wherein said additional degenerate base lacks a substantial preference for a particular base as a substrate for incorporation when said additional base is used as a template.

110. The process of claim 109 wherein said degenerate base lacking a substantial preference for a particular base as a substrate for incorporation is selected from the group comprising 8-oxo-guanosine and "P".

111. The process of claim 100, 101 or 102, further comprising the step of detecting the presence of said altered priming binding sequence wherein said detection is carded out by measurement of the binding of a labeled probe wherein said labeled probe is complementary to said altered prime binding sequence.

112. The process of claim 111, wherein said labeled probes comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

113. The process of claim 100, 101 or 102, wherein one or more labeled nucleotides or labeled nucleotide analogues are incorporated.

114. The process of claim 113, wherein said labeled nucleotides or labeled nucleotide analogues comprises one or more labels selected from the group consisting of biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

115. The process of claim 100, 101 or 102, wherein one or more of said rendering steps comprises thermal denaturation, secondary structure formation, enzyme digestion, strand displacement or any combination thereof.

116. The process of claim 115 wherein said enzyme comprises RnaseH or a restriction enzyme.

117. The process of claim 102, further comprising the step of detecting the presence of target nucleic acid sequences other than said forward primer binding sequence, said altered forward primer binding sequence, said reverse primer binding sequence and said altered reverse primer binding sequence.

118. The process of claim 100, wherein said means (iv) for template-dependent nucleic acid synthesis comprises one or more members selected from the group consisting Taq DNA polymerase, Klenow Fragment, DNA polymerase I, Bst DNA polymerase, Bca DNA polymerase, Tth DNA polymerase, T4 DNA polymerase, Tfl DNA polymerase, Pfx DNA polymerase, Elongase, Herculase, Taq Plus, Deep-vent Polymerase, Vent DNA polymerase, T4 DNA polymerase, T7 DNA polymerase, Bca DNA polymerase, Thermal Ace™ polymerase, HIV-1 reverse transcriptase, HIV-2 reverse transcriptase, AMV reverse transcriptase, MMLV reverse transcriptase, RSV reverse transcriptase, ALV reverse transcriptase, MuLV reverse transcriptase, Sensiscript, SuperScript™, Thermo Script™, Omniscript or any mutants or modified versions of the foregoing.

119. The process of claim 100, 101 or 102, wherein said target nucleic acid is RNA or DNA.

120. The process of claim 100, 101 or 102, wherein said target nucleic acid comprises sequences of Human Papilloma Virus.

121. The process of claim 100, 101 or 102 wherein said rendering, contacting and extension steps take place during a polymerase chain reaction, a 3SR reaction, a NASBA reaction, a Transcription Mediated Amplification reaction, a Strand Displacement Amplification reaction or an isothermal hairpin amplification reaction.

122. A process for preparing one or more complementary copies of a target nucleic acid with altered primer binding site comprising the steps of:
    (A) providing:
        (i) a target nucleic acid to be copied; and
        (ii) at least one first forward primer and at least one second forward primer wherein:
            (a) said first forward primer comprises one or more selective degenerate bases;
            (b) said first forward primer comprises sequences substantially complementary to a first region of said target nucleic acid;
            (c) said second forward primer comprises sequences substantially complementary to a nucleic acid formed by using said first forward primer as a template;

(d) said second forward primer comprises a non-degenerate base in at least one position occupied by said selective degenerate base in said first forward primer; and (e) said non-degenerate base is the complement of the preferred base that is incorporated when said selective degenerate base is used in a template;

(iii) one or more reverse primers wherein said reverse primers comprise sequences substantially identical to a second region of said target nucleic acid; and (iv) means for template-dependent nucleic acid synthesis;

(B) contacting said target nucleic acid with said first forward primer;
(C) extending said first forward primer by means of a template-dependent polymerase to form a first copy;
(D) rendering a reverse primer binding sequence available in said first copy;
(E) contacting said first copy with said reverse primer;
(F) extending said reverse primer using said first copy as a template wherein at least one of the nucleotides incorporated into a site opposite a degenerate base in said first forward primer is different from the nucleotide in the target nucleic acid used as a template in step (b) thereby forming an altered forward primer binding sequence in said second copy;
(G) rendering said altered forward primer binding sequence available in said second copy;
(H) contacting said second copy with said second forward primer;

(I) extending said second forward primer using said second copy as a template, thereby providing a third copy of said target nucleic acid; and (J) optionally continuing a further series of rendering, contacting and extension steps and thereby providing one or more copies of said target nucleic acid with an altered primer binding site.

123. The process of claim 122, wherein said one or more reverse primers comprises at least one first reverse primer and at least one second reverse primer wherein:
(a) said first reverse primer comprises one or more selective degenerate bases;
(b) said first reverse primer comprises sequences substantially identical to sequences of a second region of said nucleic acid;

(c) said second reverse primer comprises sequences substantially complementary to a nucleic acid formed by using said first reverse primer as a template; and (d) said second reverse primer lacks said one or more degenerate bases in said first reverse primer.

124. The process of claim 122 or 123, wherein a further series of rendering, contacting and extending steps are carried to provide additional copies of said target nucleic acids with altered primer binding sequences.

125. The process of claim 124, wherein after a series of rendering, contacting and extending steps, the conditions of contacting and extension are changed such that the target nucleic acid provided in said providing step (i) is less efficiently used as a target for extension events by said first forward primer or said first reverse primer, compared to the use of said extension products by said second forward primer or said second reverse primer.

126. The process of claim 122 wherein said second forward primer comprises one or more additional bases at its 3' end compared to said first forward primer.

127. The process of claim 122 wherein said second reverse primer comprises one or more additional bases at its 3' end compared to said first reverse primer.

128. The process of claim 122 or 123 wherein said selective degenerate base in said first forward primer or said first reverse primer comprises Inosine, "K" or a combination of the preceding.

129. The process of claim 128 wherein said second forward primer or said second reverse primer comprises a G in the position occupied by Inosine in said first forward primer or said second forward primer.

130. The process of claim 128 wherein said second forward primer or said second reverse primer comprises an A in the position occupied by "K" in said first forward primer or said second forward primer.

131. The process of claim 122 or 123, wherein said first forward primer, said second forward primer, said first reverse primer, said second reverse primer or any combination thereof additionally comprise one or more degenerate bases wherein said additional degenerate base lacks a substantial preference for a particular base as a substrate for incorporation when said additional base is used as a template.

132. The process of claim 131 wherein said degenerate base lacking a substantial preference for a particular base as a substrate for incorporation is selected from the group comprising 8-oxo-guanosine and "P".

133. The process of claim 122, 123 or 124, further comprising the step of detecting the presence of said altered priming binding sequence wherein said detection is carried out by measurement of the binding of a labeled probe wherein said labeled probe is complementary to said altered prime binding sequence.

134. The process of claim 133, wherein said labeled probes comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

135. The process of claim 122, 123 or 124, wherein one or more labeled nucleotides or labeled nucleotide analogues are incorporated.

136. The process of claim 135, wherein said labeled nucleotides or labeled nucleotide analogues comprises one or more labels selected from the group consisting of biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

137. The process of claim 122, 123 or 124, wherein one or more of said rendering steps comprises thermal denaturation, secondary structure formation, enzyme digestion, strand displacement or any combination thereof.

138. The process of claim 124 wherein said enzyme comprises RnaseH or a restriction enzyme.

139. The process of claim 124, further comprising the step of detecting the presence of target nucleic acid sequences other than said forward primer binding sequence, said altered forward primer binding sequence, said reverse primer binding sequence and said altered reverse primer binding sequence.

140. The process of claim 122, wherein said means (iv) for template-dependent nucleic acid synthesis comprises one or more members selected from the group consisting Taq DNA polymerase, Klenow Fragment, DNA polymerase I, Bst DNA polymerase, Bca DNA polymerase, Tth DNA polymerase, T4

DNA polymerase, Tfl DNA polymerase, Pfx DNA polymerase, Elongase, Herculase, Taq Plus, Deep-vent Polymerase, Vent DNA polymerase, T4 DNA polymerase, T7 DNA polymerase, Bca DNA polymerase, Thermal Ace™ polymerase, HIV-1 reverse transcriptase, HIV-2 reverse transcriptase, AMV reverse transcriptase, MMLV reverse transcriptase, RSV reverse transcriptase, ALV reverse transcriptase, MuLV reverse transcriptase, Sensiscript, SuperScript™, Thermo Script™, Omniscript or any mutants or modified versions of the foregoing.

141. The process of claim 122, 123 or 124, wherein said target nucleic acid is RNA or DNA.

142. The process of claim 122, 123 or 124, wherein said target nucleic acid comprises sequences of Human Papilloma Virus.

143. The process of claim 122, 123 or 124, wherein said rendering, contacting and extension steps take place during a polymerase chain reaction, a 3SR reaction, a NASBA reaction, a Transcription Mediated Amplification reaction, a Strand Displacement Amplification reaction or an isothermal hairpin amplification reaction.

144. A process for preparing one or more copies of a target nucleic acid comprising the steps of:
(A) providing:
  (i) a target nucleic acid to be copied; and
  (ii) at least one first forward primer and at least one second forward primer wherein:
    (A) said first forward primer comprises one or more selective degenerate bases;
    (B) said first forward primer comprise sequences substantially complementary to sequences of a first region of said nucleic acid;
    (C) said second forward primer comprise sequences substantially complementary to a nucleic acid formed by using said first forward primer as a template; and
    (D) said second forward primer comprises a non-degenerate base in at least one position occupied by said selective degenerate base in said first forward primer and wherein said non-degenerate base is the complement of the preferred base that is incorporated when said selective degenerate base is used in a template;
  (iii) one or more reverse primers wherein said reverse primers comprise sequences substantially identical to a second region of said target nucleic acid; and
  (iv) means for template-dependent nucleic acid synthesis;
(B) contacting said target nucleic acid with said first forward primer and binding said first forward primer to a forward primer binding sequence;
(C) extending said first forward primer by means of a template-dependent polymerase to form a first copy;
(D) rendering a reverse primer binding sequence available in said first copy;
(E) contacting said first copy with said reverse primer and binding said reverse primer to said reverse primer binding sequence;
(F) extending said reverse primer using said first copy as a template wherein said preferred nucleotide is inserted opposite said degenerate base;
(G) rendering a forward primer binding sequence available in said second copy;
(H) contacting said second copy with said second forward primer and binding said second forward primer to said forward primer binding sequence in said second copy; and
(I) extending said second forward primer using said second copy as a template thereby providing a copy of said target nucleic acid; and
(J) optionally continuing a further series of rendering, contacting and extension steps and thereby providing one or more copies of said target nucleic acid.

145. The process of claim 144, wherein said one or more reverse primers comprises at least one first reverse primer and at least one second reverse primer wherein:
(a) said first reverse primer comprises one or more selective degenerate bases;
(b) said first reverse primer comprises sequences substantially identical to sequences of a second region of said nucleic acid;
(c) said second reverse primer comprises sequences substantially complementary to a nucleic acid formed by using said first reverse primer as a template; and
(d) said second reverse primer lacks said one or more degenerate bases in said first reverse primer.

146. The process of claim 144 or 145, wherein a further series of rendering, contacting and extending steps are carried to provide additional copies of said target nucleic acids with altered primer binding sequences.

147. The process of claim 146, wherein after a series of rendering, contacting and extending steps, the conditions of contacting and extension are changed such that the target nucleic acid provided in said providing step (i) is less efficiently used as a target for extension events by said first forward primer or said first reverse primer, compared to the use of said extension products by said second forward primer or said second reverse primer.

148. The process of claim 144, wherein said second forward primer comprises one or more additional bases at its 3' end compared to said first forward primer.

149. The process of claim 145, wherein said second reverse primer comprises one or more additional bases at its 3' end compared to said first reverse primer.

150. The process of claim 144 or 145, wherein said selective degenerate base in said first forward primer or said first reverse primer comprises Inosine, "K" or a combination of the preceding.

151. The process of claim 150 wherein said second forward primer or said second reverse primer comprises a G in the position occupied by Inosine in said first forward primer or said second forward primer.

152. The process of claim 150 wherein said second forward primer or said second reverse primer comprises an A in the position occupied by "K" in said first forward primer or said second forward primer.

153. The process of claim 144 or 145, wherein said first forward primer, said second forward primer, said first reverse primer, said second reverse primer or any combination thereof additionally comprise one or more degenerate bases wherein said additional degenerate base lacks a substantial preference for a particular base as a substrate for incorporation when said additional base is used as a template.

154. The process of claim 153 wherein said degenerate base lacking a substantial preference for a particular base as a substrate for incorporation is selected from the group comprising 8-oxo-guanosine and "P".

155. The process of claim 144, 145 or 146, further comprising the step of detecting the presence of said altered priming binding sequence wherein said detection is carried out by measurement of the binding of a labeled probe wherein said labeled probe is complementary to said altered prime binding sequence.

156. The process of claim 155, wherein said labeled probes comprises biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

157. The process of claim 144, 145 or 146, wherein one or more labeled nucleotides or labeled nucleotide analogues are incorporated.

158. The process of claim 157, wherein said labeled. nucleotides or labeled nucleotide analogues comprises one or more labels selected from the group consisting of biotin, iminobiotin, an electron dense component, a magnetic component, a hormone component, a metal-containing component, a fluorescent component, a chromogenic component, a chemiluminescent component, an antigen, a hapten, an antibody component, a chelating component or any combination thereof.

159. The process of claim 144, 145 or 146, wherein one or more of said rendering steps comprises thermal denaturation, secondary structure formation, enzyme digestion, strand displacement or any combination thereof.

160. The process of claim 159 wherein said enzyme comprises RnaseH or a restriction enzyme.

161. The process of claim 146, further comprising the step of detecting the presence of target nucleic acid sequences other than said forward primer binding sequence, said altered forward primer binding sequence, said reverse primer binding sequence and said altered reverse primer binding sequence.

162. The process of claim 144, wherein said means (iv) for template-dependent nucleic acid synthesis comprises Taq DNA polymerase, Klenow Fragment, DNA polymerase I, Bst DNA polymerase, Bca DNA polymerase, Tth DNA polymerase, T4 DNA polymerase, Tfl DNA polymerase, Pfx DNA polymerase, Elongase, Herculase, Taq Plus, Deep-vent Polymerase, Vent DNA polymerase, T4 DNA polymerase, T7 DNA polymerase, Bca DNA polymerase, Thermal Ace™ polymerase, HIV-1 reverse transcriptase, HIV-2 reverse transcriptase, AMV reverse transcriptase, MMLV reverse transcriptase, RSV reverse transcriptase, ALV reverse transcriptase, MuLV reverse transcriptase, Sensiscript, SuperScript™, Thermo Script™, Omniscript, any Mutants or modified versions of the foregoing or any combination of the foregoing.

163. The process of claim 144, 145 or 146, wherein said target nucleic acid is RNA or DNA.

164. The process of claim 144, 145 or 146, wherein said target nucleic acid comprises sequences of Human Papilloma Virus.

165. The process of claim 144, 145 or 146, wherein said rendering, contacting and extension steps take place during a polymerase chain reaction, a 3SR reaction, a NASBA reaction, a Transcription Mediated Amplification reaction, a Strand Displacement Amplification reaction or an isothermal hairpin amplification reaction.

* * * * *